(12) United States Patent
Mahata et al.

(10) Patent No.: US 9,572,862 B2
(45) Date of Patent: Feb. 21, 2017

(54) METHODS FOR PROMOTING LIPOLYSIS AND OXIDATION IN LIVER AND ADIPOSE TISSUE USING CATESTATIN

(71) Applicant: The Regents of the University of California, Oakland, CA (US)

(72) Inventors: Sushil K. Mahata, San Diego, CA (US); Gautam K. Bandyopadhyay, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/389,722

(22) PCT Filed: Apr. 1, 2013

(86) PCT No.: PCT/US2013/034856
§ 371 (c)(1),
(2) Date: Sep. 30, 2014

(87) PCT Pub. No.: WO2013/149259
PCT Pub. Date: Oct. 3, 2013

(65) Prior Publication Data
US 2015/0080294 A1 Mar. 19, 2015

Related U.S. Application Data

(60) Provisional application No. 61/618,197, filed on Mar. 30, 2012.

(51) Int. Cl.
*A61K 38/00* (2006.01)
*A61P 3/04* (2006.01)
*A61K 38/17* (2006.01)
*C07K 14/575* (2006.01)
*A61K 31/155* (2006.01)

(52) U.S. Cl.
CPC ............ *A61K 38/17* (2013.01); *A61K 31/155* (2013.01); *C07K 14/575* (2013.01)

(58) Field of Classification Search
CPC ...... A61K 31/155; A61K 38/17; C07K 14/575
See application file for complete search history.

(56) References Cited

U.S. PATENT DOCUMENTS

2011/0166066 A1* 7/2011 Mahata .................. A61K 38/17
514/6.7

OTHER PUBLICATIONS

Despres et al. Abdominal obesity and metabolic syndrome. Nature, 2006 vol. 444, pp. 881-887.*

* cited by examiner

*Primary Examiner* — Marcela M Cordero Garcia
(74) *Attorney, Agent, or Firm* — Joseph R. Baker, Jr.; Gavrilovich, Dodd & Lindsey LLP

(57) ABSTRACT

The invention provides methods for treating obesity in a subject comprising administering an effective amount of catestatin (CST) or its equivalent to a subject afflicted with obesity so as to maintain an effective amount of circulating catestatin in the subject to promote lipolysis and oxidation of released fatty acids in both liver and adipose tissue, thereby, reducing adipose tissue weight and hence treating obesity in the afflicted subject.

11 Claims, 18 Drawing Sheets

Catestatins:

| Species | Sequence | Chromogranin A region shown |
|---|---|---|
| BOVINE: | PDRSMRLSFRARGYGFRGPGLQLRRGWRPNS | Bovine chromogranin A$_{342-372}$ |
| HUMAN(1): | RDSSMKLSFRARAYGFRGPGPQLRRGWRPNS | Human chromogranin A$_{350-380}$ |
| HUMAN(2): | RDRSMRLSFRARAYGFRGPGPQLRRGSRPNS | Human chromogranin A$_{350-380}$ |
| PORCINE: | PDRSMRLSFRAPAYGFRGPGLQLRRGWRPNS | Porcine chromogranin A$_{341-371}$ |
| RAT: | PDRSMRLSFRARGYGFRDPGLQLRRGWRPNS | Rat chromogranin A$_{365-395}$ |
| MOUSE: | PDRSMRLSFRTRGYGFRDPGLQLRRGWRPNS | Mouse chromogranin A$_{362-392}$ |

Catestatin homologs:

| Symbol | Sequence | | |
|---|---|---|---|
| 8FAB: | PGRSLRLSCIASGFTFSNYGMHWVRQAPGKG | | |
| 1PKM: | RVNLAMNVGKARGFFKHGDVVIVLTGWRPGS | | |
| 2IG2: | PGRSLRLSCSSSGFIFSSYAMYWVRQAPGKG | | |

FASTA alignment

| % identity | General alignment score |
|---|---|
| 35.5% | 57 |
| 31.2% | 42 |
| 29.0% | 44 |

Figure 10

*Scheme I. CST regulation of key endocrine functions.*

SEQUENCE LISTING

```
<160> NUMBER OF SEQ ID NOS: 57

<210> SEQ ID NO 1
<211> LENGTH: 21
<212> TYPE: PRT
<213> ORGANISM: Homo Sapiens

<400> SEQUENCE: 1

Ser Ser Met Lys Leu Ser Phe Arg Ala Arg Ala Tyr Gly Phe Arg Gly
1               5                   10                  15
```

Pro Gly Pro Gln Leu
            20

<210> SEQ ID NO 2
<211> LENGTH: 21
<212> TYPE: PRT
<213> ORGANISM: Homo sapiens

<400> SEQUENCE: 2

Ser Ser Met Lys Leu Ser Phe Arg Ala Arg Ala Tyr Ser Phe Arg Gly
1               5                   10                  15

Pro Gly Pro Gln Leu
            20

<210> SEQ ID NO 3
<211> LENGTH: 21
<212> TYPE: PRT
<213> ORGANISM: Homo sapiens

<400> SEQUENCE: 3

Ser Ser Met Lys Leu Ser Phe Arg Ala Arg Ala Tyr Gly Phe Arg Val
1               5                   10                  15

Pro Gly Pro Gln Leu
            20

<210> SEQ ID NO 4
<211> LENGTH: 21
<212> TYPE: PRT
<213> ORGANISM: Homo sapiens

<400> SEQUENCE: 4

Ser Ser Met Lys Leu Ser Phe Arg Ala Arg Ala Tyr Gly Phe Arg Gly
1               5                   10                  15

Pro Gly Leu Gln Leu
            20

<210> SEQ ID NO 5
<211> LENGTH: 21
<212> TYPE: PRT
<213> ORGANISM: Bos taurus

<400> SEQUENCE: 5

Arg Ser Met Arg Leu Ser Phe Arg Ala Arg Gly Tyr Gly Phe Arg Gly
1               5                   10                  15

Pro Gly Leu Gln Leu
            20

<210> SEQ ID NO 6
<211> LENGTH: 21
<212> TYPE: PRT
<213> ORGANISM: Sus scrofa

<400> SEQUENCE: 6

Arg Ser Met Arg Leu Ser Phe Arg Ala Pro Ala Tyr Gly Phe Arg Gly
1               5                   10                  15

Pro Gly Leu Gln Leu
            20

<210> SEQ ID NO 7
<211> LENGTH: 21
<212> TYPE: PRT
<213> ORGANISM: Rattus norvegicus -continued

<400> SEQUENCE: 7

Arg Ser Met Arg Leu Ser Phe Arg Ala Arg Gly Tyr Gly Phe Arg Asp
1               5                   10                  15

Pro Gly Leu Gln Leu
            20

<210> SEQ ID NO 8
<211> LENGTH: 21
<212> TYPE: PRT
<213> ORGANISM: Mus musculus

<400> SEQUENCE: 8

Arg Ser Met Arg Leu Ser Phe Arg Thr Arg Gly Tyr Gly Phe Arg Asp
1               5                   10                  15

Pro Gly Leu Gln Leu
            20

<210> SEQ ID NO 9
<211> LENGTH: 21
<212> TYPE: PRT
<213> ORGANISM: Macaca mulatta

<400> SEQUENCE: 9

Arg Ser Met Lys Leu Ser Phe Arg Ala Arg Ala Tyr Gly Phe Arg Gly
1               5                   10                  15

Pro Gly Pro Gln Leu
            20

<210> SEQ ID NO 10
<211> LENGTH: 21
<212> TYPE: PRT
<213> ORGANISM: Pongo abelii

<400> SEQUENCE: 10

Ser Ser Met Lys Leu Pro Phe Arg Ala Arg Ala Tyr Gly Phe Arg Gly
1               5                   10                  15

Pro Gly Pro Gln Leu
            20

<210> SEQ ID NO 11
<211> LENGTH: 21
<212> TYPE: PRT
<213> ORGANISM: Equus caballus

<400> SEQUENCE: 11

Arg Ser Met Lys Leu Ser Phe Arg Ala Arg Ala Tyr Gly Phe Arg Gly
1               5                   10                  15

Pro Gly Leu Gln Leu
            20

<210> SEQ ID NO 12
<211> LENGTH: 21
<212> TYPE: PRT
<213> ORGANISM: Saimiri sciureus

<400> SEQUENCE: 12

His Ser Met Lys Leu Ser Phe Arg Ala Arg Ala Tyr Gly Phe Gly Gly
1               5                   10                  15

Pro Gly Pro Gln Leu
            20

```
<210> SEQ ID NO 13
<211> LENGTH: 21
<212> TYPE: PRT
<213> ORGANISM: Felis catus

<400> SEQUENCE: 13

Ser Ser Met Lys Leu Ser Phe Arg Ala Arg Ala Tyr Asp Phe Arg Gly
1               5                   10                  15

Pro Gly Leu Gln Leu
            20

<210> SEQ ID NO 14
<211> LENGTH: 21
<212> TYPE: PRT
<213> ORGANISM: Callithrix jacchus

<400> SEQUENCE: 14

His Ser Met Lys Leu Ser Phe Gln Ala Arg Ala Tyr Asp Phe Arg Gly
1               5                   10                  15

Pro Gly Pro Gln Leu
            20

<210> SEQ ID NO 15
<211> LENGTH: 21
<212> TYPE: PRT
<213> ORGANISM: Ailuropoda melanoleuca

<400> SEQUENCE: 15

Arg Ser Met Lys Leu Ser Phe Arg Ala Arg Ala Tyr Asp Phe Arg Gly
1               5                   10                  15

Pro Gly Leu Gln Leu
            20

<210> SEQ ID NO 16
<211> LENGTH: 21
<212> TYPE: PRT
<213> ORGANISM: Cricetulus griseus

<400> SEQUENCE: 16

Arg Ser Met Lys Leu Ser Phe Arg Ala Arg Ala Tyr Gly Phe Arg Asp
1               5                   10                  15

Pro Arg Pro Gln Leu
            20

<210> SEQ ID NO 17
<211> LENGTH: 21
<212> TYPE: PRT
<213> ORGANISM: Sus scrofa

<400> SEQUENCE: 17

Arg Ser Met Lys Leu Ser Phe Arg Ala Pro Ala Tyr Gly Phe Arg Gly
1               5                   10                  15

Pro Gly Leu Gln Leu
            20

<210> SEQ ID NO 18
<211> LENGTH: 18
<212> TYPE: PRT
<213> ORGANISM: Canis lupus

<400> SEQUENCE: 18

Arg Ser Met Lys Leu Ser Phe Arg Ala Arg Ala Tyr Asp Phe Arg Gly
1               5                   10                  15
```

Pro Gly

<210> SEQ ID NO 19
<211> LENGTH: 21
<212> TYPE: PRT
<213> ORGANISM: Cavia porcellus

<400> SEQUENCE: 19

Arg Ser Met Lys Leu Ser Phe Arg Ala Gln Ala Tyr Gly Phe Pro Gly
1               5                   10                  15

Pro Glu Pro Gln Leu
            20

<210> SEQ ID NO 20
<211> LENGTH: 21
<212> TYPE: PRT
<213> ORGANISM: Myotis davidii

<400> SEQUENCE: 20

Arg Ser Met Lys Leu Ser Phe Arg Ala Arg Gly Tyr Gly Phe Gly Ala
1               5                   10                  15

Pro Gly Pro Gln Leu
            20

<210> SEQ ID NO 21
<211> LENGTH: 21
<212> TYPE: PRT
<213> ORGANISM: Loxodonta africana

<400> SEQUENCE: 21

Arg Ser Met Lys Leu Ser Leu Arg Ala Arg Ser Tyr Gly Phe Gly Gly
1               5                   10                  15

Pro Gly Pro Gln Leu
            20

<210> SEQ ID NO 22
<211> LENGTH: 21
<212> TYPE: PRT
<213> ORGANISM: Otolemur garnettii

<400> SEQUENCE: 22

Arg Ser Met Lys Leu Ser Leu Gln Thr Arg Ala Tyr Asp Phe Arg Gly
1               5                   10                  15

Pro Gly Pro Gln Leu
            20

<210> SEQ ID NO 23
<211> LENGTH: 21
<212> TYPE: PRT
<213> ORGANISM: Heterocephalus glaber

<400> SEQUENCE: 23

Arg Ser Met Lys Leu Ser Phe Gln Ala Pro Ala Tyr Asp Phe Arg Gly
1               5                   10                  15

Ser Gly Pro Gln Leu
            20

<210> SEQ ID NO 24
<211> LENGTH: 21
<212> TYPE: PRT
<213> ORGANISM: Tupaia chinensis

```
<400> SEQUENCE: 24

Arg Ser Met Lys Leu Ser Phe Gln Ser Arg Ala Tyr Gly Phe Arg Gly
1               5                   10                  15

Pro Arg His Gln Leu
            20

<210> SEQ ID NO 25
<211> LENGTH: 21
<212> TYPE: PRT
<213> ORGANISM: Orcinus orca

<400> SEQUENCE: 25

Arg Ala Met Lys Leu Ser Phe Arg Ala Arg Gly Tyr Asp Phe Ser Gly
1               5                   10                  15

Pro Gly Leu Gln Leu
            20

<210> SEQ ID NO 26
<211> LENGTH: 29
<212> TYPE: PRT
<213> ORGANISM: Bos taurus

<400> SEQUENCE: 26

Pro Asp Arg Ser Met Arg Leu Ser Phe Arg Ala Arg Gly Tyr Gly Phe
1               5                   10                  15

Arg Gly Pro Gly Leu Gln Leu Arg Arg Gly Trp Arg Pro
            20                  25

<210> SEQ ID NO 27
<211> LENGTH: 21
<212> TYPE: PRT
<213> ORGANISM: Artificial Sequence
<220> FEATURE:
<223> OTHER INFORMATION: Retro and retroinverso peptide

<400> SEQUENCE: 27

Leu Gln Pro Gly Pro Gly Arg Phe Gly Tyr Ala Arg Ala Arg Phe Ser
1               5                   10                  15

Leu Lys Met Ser Ser
            20

<210> SEQ ID NO 28
<211> LENGTH: 20
<212> TYPE: DNA
<213> ORGANISM: Artificial Sequence
<220> FEATURE:
<223> OTHER INFORMATION: Forward Primer Srebp-1c

<400> SEQUENCE: 28
ggagccatgg attgcacatt                                           20

<210> SEQ ID NO 29
<211> LENGTH: 20
<212> TYPE: DNA
<213> ORGANISM: Artificial Sequence
<220> FEATURE:
<223> OTHER INFORMATION: Reverse Primer Srebp-1c

<400> SEQUENCE: 29
gcttccagag aggaggccag                                           20

<210> SEQ ID NO 30
<211> LENGTH: 23
```

```
<212> TYPE: DNA
<213> ORGANISM: Artificial Sequence
<220> FEATURE:
<223> OTHER INFORMATION: Forward Primer GAPDH

<400> SEQUENCE: 30
tatgtcgtgg agtctactgg tgt                                              23

<210> SEQ ID NO 31
<211> LENGTH: 23
<212> TYPE: DNA
<213> ORGANISM: Artificial Sequence
<220> FEATURE:
<223> OTHER INFORMATION: Reverse Primer GAPDH

<400> SEQUENCE: 31
gtcatcatac ttggcaggtt tct                                              23

<210> SEQ ID NO 32
<211> LENGTH: 20
<212> TYPE: DNA
<213> ORGANISM: Artificial Sequence
<220> FEATURE:
<223> OTHER INFORMATION: Forward Primer GPAT4

<400> SEQUENCE: 32
tgtctggttt gagcgttctg                                                  20

<210> SEQ ID NO 33
<211> LENGTH: 20
<212> TYPE: DNA
<213> ORGANISM: Artificial Sequence
<220> FEATURE:
<223> OTHER INFORMATION: Reverse Primer GPAT4

<400> SEQUENCE: 33
ttctgggaag atgaggatgg                                                  20

<210> SEQ ID NO 34
<211> LENGTH: 20
<212> TYPE: DNA
<213> ORGANISM: Artificial Sequence
<220> FEATURE:
<223> OTHER INFORMATION: Forward Primer PPAR-gamma1

<400> SEQUENCE: 34
gagtgtgacg acaagatttg                                                  20

<210> SEQ ID NO 35
<211> LENGTH: 20
<212> TYPE: DNA
<213> ORGANISM: Artificial Sequence
<220> FEATURE:
<223> OTHER INFORMATION: Reverse Primer PPAR-gamma1

<400> SEQUENCE: 35
ggtgggccag aatggcatct                                                  20

<210> SEQ ID NO 36
<211> LENGTH: 18
<212> TYPE: DNA
<213> ORGANISM: Artificial Sequence
<220> FEATURE:
<223> OTHER INFORMATION: Forward Primer CD36

<400> SEQUENCE: 36
```

```
tccagccaat gcctttgc                                                18
```

<210> SEQ ID NO 37
<211> LENGTH: 26
<212> TYPE: DNA
<213> ORGANISM: Artificial Sequence
<220> FEATURE:
<223> OTHER INFORMATION: Reverse Primer CD36

<400> SEQUENCE: 37

```
tggagaatta cttttcagt gcagaa                                        26
```

<210> SEQ ID NO 38
<211> LENGTH: 18
<212> TYPE: DNA
<213> ORGANISM: Artificial Sequence
<220> FEATURE:
<223> OTHER INFORMATION: Forward Primer UCP2

<400> SEQUENCE: 38

```
cagccagcgc ccagtacc                                                18
```

<210> SEQ ID NO 39
<211> LENGTH: 21
<212> TYPE: DNA
<213> ORGANISM: Artificial Sequence
<220> FEATURE:
<223> OTHER INFORMATION: Reverse Primer UCP2

<400> SEQUENCE: 39

```
caatgcggac ggaggcaaag c                                            21
```

<210> SEQ ID NO 40
<211> LENGTH: 21
<212> TYPE: DNA
<213> ORGANISM: Artificial Sequence
<220> FEATURE:
<223> OTHER INFORMATION: Forward Primer CPT1

<400> SEQUENCE: 40

```
caggattttg ctgtcaacct c                                            21
```

<210> SEQ ID NO 41
<211> LENGTH: 19
<212> TYPE: DNA
<213> ORGANISM: Artificial Sequence
<220> FEATURE:
<223> OTHER INFORMATION: Reverse Primer CPT1

<400> SEQUENCE: 41

```
gagcatctcc atggcgtag                                               19
```

<210> SEQ ID NO 42
<211> LENGTH: 17
<212> TYPE: DNA
<213> ORGANISM: Artificial Sequence
<220> FEATURE:
<223> OTHER INFORMATION: Forward Primer ACOX

<400> SEQUENCE: 42

```
gtcgaccttg ttcgcca                                                 17
```

<210> SEQ ID NO 43
<211> LENGTH: 18
<212> TYPE: DNA
<213> ORGANISM: Artificial Sequence
<220> FEATURE:
<223> OTHER INFORMATION: Reverse Primer ACOX

<400> SEQUENCE: 43
ggttcctcag cacggctt                                                  18

<210> SEQ ID NO 44
<211> LENGTH: 18
<212> TYPE: DNA
<213> ORGANISM: Artificial Sequence
<220> FEATURE:
<223> OTHER INFORMATION: Forward Primer PPAR-alpha

<400> SEQUENCE: 44
gggctctccc acatcctt                                                  18

<210> SEQ ID NO 45
<211> LENGTH: 22
<212> TYPE: DNA
<213> ORGANISM: Artificial Sequence
<220> FEATURE:
<223> OTHER INFORMATION: Reverse Primer PPAR-alpha

<400> SEQUENCE: 45
cccatttcgg tagcaggtag tc                                             22

<210> SEQ ID NO 46
<211> LENGTH: 31
<212> TYPE: PRT
<213> ORGANISM: Bos taurus

<400> SEQUENCE: 46

Pro Asp Arg Ser Met Arg Leu Ser Phe Arg Ala Arg Gly Tyr Gly Phe
1               5                   10                  15

Arg Gly Pro Gly Leu Gln Leu Arg Arg Gly Trp Arg Pro Asn Ser
            20                  25                  30

<210> SEQ ID NO 47
<211> LENGTH: 31
<212> TYPE: PRT
<213> ORGANISM: Homo sapiens

<400> SEQUENCE: 47

Arg Asp Ser Ser Met Lys Leu Ser Phe Arg Ala Arg Ala Tyr Gly Phe
1               5                   10                  15

Arg Gly Pro Gly Pro Gln Leu Arg Arg Gly Trp Arg Pro Asn Ser
            20                  25                  30

<210> SEQ ID NO 48
<211> LENGTH: 31
<212> TYPE: PRT
<213> ORGANISM: Homo sapiens

<400> SEQUENCE: 48

Arg Asp Arg Ser Met Arg Leu Ser Phe Arg Ala Arg Ala Tyr Gly Phe
1               5                   10                  15

Arg Gly Pro Gly Pro Gln Leu Arg Arg Gly Ser Arg Pro Asn Ser
            20                  25                  30

<210> SEQ ID NO 49
<211> LENGTH: 31
<212> TYPE: PRT
<213> ORGANISM: Sus scrofa

<400> SEQUENCE: 49

Pro Asp Arg Ser Met Arg Leu Ser Phe Arg Ala Pro Ala Tyr Gly Phe
1               5                   10                  15

Arg Gly Pro Gly Leu Gln Leu Arg Arg Gly Trp Arg Pro Asn Ser
            20                  25                  30

<210> SEQ ID NO 50
<211> LENGTH: 31
<212> TYPE: PRT
<213> ORGANISM: Rattus norvegicus

<400> SEQUENCE: 50

Pro Asp Arg Ser Met Arg Leu Ser Phe Arg Ala Arg Gly Tyr Gly Phe
1               5                   10                  15

Arg Asp Pro Gly Leu Gln Leu Arg Arg Gly Trp Arg Pro Asn Ser
            20                  25                  30

<210> SEQ ID NO 51
<211> LENGTH: 31
<212> TYPE: PRT
<213> ORGANISM: Mus musculus

<400> SEQUENCE: 51

Pro Asp Arg Ser Met Arg Leu Ser Phe Arg Thr Arg Gly Tyr Gly Phe
1               5                   10                  15

Arg Asp Pro Gly Leu Gln Leu Arg Arg Gly Trp Arg Pro Asn Ser
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Catestatin homolog 8FAB

<400> SEQUENCE: 52

Pro Gly Arg Ser Leu Arg Leu Ser Cys Ile Ala Ser Gly Phe Thr Phe
1               5                   10                  15

Ser Asn Tyr Gly Met His Trp Val Arg Gln Ala Pro Gly Lys Gly
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Catestatin homolog 1PKM

<400> SEQUENCE: 53

Arg Val Asn Leu Ala Met Asn Val Gly Lys Ala Arg Gly Phe Phe Lys
1               5                   10                  15

His Gly Asp Val Val Ile Val Leu Thr Gly Trp Arg Pro Gly Ser
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Catestatin homolog 2IG2

<400> SEQUENCE: 54

Pro Gly Arg Ser Leu Arg Leu Ser Cys Ser Ser Ser Gly Phe Ile Phe

```
1               5                  10                 15

Ser Ser Tyr Ala Met Tyr Trp Val Arg Gln Ala Pro Gly Lys Gly
                20                 25                 30

<210> SEQ ID NO 55
<211> LENGTH: 21
<212> TYPE: PRT
<213> ORGANISM: Bos Taurus

<400> SEQUENCE: 55

Arg Ser Met Lys Leu Ser Phe Arg Ala Arg Ala Tyr Gly Phe Arg Gly
1               5                   10                  15

Pro Gly Leu Gln Leu
            20

<210> SEQ ID NO 56
<211> LENGTH: 21
<212> TYPE: PRT
<213> ORGANISM: Bos Taurus

<400> SEQUENCE: 56

Arg Ser Met Arg Leu Ser Phe Arg Ala Arg Gly Tyr Gly Phe Arg Gly
1               5                   10                  15

Pro Gly Pro Gln Leu
            20

<210> SEQ ID NO 57
<211> LENGTH: 21
<212> TYPE: PRT
<213> ORGANISM: Mus musculus

<400> SEQUENCE: 57

Arg Ser Met Lys Leu Ser Phe Arg Thr Arg Ala Tyr Gly Phe Arg Asp
1               5                   10                  15

Pro Gly Pro Gln Leu
            20
```

METHODS FOR PROMOTING LIPOLYSIS AND OXIDATION IN LIVER AND ADIPOSE TISSUE USING CATESTATIN

This invention was made with government support under Grant No. 1 I01 BX000323-01A2 awarded by VA BLR&D Merit Review Award & RCS Award. The government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

Chromogranin A knockout (Chga-KO) mice display increased adiposity despite high levels of circulating catecholamines and leptin. Consistent with diet-induced obese (DIO) mice, desensitization of leptin receptors (Ob-R) due to hyperleptinemia is believed to contribute to the obese phenotype of these KO mice. In contrast, obesity in Ob/Ob mice is caused by leptin deficiency. To characterize the metabolic phenotype, Chga-KO mice were treated with a CHGA-derived peptide catestatin ($CHGA_{352-372}$) that is deficient in these mice. CST treatment reduced fat depot size and increased lipolysis and fatty acid oxidation. In liver, CST enhanced oxidation of fatty acids as well as their assimilation into lipids, effects that are attributable to the upregulation of genes promoting fatty acid oxidation (Ppar$\alpha$, Acox, Ucp2 and Cpt1$\alpha$) and incorporation into lipids (Gpat and Cd36). CST did not affect basal or isoproterenol-stimulated cAMP production in adipocytes but inhibited phospholipase-C activation by the alpha-adrenergic receptor ($\alpha$-ADR) agonist phenylephrine suggesting inhibition of $\alpha$-ADR signaling by CST. Indeed, CST mimicked the lipolytic effect of the $\alpha$-ADR blocker phentolamine on adipocytes. Moreover, CST reversed the hyperleptinemia of Chga-KO mice and improved leptin signaling as determined by phosphorylation of AMPK and Stat3. CST also improved peripheral leptin sensitivity in DIO mice. In Ob/Ob mice, CST enhanced leptin-induced signaling in adipose tissue. In conclusion, our results implicate CST in a novel pathway that promotes lipolysis and fatty acid oxidation by blocking $\alpha$-ADR signaling as well as by enhancing leptin receptor signaling.

Chromogranin A (CHGA in humans, Chga in mice), a 48-kDa acidic secretory proprotein (1-3), gives rise to several peptides of biological importance, which include the dysglycemic hormone pancreastatin (PST: $CHGA_{250-301}$) (4,5), the vasodilator vasostatin ($CHGA_{1-76}$) (6), and the anti-hypertensive peptide catestatin (CST: $CHGA_{352-372}$) that inhibits nicotine-induced catecholamine release (7-9). Initially identified as a physiological brake in catecholamine secretion (7), CST has been established as a pleiotropic hormone having effects on promoting angiogenesis (10), lowering of blood pressure (8,11,12) and cardiac contractility (13-15) as well as enhancing baroreflex sensitivity (16, 17) and heart rate variability (18).

In addition to the above cardiovascular functions, CST has an antimicrobial activity (19,20) and also regulates mast cell migration, cytokine production and release (21), smooth muscle cell proliferation (22), and monocyte migration (23). CST can act both extracellularly and intracellularly because the peptide can cross cell membrane (24,25).

Fat cell functions are regulated by catecholamines through four types of adrenergic receptors (ADR): $\beta$1, $\beta$2, $\beta$3 and $\alpha$2 (26,27). Activation of the three $\beta$-ADRs is positively coupled to adenylyl cyclase by stimulatory GTP sensitive proteins, resulting in enhanced production of cyclic AMP. Cyclic AMP activates protein kinase A (PKA), which in turn phosphorylates hormone sensitive lipase (HSL) leading to hydrolysis of triglycerides (lipolysis). In contrast, $\alpha$2-ADR activation has the opposite effects on lipolysis because it is coupled to inhibitory GTP sensitive proteins (28-31). Therefore, the net action of catecholamines depends on the balance between $\beta$- and $\alpha$-ADRs (27). Normally, the $\beta$-ADR-mediated lipolytic action dominates. Sustained activation of sympathetic nervous system or increased plasma catecholamines is often associated with desensitization of $\beta$-ADR (32). In vivo studies have shown that the lipolytic action of catecholamines is blunted in obese subjects (33, 34). Catecholamine-induced regulation of lipolysis through $\beta$-ADR desensitization has also been demonstrated in vitro (32,35). Repeated treatment with epinephrine results in the suppression of basal and epinephrine-stimulated lipolysis in lean and obese subjects (36). Even the in vivo lipolytic response to epinephrine is desensitized by prior exposure to epinephrine (37). In view of the above, we hypothesize that the increased fat mass in hyperadrenergic Chga-KO mice (38) reflects $\beta$-ADR desensitization by increased plasma catecholamines (8). Since catecholamines are known to inhibit leptin secretion (39-41), $\beta$-ADR desensitization may prevent such inhibition and lead to increased leptin level along with the increased adipose mass as found in Chga-KO mice and other obese models. Chronic hyperleptinemia in turn may desensitize Ob-R and perpetuate the obese phenotype.

The invention, in one embodiment, is based on CST that breaks this cycle and reduces obesity by restoring ADR and Ob-R sensitivity through normalization of catecholamine and leptin levels. Indeed, we found that chronic CST administration to obese Chga-KO mice resulted in a dramatic lean phenotype. CST treatment also reduced body weight and adipose mass in DIO mice without reducing food intake. Interestingly, CST could enhance leptin effects on adipose tissue metabolism and signaling in both DIO and leptin-deficient Ob/Ob mice. Our findings suggest that the reduction in fat mass after chronic CST treatment is due to increased lipolysis and lipid mobilization through CST action on $\alpha$2-ADR and leptin receptor. In line with this, CST promoted fatty acid oxidation and leptin signaling.

SUMMARY OF THE INVENTION

The invention provides methods for treating obesity in a subject comprising administering an effective amount of a CST or its equivalent to a subject afflicted with obesity so as to maintain an effective amount of circulating CST in the subject to promote lipolysis and oxidation of released fatty acids in both liver and adipose tissue, thereby reducing adipose tissue weight and hence treating obesity in the afflicted subject.

The invention also provides methods for reversing leptin resistance in the brain and peripheral tissue of a subject comprising administering an effective amount of CST or its equivalent to a subject with leptin resistance so as to maintain an effective amount of circulating CST in the subject to decrease hyperleptinemia and minimize chronic leptin overexposure in the obese patient, thereby, restoring leptin sensitivity in brain and peripheral tissue of the obese patient.

The invention also provides methods for decreasing triglyceride levels in the plasma of a subject comprising administration of an effective amount of CST or its equivalent to a subject so as to maintain an effective amount of circulating CST to elicit decrease in plasma triglyceride levels; thereby decreasing triglyceride levels in the subject.

The invention also provides methods for decreasing obesity and hypertension in a subject comprising administering an effective amount of CST or its equivalent to a subject afflicted with obesity so as to maintain an effective amount of circulating CST to promote lipolysis and reduce catecholamine and Neuropeptide Y (NPY) levels, thereby, decreasing obesity and reducing hypertension in a subject.

The invention also provides methods for increasing therapeutic effectiveness of an anti-diabetic drug, by reducing undesirable side effects such as weight gain and cardiovascular risks in a subject comprising administering an effective amount of CST or its equivalent to a subject so as to maintain an effective amount of circulating CST to promote lipolysis and reduce hypertension, thereby, reducing undesirable side effects of weight gain and cardiovascular risks associated with the anti-diabetic drug.

The invention also provides methods for enhancing lipolysis in a subject comprising administering an effective amount of: (i) CST or its equivalent; and optionally, (ii) CST or its equivalent in combination with an agonist for β-ADR; or (iii) antagonist for α-ADR receptor in combination with an agonist for β-ADR to a subject thereby increasing lipolysis in the subject.

The invention also provides methods for increasing the expression of genes involved in fatty acid oxidation in a cell comprising exposure of cells to a CST or its equivalent in an amount sufficient to increase the expression of genes involved in fatty acid oxidation.

The invention also provides methods for increasing fatty acid oxidation lipid flux from adipose tissue toward liver for catabolism in a subject comprising administering CST or its equivalent to a subject in an amount sufficient to increase fatty acid oxidation lipid flux from adipose tissue toward liver for catabolism.

The invention also provides methods for improving hepatic insulin clearance by administration of CST or its equivalent in insulin resistant subjects.

BRIEF DESCRIPTION OF THE FIGURES

FIG. 10. Alignment of the CST region of CHGA from different species and homologous proteins with partial amino acid sequence identity. (Bovine=SEQ ID NO:46; Human 1=SEQ ID NO:47; Human 2=SEQ ID NO: 48; Porcine=SEQ ID NO:49; Rat=SEQ ID NO:50; Mouse=SEQ ID NO:51; 8FAB=SEQ ID NO:52; 1PKM=SEQ ID NO:53; and 2IG2=SEQ ID NO:54).

DETAILED DESCRIPTION OF THE INVENTION

Figure 1:
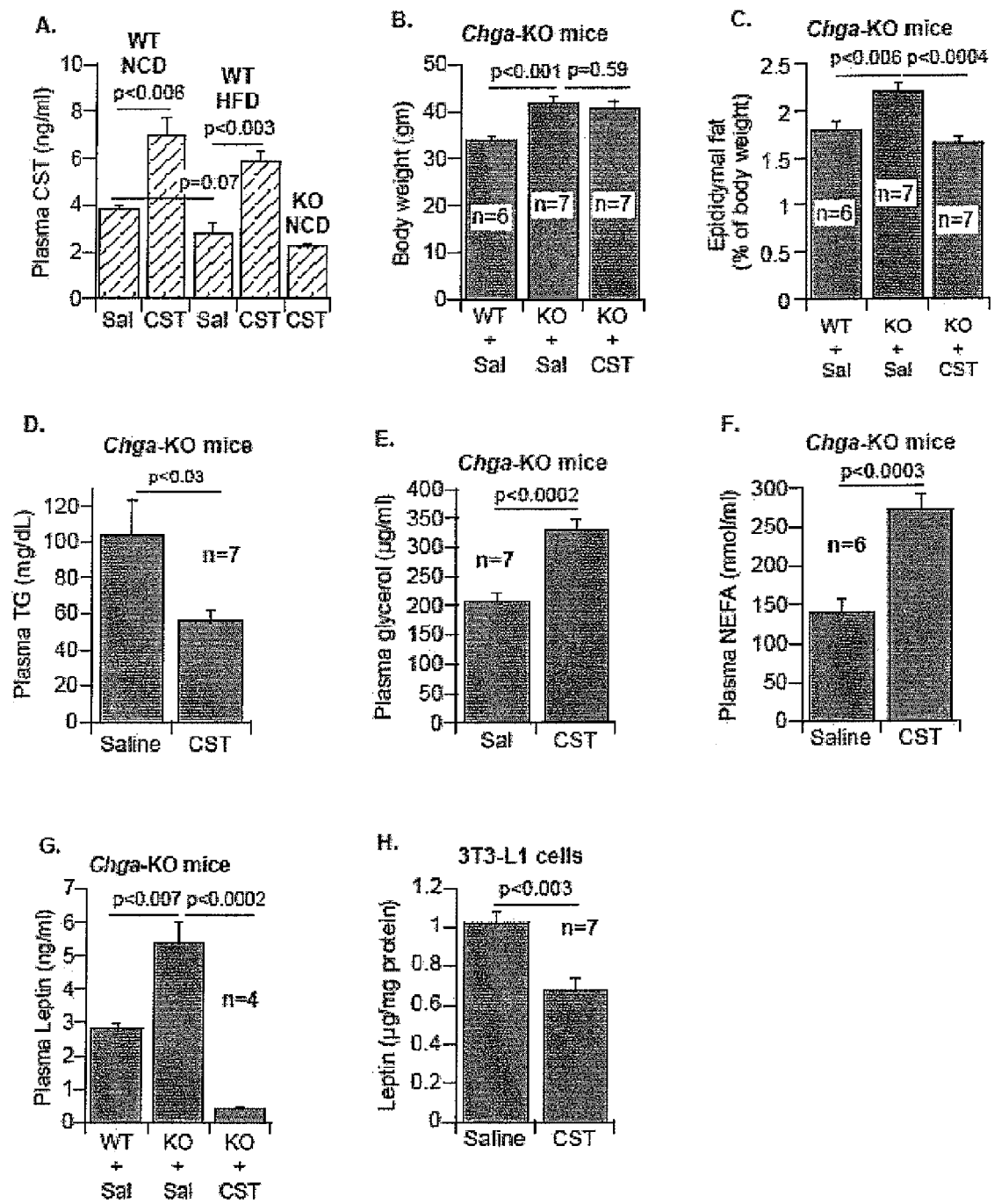
FIG. 1. Plasma parameters of wild-type (WT) and Chga-KO mice treated with saline or CST. (A) Plasma CST from saline or CST (5 μg/g BW, i.p./day) treated WT mice (28 week old) on normal chow (NCD) and high fat diet (60% fat for 16 weeks) as well as from Chga-KO mice (28 week old) on NCD. Body weights (B) and epididymal fat pad size normalized to body weight (C) in 28 week old WT and Chga-KO mice treated with saline or CST for 12 days. Plasma triglyceride (TG) (D), glycerol (E), non-esterified fatty acids (NEFA) (F), and leptin (G) in 28 week old WT and Chga-KO mice after treatment with saline or CST for 12 days. (H) Leptin in adipocyte culture media after treatment with saline or CST.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

The phrase "pharmaceutically acceptable carrier" refers to any carrier known to those skilled in the art to be suitable for the particular mode of administration. In addition, the CST or equivalents thereof may be formulated as the sole pharmaceutically active ingredient in the composition or may be combined with other active ingredients.

I. METHODS OF THE INVENTION

The invention provides methods for treating obesity in a subject in need thereof. In accordance with the practice of the invention, the subject in any of these methods may be overweight, diabetic, leptin deficient, leptin resistant, hyperleptinemic, deficient in PST, deficient in CHGA, insulin resistant, hyperinsulinemic, exhibits low plasma levels of naturally occurring CST, or can benefit from treating obesity.

The method comprises administering an effective amount of a CST or an equivalent thereof to the subject so as to maintain an effective amount of circulating CST in the subject to promote lipolysis and oxidation of released fatty acids (for example, in liver and/or adipose tissue), thereby reducing adipose tissue mass and hence treating obesity in the afflicted subject. In one embodiment of the invention, the CST or its equivalent is a ligand for the leptin receptor (Ob-R). Further, in an embodiment of the invention, CST or its equivalent is an agonist with leptin like activity. Additionally, in another embodiment, the CST or its equivalent may compete with leptin for binding to the Ob-R. In a further embodiment, the CST or its equivalent binds the Ob-R through Ob-R's immunoglobulin (IG)-like domain. Additional embodiments of CSTs and equivalents thereof is provided in the section hereinafter entitled "II. Compositions of the invention."

In one embodiment of the invention the overweight subject may be obese. The subject's obesity may be diet induced obesity. Further, the obesity may be associated with a condition or disorder related to reduced circulating CST or decreased sensitivity of a β-ADR or a combination thereof.

It is understood that lipolysis may produce increased levels of plasma glycerol and non-esterified fatty acids (NEFAs) and decreased levels of plasma triglycerides. Additionally, it is further understood that the oxidation of released fatty acids includes production of carbon dioxide.

In accordance with the practice of the invention, the CST or its equivalent may be administered by an enteral route, buccal route, intra-peritoneal route, inhalation route, intravenous route, subcutaneous route or intramuscular route. Further, in one embodiment, administration of the CST or its equivalent may result in reduced food intake and/or enhanced hypothalamic leptin response.

In accordance with the practice of the invention, CST may be administered as part of an acute CST treatment or a chronic CST treatment.

The invention also provides methods for reversing leptin resistance in the brain or peripheral tissue of a subject. The method comprises administering an effective amount of a CST or an equivalent thereof to the subject with leptin resistance so as to maintain an effective amount of circulating naturally occurring CST in the subject to decrease hyperleptinemia or minimize chronic leptin overexposure in the subject thereby restoring leptin sensitivity in the brain or peripheral tissue of the subject.

For example, leptin resistance includes the desensitization of Ob-R due to hyperleptinemia. Further, desensitization of Ob-R may include a decrease in phosphorylation of AMPK and/or STAT3, following, e.g., acute leptin treatment. Also, decrease hyperleptinemia includes lowering leptin levels in the brain. Further, restoring leptin sensitivity may comprise restoring leptin's ability to signal through its receptor, Ob-R to stimulate phosphorylation of AMPK and/or STAT3.

Further the invention provides methods for inhibiting leptin production in a subject. The method comprises administering an effective amount of a CST or an equivalent thereof to the subject so as to maintain an effective amount of circulating CST in the subject thereby inhibiting leptin production.

Additionally, the invention provides methods for decreasing triglyceride levels in the plasma of a subject. The method comprises administering to the subject an effective amount of a CST or an equivalent thereof so as to maintain an amount of circulating CST to elicit decrease in plasma triglyceride levels.

The invention also provides methods for increasing the therapeutic effectiveness of an anti-diabetic drug in a subject. The method comprises administering to the subject an effective amount of a CST or an equivalent thereof so as to promote lipolysis and/or reduce hypertension thereby reducing the undesirable side effects associated with the anti-diabetic drug. For example, the undesirable side effect may include weight gain or cardiovascular risks.

In accordance with the practice of the invention, the CST or the equivalent thereof may be administered before, concurrently, or after administration of the antidiabetic drug.

Examples of antidiabetic drugs include but are not limited to a biguanides class of antidiabetic drugs, meglitinides class of antidiabetic drug, sulfonylureas class of antidiabetic drug or thiazolidinedione class of antidiabetic drug. Rosiglitazone or pioglitazone are examples of thiazolidinedione class of antidiabetic drugs.

Further, the invention provides methods for enhancing lipolysis in a subject comprising administering to the subject an effective amount of a CST or an equivalent thereof. Optionally, the method further comprises administering an effective amount of a CST or an equivalent thereof in combination with an agonist for a β-ADR or an antagonist for an α-ADR in combination with an agonist for a β-ADR to the subject thereby increasing lipolysis in the subject.

Examples of antagonists for the α-ADR includes but are not limited to phentolamine (also known as 3-[(4,5-dihydro-1H-imidazol-2-ylmethyl)(4-methylphenyl)amino]phenol), Prazosin (also known as 2-[4-(2-furoyl)piperazin-1-yl]-6,7-dimethoxyquinazolin-4-amine)(an α1-ADR blocker), or Idazoxan (also known as (±)-2-(2,3-dihydro-1,4-benzodioxin-2-yl)-4,5-dihydro-1H-imidazole) and Yohimbine (also known as 17α-hydroxy-yohimban-16α-carboxylic acid methyl ester)(α2-ADR blockers).

Examples of agonists for β-ADR includes but are not limited to iso-proterenol (also known as (RS)-4-[1-hydroxy-2-(isopropylamino)ethyl]benzene-1,2-diol), Dobutamine (also known as (RS)-4-(2-{[4-(4-hydroxyphenyl)butan-2-yl]amino}ethyl)benzene-1,2-diol) (a β1-ADR agonist), or Clenbuterol (also known as (RS)-1-(4-Amino-3,5-dichlorophenyl)-2-(tert-butylamino)ethanol) (a β2-ADR agonist).

The invention further provides methods for increasing the expression of genes involved in fatty acid oxidation in a cell. The cell may be derived from liver, muscle or adipose tissue. The method comprises contacting the cell with a CST or the equivalent thereof in an amount sufficient to increase the expression of the genes involved in fatty acid oxidation. Examples of the genes involved in fatty acid oxidation includes but are not limited to Pparα, Acox, Ucp2 and Cpt1α.

The invention additionally provides methods for increasing fatty acid oxidation and/or lipid flux from adipose tissue toward liver for catabolism in a subject. The method comprises administering a CST or an equivalent thereof to the subject in an amount sufficient to increase fatty acid oxidation and/or lipid flux from adipose tissue toward liver for catabolism.

Also, the invention provides methods for increasing lipolysis in adipose tissue and fatty acid uptake and oxidation in the liver of a subject. The method comprises administering a CST or an equivalent thereof in an amount sufficient to increase the lipolysis in the adipose tissue and fatty acid uptake and oxidation in the liver.

The invention yet further provides methods for reducing circulating insulin levels in insulin resistant subjects thus minimizing chronic exposure to persistently high levels of insulin which may cause desensitization of insulin action. In one embodiment, the method comprises administering a CST or an equivalent thereof in the subject thereby reducing circulating insulin levels through improvement of hepatic insulin clearance.

The invention also provides methods for treating diabetes by any of the methods described herein. In one embodiment, the method comprises administering a CST or an equivalent thereof to a subject in an amount sufficient to raise circulating insulin levels in the subject thereby treating the subject suffering from diabetes.

Further, the invention provides methods for stimulating expression of a transporter which mediates the cellular uptake of long-chain fatty acids in the subject. The method comprises administering a CST or an equivalent thereof to the subject in an amount sufficient to promote the expression of the transporter which mediates the cellular uptake of long-chain fatty acids. In one embodiment, the transporter which mediates the cellular uptake of long-chain fatty acids is Cd36.

Additionally, the invention provides methods for stimulating the expression of a lipogenic gene in a subject. The method comprises administering a CST or an equivalent thereof to the subject in an amount sufficient to promote the expression of the lipogenic gene. For example, the lipogenic gene may be glycerol-3-phosphate acyltransferase-4 (Gpat4).

Further the invention provides methods for attenuating phospholipase C (PLC) activation by an α-ADR agonists and/or epinephrine in a subject. The method comprises administering a CST or an equivalent thereof to the subject in an amount sufficient to attenuate PLC activation by an α-ADR agonist and/or epinephrine. For example, the α-ADR1 agonist is phenylephrine (also known as (R)-3-[-1-hydroxy-2-(methylamino)ethyl]phenol), methoxamine (also known as 2-amino-1-(2,5-dimethoxyphenyl)propan-1-ol) or oxymetazoline (also known as 3-(4,5-dihydro-1H-imidazol-2-ylmethyl)-2,4-dimethyl-6-tert-setylphenol).

Additionally, the invention provides methods for enhancing or potentiating the lipolytic effects of a β-ADR agonist in adipocytes. The method comprises contacting adipocytes with an α-ADR antagonist and a CST or an equivalent thereof thereby enhancing or potentiating the lipolytic effects of a β-ADR agonist in adipocytes. For example, the β-ADR agonist may be isoproterenol (also known as (RS)-4-[1-hydroxy-2-(isopropylamino)ethyl]benzene-1,2-diol), Nadolol (also known as (2R,3S)-5-{[(2R)-3-(tert-butylamino)-2-hydroxypropyl]oxy}-1,2,3,4-tetrahydronaphthalene-2,3-diol) and propranolol (also known as (RS)-1-(1-methylethylamino)-3-(1-naphthyloxy)propan-2-ol). Further, in one embodiment the α-ADR antagonist may be phentolamine (also known as 3-[(4,5-dihydro-1H-imidazol-2-ylmethyl)(4-methylphenyl)amino]phenol), Prazosin (also known as 2-[4-(2-furoyl)piperazin-1-yl]-6,7-dimethoxyquinazolin-4-amine) or Terazosin (also known as 6,7-dimethoxy-2-[4-(tetrahydrofuran-2-ylcarbonyl)piperazin-1-yl]quinazolin-4-amine).

The invention also provides methods for suppressing α-ADR signaling in a subject. The method comprises administering a CST or an equivalent thereof to the subject in an amount sufficient to suppress α-ADR signaling.

Additionally, the invention provides methods for reducing food intake in a leptin deficient subject. The method comprises administering a CST or an equivalent thereof in a suitable amount so as to affect the central nervous system (CNS) of the subject thereby reducing food intake in the leptin-deficient subject. In one embodiment the administration of CST is chronic.

The invention further provides methods for achieving synergistic activation of lipolysis and/or fatty acid oxidation in a subject. In one embodiment the subject is obese and/or the subject may exhibit insulin resistance. The method comprises administering a CST or an equivalent thereof to the subject in an amount sufficient to promote synergistic activation of lipolysis. Merely by way of example, the lipolysis and/or fatty acid oxidation may occur in the adipose tissue of the subject.

Also the invention provides methods for achieving synergistic activation of STAT3 and/or AMPK in a subject. The method comprises administering a CST or an equivalent thereof to the subject to promote synergistic phosphorylation of STAT3 and/or AMPK. In accordance with the practice of the invention, the synergistic activation of STAT3 and/or AMPK may occur in the adipose tissue. Further, the subject may be obese or may exhibit insulin resistance.

The invention further provides methods for reducing insulin levels in a diabetic or insulin resistant subject. The method comprises administering an effective amount of a CST or its equivalent to the subject so as to maintain an effective amount of circulating CST thereby reducing insulin levels in the diabetic or insulin resistant subject. In one embodiment, the invention provides treating diabetes using this method.

Further still, the invention provides methods for restoring or increasing insulin sensitivity in a diabetic or an insulin resistant subject comprising administering an effective amount of a CST or its equivalent to the subject. By doing so, an effective amount of circulating CST or its equivalent in the subject may restore or increase insulin sensitivity in the diabetic or insulin resistant subject. In one embodiment, the invention provides treating diabetes using this method.

The invention additionally provides methods for normalizing plasma insulin concentration in a subject afflicted with hyperinsulinemia. The method comprises administering an amount of a CST or its equivalent so as to maintain an effective amount of circulating CST or its equivalent in the subject. Thereby, the insulin level in the subject will reduce and normalize the plasma insulin concentration in the subject.

The invention further provides methods for enhancing insulin clearance in a hyperinsulinemic subject. The method comprises administering amount of a CST or its equivalent to maintain an effective amount of circulating CST or its equivalent in the subject thereby enhancing insulin clearance by the liver of the hyperinsulinemic subject.

Also, the invention further provides methods for improving glucose tolerance and insulin clearance in a diabetic subject. The method comprises administering an amount of a CST or its equivalent so as to maintain an effective amount of circulating CST in the subject thereby improving glucose tolerance and insulin clearance.

Further, the invention provides methods for improving glucose tolerance in diabetic subjects. The method comprises administering an amount of CST or its equivalent so as to maintain an effective amount of circulating CST in the subject period. In one embodiment, improving glucose tolerance results in improving the blood pressure of the diabetic patient.

In accordance with the practice of this invention, the subject of the gene therapy may be a human, equine, porcine, bovine, murine, canine, feline, or avian subject. Other mammals are also included in this invention. The invention provides methods for treating obesity in a subject in need thereof. In accordance with the practice of the invention, the subject in any of these methods may be overweight, diabetic, leptin deficient, leptin resistant, hyperleptinemic, deficient in PST, deficient in CHGA, insulin resistant, hyperinsulinemic, exhibits low plasma levels of naturally occurring CST, or can benefit from treating obesity.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on $mg/m^2$ of surface area is described by Freireich, E. J., et al. Cancer Chemother., Rep. 50 (4): 219-244 (1966). Adjustments in the dosage regimen may be made to optimize the desired response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve treatment may be further modified with schedule optimization.

II. COMPOSITIONS OF THE INVENTION

Compositions herein comprise one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

The invention provides compositions and oral or injectable dosage forms comprising a CST or CST equivalent and a carrier.

In one embodiment, a CST is a peptide having the amino acid sequence amino-$S_{352}$SMKLSFRARAYGFRGPGPQL$_{372}$-carboxyl (SEQ ID NO:1) (also referred to herein as a human CST sequence (CHGA$_{352-372}$). The invention provides CST equivalents, e.g., a variant of a human CST sequence. Examples of such CST equivalents include but are not limited to Amino-$S_{352}$SMKLSFRARAYS$_{364}$FRGPGPQL$_{372}$-carboxyl (SEQ ID NO:2) (also referred to herein as a human Gly364Ser variant sequence (CHGA$_{352-372}$), amino-$S_{352}$SMKLSFRARAYGFRV$_{367}$PGPQL$_{372}$ (SEQ ID NO:3) (also referred to herein as a human Gly367Val variant sequence (CHGA$_{352-372}$), and amino-$S_{352}$SMKLSFRARAYGFRGPGL$_{370}$QL$_{372}$-carboxy (SEQ ID NO: 4) (referred to herein as a human Pro370Leu variant sequence (CHGA$_{352-372}$).

Additional embodiments of CST molecules include but are not limited to amino-$R_{344}$-SMRLSFRARGYGFRGPGLQL$_{364}$-carboxyl (SEQ ID NO:5) (also referred to herein as a bovine CST sequence (CHGA$_{344-364}$), amino-$R_{343}$SMRLSFRAPAYGFRGPGLQL$_{363}$-carboxyl (SEQ ID NO:6) (porcine CST sequence (CHGA$_{343-363}$)), amino-$R_{367}$SMRLSFRARGYGFRDPGLQL$_{387}$-amino (SEQ ID NO:7) (also referred to herein as a rat CST sequence (CHGA$_{367-387}$)), amino-$R_{364}$SMRLSFRTRGYGFRDPGLQL$_{384}$-carboxyl (SEQ ID NO:8) (also referred to herein as a mouse CST sequence (CHGA$_{364-384}$)), amino-$R_{368}$SMKLSFRARAYGFRGPGPQL$_{388}$-carboxyl (SEQ ID NO:9) (also referred to herein as a rhesus monkey CST sequence (CHGA$_{368-388}$)), amino-$S_{370}$SMKLPFRAR-AYGFRGPGPQL$_{390}$-carboxyl (SEQ ID NO:10) (also referred to herein as a Sumatran orangutan CST sequence (CHGA$_{370-390}$)), amino-$R_{361}$SMKLSFRARAYGF-RGPGLQL$_{381}$-carboxyl (SEQ ID NO:11) (also referred to herein as a horse CST sequence (CHGA$_{361-381}$)), amino-$H_{372}$SMKLSFRARAYGFGGPGPQL$_{392}$-carboxyl (SEQ ID NO:12) (also referred to herein as a squirrel monkey CST sequence (CHGA$_{372-392}$)), amino-$S_{462}$SMKLSFRAR-AYDFRGPGLQL$_{482}$-carboxyl (SEQ ID NO:13) (also referred to herein as a cat CST sequence (CHGA$_{462-482}$)), amino-$H_{370}$SMKLSFQARAYDFRGPGPQL$_{390}$-carboxyl (SEQ ID NO:14) (also referred to herein as a marmoset CST sequence (CHGA$_{370-390}$)), amino-$R_{330}$SMKLSFRAR-AYDFRGPGLQL$_{350}$-carboxyl (SEQ ID NO:15) (also referred to herein as a panda bear CST sequence (CHGA$_{330-350}$ or CHGA$_{361-381}$)), amino-$R_{353}$SMKLSFRARAYGFRDPRPQL$_{373}$-carboxyl (SEQ ID NO:16) (also referred to herein as a Chinese hamster CST sequence (CHGA$_{353-373}$)), amino-$R_{361}$SMKLSF-RAPAYGFRGPGLQL$_{381}$-carboxyl (SEQ ID NO:17) (also referred to herein as a wild boar CST sequence (CHGA$_{361-381}$)), amino-$R_{363}$SMKLSFRARAYDFRGPG$_{383}$ (SEQ ID NO:18) (also referred to herein as a dog CST sequence (CHGA$_{363-383}$)), amino-$R_{415}$SMKLSFRA-QAYGFPGPEPQL$_{435}$-carboxyl (SEQ ID NO:19) (also referred to herein as a guinea pig CST sequence (CHGA$_{415-435}$)), amino-$R_{354}$SMKLSFRARGYGF-GAPGPQL$_{374}$-carboxyl (SEQ ID NO:20) (also referred to herein as a myotis CST sequence (CHGA$_{354-374}$)), amino-$R_{362}$SMKLSLRARSYGFGGPGPQL$_{382}$-carboxyl (SEQ ID NO:21) (also referred to herein as a African bush elephant CST sequence (CHGA$_{362-382}$)), amino-$R_{382}$SMKLSL-QTRAYDFRGPGPQL$_{402}$-carboxyl (SEQ ID NO:22) (also referred to herein as a small-eared galago CST sequence (CHGA$_{382-402}$)), amino-$R_{283}$SMKLSFQAPAYD-FRGSGPQL$_{303}$-carboxyl (SEQ ID NO:23) (also referred to herein as a mole rat CST sequence (CHGA$_{283-303}$)), amino-$R_{318}$SMKLSFQSRAYGFRGPRHQL$_{338}$-carboxyl (SEQ ID NO:24) (also referred to herein as a Chinese tree shrew CST sequence (CHGA$_{318-338}$)), and amino-$R_{358}$AMKLSFRARGYDFSGPGLQL$_{378}$-carboxyl (SEQ ID NO:25) (also referred to herein as a killer whale CST sequence (CHGA$_{358-378}$)).

For example, FIG. 10 is an alignment of the CST region of CHGA with homologous regions of proteins with partial amino acid sequence identity and known three-dimensional structure, as determined by x-ray crystallography: 8FAB (a human myeloma immunoglobulin). 1PKM (cat muscle pyruvate kinase), and 2IG2 (a monoclonal human immunoglobulin). Columns in bold contain residues found not only in the majority of CST regions but also in at least one of the homologous proteins. In the FASTA alignment, the gap penalty was −12/−2. Human CHGA sequence (1): Konecki, D. S., U. M. Benedum, H. H. Gerdes, and W. B. Huttner. 1987. The primary structure of human chromogranin A and pancreastatin. J. Biol. Chem. 262:17026-17030. Human chromogranin A sequence (2): Helman, L. J., T. G. Ahn, M. A. Levine, A. Allison, P. S. Cohen, M. J. Cooper, D. V. Cohn, M. A. Israel. 1988. Molecular cloning and primary structure of human chromogranin A (secretory protein I) cDNA. J. Biol. Chem. 263: 11559-11563. For other chromogranin A sequences in the CST region, see Mahata et al., 1997.

CST's primary structure bore significant (29-35.5% identity, general alignment score 44-57) sequence homology to fragment sequences within three homologs of known 3-dimensional structures, based on solved X-ray crystals: 8FAB, 1PKM, and 2IG2 (FIG. 10; Tsigelny I., S. K. Mahata, L. Taupenot, N. E. Preece, M. Mahata, I. Khan, R. J. Parmer, D. T. O'Connor. Mechanism of action of chromogranin A on catecholamine release: molecular modeling of the catestatin region reveals a β-strand/loop/β-strand structure secured by hydrophobic interactions and predictive of activity Regulatory Peptides 1998; 77:43-53). Each of these sequences exists in nature as a β-strand/loop/β-strand structure, stabilized by hydrophobic interactions between the β-strands. The catestatin loop contains three Arg residues, whose electropositive side chains form the terminus of the structure, and give rise to substantial uncompensated charge asymmetry in the molecule. A hydrophobic moment plot revealed that catestatin is the only segment of CHGA predicted to contain amphiphilic β-strand. Circular dichroism in the far ultraviolet showed substantial (63%) β-sheet structure, especially in a hydrophobic environment. Alanine-substitution mutants of CST established a crucial role for the three central arginine residues in the loop (Arg$^{351}$, Arg$^{353}$, and Arg$^{358}$), though not for two arginine residues in the strand region toward the amino-terminus. [$^{125}$I]CST bound to Torpedo membranes at a site other than the nicotinic agonist binding site. When the catestatin structure was 'docked' with the extracellular domain of the Torpedo nicotinic cholinergic receptor, it interacted principally with the β and δ subunits, in a relatively hydrophobic region of the cation pore extracellular orifice, and the complex of ligand and receptor largely occluded the cation pore, providing a structural basis for the non-competitive nicotinic cholinergic antagonist properties of the peptide.

Merely as an example, a portion of CHGA corresponding to the biologically active CST (bovine $CHGA_{344-364}$) is framed by a loop joining two anti-parallel β-sheets to display the orientation of the strands about the connecting loop in the modeled region, bovine $CHGA_{342-370}$ ($Pro^{342} \rightarrow Pro^{370}$; PDRSMRLSFRARGYGFRGPGLQLR-RGWRP (SEQ ID NO:26)).

The CST amino acid sequences above may be mutated so as to generate CST equivalents. For example, in any of the CST polypeptides above the amino acid at any one or more position(s) may be exchanged with an amino acid at the same position(s) from any of the peptides above.

Further, in an embodiment of the invention the equivalent of the CST comprises a peptide fragment or derivative of any of: amino-$S_{352}$SMKLSFRARAYGFRGPGPQL$_{372}$-carboxyl (SEQ ID NO:1) (also referred to herein as a human CST sequence ($CHGA_{352-372}$); Amino-$S_{352}$SMKLSFRARAYS$_{364}$FRGPGPQL$_{372}$-carboxyl (SEQ ID NO:2) (also referred to herein as a human Gly364Ser variant sequence ($CHGA_{352-372}$); amino-$S_{352}$SMKLSFRARAYGFRV$_{367}$PGPQL$_{372}$ (SEQ ID NO:3) (also referred to herein as a human Gly367Val variant sequence ($CHGA_{352-372}$); amino-$S_{352}$SMKLSFRARAY-GFRGPGL$_{370}$QL$_{372}$-carboxy (SEQ ID NO:4) (referred to herein as a human Pro370Leu variant sequence ($CHGA_{352-372}$); amino-$R_{344}$-SMRLSFRARGYGFRG-PGLQL$_{364}$-carboxyl (SEQ ID NO:5) (also referred to herein as a bovine CST sequence ($CHGA_{344-364}$), amino-$R_{343}$SMRLSFRAPAYGFRGPGLQL$_{363}$-carboxyl (SEQ ID NO:6) (porcine CST sequence ($CHGA_{343-363}$), amino-$R_{367}$SMRLSFRARGYGFRDPGLQL$_{387}$-amino (SEQ ID NO:7) (also referred to herein as a rat CST sequence ($CHGA_{367-387}$)), amino-$R_{364}$SMRLSFRTRGYGFRD-PGLQL$_{384}$-carboxyl (SEQ ID NO:8) (also referred to herein as a mouse CST sequence ($CHGA_{364-384}$)), amino-$R_{368}$SMKLSFRARAYGFRGPGPQL$_{388}$-carboxyl (SEQ ID NO:9) (also referred to herein as a rhesus monkey CST sequence ($CHGA_{368-388}$)), amino-$S_{370}$SMKLPFRAR-AYGFRGPGPQL$_{390}$-carboxyl (SEQ ID NO:10) (also referred to herein as a Sumatran orangutan CST sequence ($CHGA_{370-390}$)), amino-$R_{361}$SMKLSFRARAYGF-RGPGLQL$_{381}$-carboxyl (SEQ ID NO:11) (also referred to herein as a horse CST sequence ($CHGA_{361-381}$)), amino-$R_{352}$SMRLSFRARAYGFRGPGPQL$_{372}$-carboxyl (SEQ ID NO:55) (also referred to herein as a bovine CST sequence variant 1 ($CHGA_{352-372}$)), amino-$R_{370}$SMRLSFRARG-YGFRGPGPQL$_{390}$-carboxyl (SEQ ID NO:56) (also referred to herein as a bovine CST sequence variant 2 ($CHGA_{370-390}$)), amino-$R_{384}$SMKLSFRTRAYGFR-DPGPQL$_{404}$ (SEQ ID NO:57) (also referred to herein as a mouse CST sequence variant ($CHGA_{384-404}$)), amino-$H_{372}$SMKLSFRARAYGFGGPGPQL$_{392}$-carboxyl (SEQ ID NO:12) (also referred to herein as a squirrel monkey CST sequence ($CHGA_{372-392}$)), amino-$S_{462}$SMKLSFRARAY-DFRGPGLQL$_{482}$-carboxyl (SEQ ID NO:13) (also referred to herein as a cat CST sequence ($CHGA_{462-482}$)), amino-$H_{370}$SMKLSFQARAYDFRGPGPQL$_{390}$-carboxyl (SEQ ID NO:14) (also referred to herein as a marmoset CST sequence ($CHGA_{370-390}$)), amino-$R_{330}$SMKLSFRARAYDFRGP-GLQL$_{350}$-carboxyl (SEQ ID NO:15) (also referred to herein as a panda bear CST sequence ($CHGA_{330-350}$ or $CHGA_{361-381}$)), amino-$R_{353}$SMKLSFRARAYGFR-DPRPQL$_{373}$-carboxyl (SEQ ID NO:16) (also referred to herein as a Chinese hamster CST sequence ($CHGA_{353-373}$)), amino-$R_{361}$SMKLSFRAPAYGFRGPGLQL$_{386}$-carboxyl (SEQ ID NO:17) (also referred to herein as a wild boar CST sequence ($CHGA_{361-381}$)), amino-$R_{363}$SMKLSFRAR-AYDFRGPG$_{383}$ (SEQ ID NO:18) (also referred to herein as a dog CST sequence ($CHGA_{363-383}$)), amino-$R_{415}$SMKLSFRAQAYGFPGPEPQL$_{435}$-carboxyl (SEQ ID NO:19) (also referred to herein as a guinea pig CST sequence ($CHGA_{415-435}$)), amino-$R_{354}$SMKLSFRA-RGYGFGAPGPQL$_{374}$-carboxyl (SEQ ID NO:20) (also referred to herein as a myotis CST sequence ($CHGA_{354-374}$)), amino-$R_{362}$SMKLSLRARSYGFG-GPGPQL$_{382}$-carboxyl (SEQ ID NO:21) (also referred to herein as a African bush elephant CST sequence ($CHGA_{362-382}$)), amino-$R_{382}$SMKLSLQTRAYDFRG-PGPQL$_{402}$-carboxyl (SEQ ID NO:22) (also referred to herein as a small-eared galago CST sequence ($CHGA_{382-402}$)), amino-$R_{283}$SMKLSFQAPAYDFR-GSGPQL$_{303}$-carboxyl (SEQ ID NO:23) (also referred to herein as a mole rat CST sequence ($CHGA_{283-303}$)), amino-$R_{318}$SMKLSFQSRAYGFRGPRHQL$_{338}$-carboxyl (SEQ ID NO:24) (also referred to herein as a Chinese tree shrew CST sequence ($CHGA_{318-338}$)), and amino-$R_{358}$AMKLS-FRARGYDFSGPGLQL$_{378}$-carboxyl (SEQ ID NO:25) (also referred to herein as a killer whale CST sequence ($CHGA_{358-378}$)).

Additionally, in one embodiment the equivalent of a CST is a macromolecule that competes with the binding of a peptide having a sequence shown below to a nicotinic cholinergic receptor, leptin receptor and/or adrenergic receptor, inhibits release of catecholamines and/or promotes lipolysis and/or oxidation of released fatty acids in both liver and adipose tissue, wherein the peptide to which the macromolecule will compete includes a portion or derivative of any of the following sequences: amino-$S_{352}$SMKLSFRARAYGFRGPGPQL$_{372}$-carboxyl (SEQ ID NO:1) (also referred to herein as a human CST sequence ($CHGA_{352-372}$); Amino-$S_{352}$SMKLSFRARAYS$_{364}$ FRGPGPQL$_{372}$-carboxyl (SEQ ID NO:2) (also referred to herein as a human Gly364Ser variant sequence ($CHGA_{352-372}$); amino-$S_{352}$SMKLSFRARAYGFRV$_{367}$ PGPQL$_{372}$ (SEQ ID NO:3) (also referred to herein as a human Gly367Val variant sequence ($CHGA_{352-372}$); amino-$S_{352}$SMKLSFRARAYGFRGPGL$_{370}$QL$_{372}$-carboxy (SEQ ID NO:4) (referred to herein as a human Pro370Leu variant sequence ($CHGA_{352-372}$); amino-$R_{344}$-SMRLSFRARGYG-FRGPGLQL$_{364}$-carboxyl (SEQ ID NO:5) (also referred to herein as a bovine CST sequence ($CHGA_{344-364}$), amino-$R_{343}$SMRLSFRAPAYGFRGPGLQL$_{363}$-carboxyl (SEQ ID NO:6) (porcine CST sequence ($CHGA_{343-363}$), amino-$R_{367}$SMRLSFRARGYGFRDPGLQL$_{387}$-amino (SEQ ID NO:7) (also referred to herein as a rat CST sequence ($CHGA_{367-387}$)), amino-$R_{364}$SMRLSFRTRGYGFRDP-GLQL$_{384}$-carboxyl (SEQ ID NO:8) (also referred to herein as a mouse CST sequence ($CHGA_{364-384}$)), amino-$R_{368}$SMKLSFRARAYGFRGPGPQL$_{388}$-carboxyl (SEQ ID NO:9) (also referred to herein as a rhesus monkey CST sequence ($CHGA_{368-388}$)), amino-$S_{370}$SMKLPFRARA-YGFRGPGPQL$_{390}$-carboxyl (SEQ ID NO:10) (also referred to herein as a Sumatran orangutan CST sequence ($CHGA_{370-390}$)), amino-$R_{361}$SMKLSFRARAYGFRG-PGLQL$_{381}$-carboxyl (SEQ ID NO:11) (also referred to herein as a horse CST sequence ($CHGA_{361-381}$)), amino-$R_{384}$SMKLSFRTRAYGFRDPGPQL$_{404}$ (SEQ ID NO:57) (also referred to herein as a mouse CST sequence variant ($CHGA_{384-404}$)), amino-$H_{372}$SMKLSFRARAYG-FGGPGPQL$_{392}$-carboxyl (SEQ ID NO:12) (also referred to herein as a squirrel monkey CST sequence ($CHGA_{372-392}$)), amino-$S_{462}$SMKLSFRARAYDFRGPGLQL$_{482}$-carboxyl (SEQ ID NO:13) (also referred to herein as a cat CST sequence (CHGA$_{462-482}$)), amino-H$_{370}$SMKLSFQARA-YDFRGPGPQL$_{390}$-carboxyl (SEQ ID NO:14) (also referred to herein as a marmoset CST sequence (CHGA$_{370-390}$)), amino-R$_{330}$SMKLSFRARAYDFRGPGLQL$_{350}$-carboxyl (SEQ ID NO:15) (also referred to herein as a panda bear CST sequence (CHGA$_{330-350}$ or CHGA$_{361-381}$)), amino-R$_{353}$SMKLSFRARAYGFRDPRPQL$_{373}$-carboxyl (SEQ ID NO:16) (also referred to herein as a Chinese hamster CST sequence (CHGA$_{353-373}$)), amino-R$_{361}$SMKLSFRAPAY-GFRGPGLQL$_{386}$-carboxyl (SEQ ID NO:17) (also referred to herein as a wild boar CST sequence (CHGA$_{361-381}$)), amino-R$_{363}$SMKLSFRARAYDFRGPG$_{383}$ (SEQ ID NO:18) (also referred to herein as a dog CST sequence (CHGA$_{363-383}$)), amino-R$_{415}$SMKLSFRAQAYGFPG-PEPQL$_{435}$-carboxyl (SEQ ID NO:19) (also referred to herein as a guinea pig CST sequence (CHGA$_{415-435}$)), amino-R$_{354}$SMKLSFRARGYGFGAPGPQL$_{374}$-carboxyl (SEQ ID NO:20) (also referred to herein as a myotis CST sequence (CHGA$_{354-374}$)), amino-R$_{362}$SMKLSLRARS-YGFGGPGPQL$_{382}$-carboxyl (SEQ ID NO:21) (also referred to herein as a African bush elephant CST sequence (CHGA$_{362-382}$)), amino-R$_{382}$SMKLSLQTRAYDFRGP-GPQL$_{402}$-carboxyl (SEQ ID NO:22) (also referred to herein as a small-eared galago CST sequence (CHGA$_{382-402}$)), amino-R$_{283}$SMKLSFQAPAYDFRGSGPQL$_{303}$-carboxyl (SEQ ID NO:23) (also referred to herein as a mole rat CST sequence (CHGA$_{283-303}$)), amino-R$_{318}$SMKLSFQSRAY-GFRGPRHQL$_{338}$-carboxyl (SEQ ID NO:24) (also referred to herein as a Chinese tree shrew CST sequence (CHGA$_{318-338}$)), and amino-R$_{358}$AMKLSFRARGYDFS-GPGLQL$_{378}$-carboxyl (SEQ ID NO:25) (also referred to herein as a killer whale CST sequence (CHGA$_{358-378}$)).

A retro-inverso (R-I) version of human CST or a human CST equivalent is included herein with inversion of chirality (L→D amino acids) and also reversal of sequence (carboxyl→amino) using all D-amino acid monomers and retroversion of the amino acid sequence: amino→carboxyl becoming carboxyl→amino (Chorev M. The partial retro-inverso modification: a road traveled together. *Biopolymers*. 2005; 80:67-84). R-I peptide approach provides a general method for generation of metabolically stable mimics of biologically active peptides for diagnostics and therapeutics.

The retro-inverso (R-I) peptide synthetic modification (Pallai P V, Richman S, Struthers R S, Goodman M. Approaches to the synthesis of retro-inverso peptides. *Int J Pept Protein Res*. 1983; 21:84-92) may involve both inversion of amino acid α-carbon chirality and reversal of peptide bonds (i.e., reversal of primary amino acid sequence) (Pallai P V, Richman S, Struthers R S, Goodman M. Approaches to the synthesis of retro-inverso peptides. *Int J Pept Protein Res*. 1983; 21:84-92; Chorev M, Goodman M. Partially modified retro-inverso peptides. Comparative Curtius rearrangements to prepare 1,1-diaminoalkane derivatives. *Int J Pept Protein Res*. 1983; 21:258-268; Chorev M. The partial retro-inverso modification: a road traveled together. *Biopolymers*. 2005; 80:67-84), with the goal of increasing peptide stability while preserving or reconstituting side-chain orientations. We tested a R-I isomer of human catestatin (hCHGA$_{352-372}$) for its stability, conformation, mechanistic specificity for inhibition of events triggered by nicotinic cholinergic stimulation. R-I catestatin may be impervious to proteolytic digestion, while retaining potency and specificity for nicotinic cholinergic-stimulated catecholamine release.

TABLE 2

Human Catestatin (CHGA$_{352-372}$)
Retro-Inverso Synthetic Sequences

| | |
|---|---|
| Wild-type<br>Amino-SSMKLSFRARAYGFRGPGPQL-carboxyl | SEQ ID NO: 1 |
| Inverso<br>Amino-ssmklsfrarayGfrGpGpql-carboxyl | SEQ ID NO: 1 |
| Retro<br>Amino-LQPGPGRFGYARARFSLKMSS-carboxyl | SEQ ID NO: 27 |
| Retro-inverso<br>Amino-lqpGpGrfGyararfslkmss-carboxyl | SEQ ID NO: 27 |

A human CST (CHGA$_{352-372}$) was synthesized in 4 isomeric versions: wildtype, inverso (all D-amino acids), retro (reversing sequence from amino→carboxyl, to carboxyl→amino), and retro-inverso (R-I, reversing sequence, as well as inverting chirality to all D-amino acids). Upper case=L-amino acid (1-letter code), lower case=D-amino acid (except Gly/G, which has no chirality).

In the R-I peptide, only D-amino acids were used, and the change in chirality was counteracted by reversing the primary amino acid sequence, thus preserving the major side-chain orientations of the peptide, likely underpinning its ability to mimic the parent/W-T isoform. R-I peptides may thus exhibit improved bioavailability because of enhanced stability to proteolysis.

Finally, the CST R-I isomer was effective in rescuing (reducing) the high BP phenotype in Chga−/−mice, a monogenic model of hypertension, and the therapeutic BP effect was sustained for a substantially longer interval (>8 hours during our in vivo study) by the R-I versus W-T isoforms, likely reflecting enhanced stability of the R-I peptide in the circulation.

In one embodiment, the CST equivalent is a retro-inverso CST (RI-CST) peptide comprising D-amino acid in place of L-amino acid except for achiral glycine and an inverse order of the amino-to-carboxyl sequence for any of the following sequences: amino-S$_{352}$SMKLSFRARAYGFRGPGPQL$_{372}$-carboxyl (SEQ ID NO:1) (also referred to herein as a human CST sequence (CHGA$_{352-372}$); Amino-S$_{352}$SMKLSFRARAYS$_{364}$FRGPGPQL$_{372}$-carboxyl (SEQ ID NO:2) (also referred to herein as a human Gly364Ser variant sequence (CHGA$_{352-372}$); amino-S$_{352}$SMKLSFRARAYGFRGPGL$_{370}$QL$_{372}$-carboxy (SEQ ID NO:4) (referred to herein as a human Pro370Leu variant sequence (CHGA$_{352-372}$); amino-R$_{344}$-SMRLSFRARGYG-FRGPGLQL$_{364}$-carboxyl (SEQ ID NO:5) (also referred to herein as a bovine CST sequence (CHGA$_{344-364}$), amino-R$_{343}$SMRLSFRAPAYGFRGPGLQL$_{363}$-carboxyl (SEQ ID NO:6) (porcine CST sequence (CHGA$_{343-363}$), amino-R$_{367}$SMRLSFRARGYGFRDPGLQL$_{387}$-amino (SEQ ID NO:7) (also referred to herein as a rat CST sequence (CHGA$_{367-387}$)), amino-R$_{364}$SMRLSFRTRGYGFRDP-GLQL$_{384}$-carboxyl (SEQ ID NO:8) (also referred to herein as a mouse CST sequence (CHGA$_{364-384}$)), amino-R$_{368}$SMKLSFRARAYGFRGPGPQL$_{388}$-carboxyl (SEQ ID NO:9) (also referred to herein as a rhesus monkey CST sequence (CHGA$_{368-388}$)), amino-S$_{370}$SMKLPFRARAY-GFRGPGPQL$_{390}$-carboxyl (SEQ ID NO:10) (also referred to herein as a Sumatran orangutan CST sequence (CHGA$_{370-390}$)), amino-R$_{361}$SMKLSFRARAYGFR-GPGLQL$_{381}$-carboxyl (SEQ ID NO:11) (also referred to herein as a horse CST sequence (CHGA$_{361-381}$)), amino-R$_{384}$SMKLSFRTRAYGFRDPGPQL$_{404}$ (SEQ ID NO:57)

(also referred to herein as a mouse CST sequence variant (CHGA$_{384-404}$)), amino-H$_{372}$SMKLSFRARAYGFG-GPGPQL$_{392}$-carboxyl (SEQ ID NO:12) (also referred to herein as a squirrel monkey CST sequence (CHGA$_{372-392}$)), amino-S$_{462}$SMKLSFRARAYDFRGPGLQL$_{482}$-carboxyl (SEQ ID NO:13) (also referred to herein as a cat CST sequence (CHGA$_{462-482}$)), amino-H$_{370}$SMKLSFQAR-AYDFRGPGPQL$_{390}$-carboxyl (SEQ ID NO:14) (also referred to herein as a marmoset CST sequence (CHGA$_{370-390}$)), amino-R$_{330}$SMKLSFRARAYDFRG-PGLQL$_{350}$-carboxyl (SEQ ID NO:15) (also referred to herein as a panda bear CST sequence (CHGA$_{330-350}$ or CHGA$_{361-381}$)), amino-R$_{353}$SMKLSFRARAYGFRDPR-PQL$_{373}$-carboxyl (SEQ ID NO:16) (also referred to herein as a Chinese hamster CST sequence (CHGA$_{353-373}$)), amino-R$_{361}$SMKLSFRAPAYGFRGPGLQL$_{381}$-carboxyl (SEQ ID NO:17) (also referred to herein as a wild boar CST sequence (CHGA$_{361-381}$)), amino-R$_{363}$SMKLSFRA-RAYDFRGPG$_{383}$ (SEQ ID NO:18) (also referred to herein as a dog CST sequence (CHGA$_{363-383}$)), amino-R$_{415}$SMKLSFRAQAYGFPGPEPQL$_{435}$-carboxyl (SEQ ID NO:19) (also referred to herein as a guinea pig CST sequence (CHGA$_{415-435}$)), amino-R$_{354}$SMKLSFRA-RGYGFGAPGPQL$_{374}$-carboxyl (SEQ ID NO:20) (also referred to herein as a myotis CST sequence (CHGA$_{354-374}$)), amino-R$_{362}$SMKLSLRARSYGFGGP-GPQL$_{382}$-carboxyl (SEQ ID NO:21) (also referred to herein as a African bush elephant CST sequence (CHGA$_{362-382}$)), amino-R$_{382}$SMKLSLQTRAYDFRGPGPQL$_{402}$-carboxyl (SEQ ID NO:22) (also referred to herein as a small-eared galago CST sequence (CHGA$_{382-402}$)), amino-R$_{283}$SMKLSFQAPAYDFRGSGPQL$_{303}$-carboxyl (SEQ ID NO:23) (also referred to herein as a mole rat CST sequence (CHGA$_{283-303}$)), amino-R$_{318}$SMKLSFQSRAYGFRGP-RHQL$_{338}$-carboxyl (SEQ ID NO:24) (also referred to herein as a Chinese tree shrew CST sequence (CHGA$_{318-338}$)), and amino-R$_{358}$AMKLSFRARGYDFSGPGLQL$_{378}$-carboxyl (SEQ ID NO:25) (also referred to herein as a killer whale CST sequence (CHGA$_{358-378}$)).

In another embodiment, the RI-CST peptide so obtained above can have any of the amino acid replaced with a corresponding amino acid from the same relative position from any of the RI-CST peptide(s). For example, CST additionally comprises an ordered group of amino acids, wherein the amino acid at any one or more position(s) may be exchanged with an amino acid at the same position(s) from any of the peptide in the above paragraph. Based on the amino acid sequence so-obtained, an RI-CST peptide may be synthesized comprising D-amino acid in place of L-amino acid except for achiral glycine and an inverse order of the amino-to-carboxyl sequence.

In another embodiment, the RI-CST peptide is a fragment or derivative of the RI-CST peptide of the above two paragraphs.

In another embodiment, the artificial RI-CST peptide may be chemically synthesized by a solid-phase method using 9-fluorenylmethoxycarbonyl (Fmoc) protection chemistry. Additionally, the chemically synthesized peptide may be purified by preparative reverse-phase, high performance liquid chromatography (RP-HPLC). In one embodiment, the RP-HPLC includes the use of reverse phase C18 column. Further, the purified chemically synthesized peptide may be analyzed for authenticity and purity by repeat RP-HPLC and electrospray ionization mass spectroscopy.

In one particular embodiment, an equivalent of human CST is a RI-CST (CHGA$_{372-352}$) (also referred to herein as a retro-inverso peptide) having the sequence amino-l$_{372}$qpGpGrfGyararfslkmss$_{352}$-carboxyl (SEQ ID NO:27). In this embodiment, the amino acids are D-isomers except for the achiral glycine (G). Additionally, invention provides embodiments wherein the retro-inverso peptide is a fragment or derivative of any of the retro-inverso peptide above.

The invention also provides embodiments, wherein the CST equivalent is a macromolecule that is a peptide or polypeptide. Additionally, the peptide or polypeptide may have a β-strand-loop-β-strand structure. Further, the loop of the β-strand-loop-β-strand structure may have one or more positive charges. Also, in an embodiment of the invention, the positive charge may be conferred by one or more arginines. Preferably, the CST equivalent contains three arginines.

In an embodiment of the invention, the positive charges comprises three positive charges in a similar spatial arrangement or orientation as the positively charged side chain of arginine-359, arginine-361 and argnine-366 of the human CST peptide (a) of any of the CSTs described above.

Further, in one embodiment, the CST or equivalent thereof is a peptide or polypeptide that comprises an amphiphilic β-strand. Additionally, CST or CST equivalent comprises L-amino acid, D-amino acid, or combination of L- and D-amino acid.

In another embodiment, the CST equivalent is not a peptide or polypeptide but is a synthetic molecule or small molecule. The synthetic molecule or small molecule may have one or more positive charges at or near neutral pH. In one embodiment, the synthetic molecule or small molecule is a CST-mimetic 1, 3-bis[3-[(E)-N-(diaminomethyllideneamino)-C-methylcarbonimidoyl]phenyl]thiourea} having a structure:

In accordance with the practice of the invention, the composition of the invention may be administered by an intraperitoneal route, enteral route, buccal route, inhalation route, intravenous route, subcutaneous route or intramuscular route.

Further, the compositions of the invention may be formulated as an oral dosage form. The oral dosage form may be a tablet, minitablet, caplet or capsule.

In one embodiment, the compositions of the invention are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound (a CST or equivalent thereof) is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of an active compound in the pharmaceutical composition will depend on absorption, inactivation and excretion rates of the active compound, the physicochemical characteristics of the compound, the dosage schedule, and amount administered as well as other factors known to those of skill in the art.

Merely by way of example, a therapeutically effective dosage may produce a serum concentration of active ingredient of from about 0.1 ng/ml to about 100 µg/ml. The pharmaceutical compositions, in another embodiment, may provide a dosage of from about 0.001 mg to about 2000 mg of compound per kilogram of body weight per day. Pharmaceutical dosage unit forms are prepared and may provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the active ingredient (also referred to herein as compounds) exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the diseases, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses, which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Merck Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001% 100% (wt %) active ingredient, in one embodiment 0.1 95% (wt %), in another embodiment 75 85% (wt %).

A. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

1. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammuoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous-liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

B. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein may be dispersed e.g., in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate-controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN™ 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

D. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01% 10% (vol %) isotonic solutions, pH about 5 7, with appropriate salts.

E. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration F. Targeted Formulations The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, and 5,709,874.

In one embodiment, liposomal suspensions, including tissue-targeted liposomes, such as cell-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

G. Combination Therapy

In another embodiment, the compounds may be administered in combination, or sequentially, with another therapeutic agent. Such other therapeutic agents include those known for treatment, prevention, or amelioration of one or more symptoms of amyloidosis and neurodegenerative diseases and disorders. Such therapeutic agents include, but are not limited to, donepezil hydrochloride (Aricept), rivastigmine tartrate (Exelon), tacrine hydrochloride (Cognex) and galantamine hydrobromide (Reminyl).

III. KITS

According to another aspect of the invention, kits are provided. Kits according to the invention include package(s) comprising compounds or compositions of the invention.

The phrase "package" means any vessel containing compounds or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compounds or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In other embodiments, compounds are provided in an inhaler. In still other embodiments compounds are provided in a polymeric matrix or in the form of a liposome.

The following examples are presented to illustrate the present invention and to assist one of ordinary skill in making and using the same. The examples are not intended in any way to otherwise limit the scope of the invention.

EXAMPLES

Example 1

Experimental Procedures
Animals—

Adult male (7 month old) WT (31.8±1.2 g) and Chga-KO (39.2±1.5 g) mice in the mixed genetic background (129SvJ×C57BL/6) were studied. Both genotypes were generated from the original founder carrying mixed genotype (50% 129SvJ, 50% C57BL/6) and were maintained by sibling mating. Animals were kept in a 12 hr dark/light cycle and fed standard chow ad libitum. Male C57BL/6 mice, 8 week old, were fed 60% high fat diet (D12492: Research Diets, Inc., New Brunswick) for 16 weeks before using for experiments. Male leptin-deficient (C57BL/6J-Ob/Ob) mice from the Jackson Laboratory were maintained on a standard chow diet. The Institutional Animal Care and Utilization Committee approved all procedures. Chga-KO, DIO and Ob/Ob mice were treated daily with saline or CST (5 μg/g BW, i.p.; 12 days for Chga-KO mice and 16 days for DIO and Ob/Ob mice).

Measurement of Glycerol, Adipokine, Lipid and CST Levels in Blood and in Conditioned Media—

Mice were fasted for 12 hr prior to blood draw. Triglycerides (TG) and non-esterified fatty acids (NEFA) were assayed using kits from Wako Diagnostics (Richmond, Va.). Glycerol was assayed using a kit from Sigma (St Louis, Mo.). Media from the explant cultures and mouse serum were analysed for glycerol and NEFA as a measure of lipolysis. ELISA kits were used to determine plasma levels of leptin, adiponectin (Millipore, Billerica, Mass.) and CST (Bachem, Torrance, Calif.). For CST assay, plasma samples and reference standards were passed through mini C18 columns and the flow-through fractions were assayed. The same kits were used for measurements in culture media.

Treatment of Fat Pad Explants with CST and Leptin—

Adipose tissue explants were prepared as described (42). Epididymal fat pads from 12 hr fasted WT, Chga-KO, DIO and Ob/Ob mice with or without CST treatment were collected in Kreb-Ringer-phosphate (KRP) buffer containing 10 mM Hepes and 0.5% BSA. Tissues were minced to 1-2 mm size and treated with 100 nM CST, 1 μM leptin, or saline for 30 min (for signaling analysis) or 3 hr (for lipolysis and β-oxidation assays). Explants were also treated acutely with CST, leptin, a combination, or saline. At the end, incubation media were saved for analysis of glycerol and fatty acid release. Explants were washed prior to homogenization for immunoblotting and analysis of fatty acid oxidation.

Preparation of Primary Adipocytes—

Primary adipocytes were isolated from epididymal fat pads essentially as described (43). Adipose tissues from WT and Chga-KO mice were minced in Krebs-Ringer bicarbonate-Hepes (KRBH) buffer, pH 7.4, containing 10 mM bicarbonate, 30 mM Hepes, 200 nM adenosine, 2.5 mM glucose and 1% fatty-acid-free BSA, and digested for 30-40 min with Type I collagenase (10 mg/g tissue; Invitrogen, Carlsbad, Calif.) with gentle swirling in a 37° C. incubator. The digestion mixture was then filtered through a nylon strainer and centrifuged at 400×g for 1 min. The oily layer (released from broken cells) above floating fat cells was skimmed off, and fat cells were recovered from the top and washed three times with warm KRBH.

Immunoblotting of Signaling Molecules—

Adipose tissue explants after treatments ex vivo and tissues from mice treated in vivo were homogenized in a buffer containing phosphatase and protease inhibitors (20 mM Tris/HCl (pH 7.5), 250 mM sucrose, 2 mM EDTA, 2 mM EGTA, 2 mM $Na_3VO_4$, 10 mM NaF, 2 mM $Na_4P_2O_7$, 1 mM phenylmethylsulfonyl fluoride, 20 μg/ml leupeptin, 10 μg/ml aprotinin, and 1 μM LR-microcystin) as described (38,44). Homogenates were subjected to SDS-PAGE and immunoblotted. Primary antibodies for AMPK and Stat3 were from Cell Signaling Technology (Beverly, Mass.). The chemiluminescence kit was from Pierce (Rockford, Ill.).

Incorporation and Oxidation of Fatty Acid In Vivo—

Mice were injected with saline or CST (5 μg/g BW, i.p.; twice daily) for 12 days. One hr after the final injection, U-$^{14}$C-palmitate (5 μCi, 100 μl of 0.2 mM, i.p.) was injected and mice were sacrificed 3 hr later. Liver and adipose tissues (~100 mg) were homogenized in 0.8 ml 3.5 N perchloric acid and extracted by vortexing in 3 ml of a mixture of methanol and chloroform (2:1, v/v). To the final homogenate, 1.2 ml of 3.5 N perchloric acid was added. The mixture was vortexed and centrifuged. The lower (chloroform) layer contained all the lipids derived from the incorporation of $^{14}$C-palmitate, whereas the upper acidic layer contained partially oxidized acid-soluble metabolites (ASM) of $^{14}$C-palmitate. The lower layer was further fractionated by thin layer chromatography on silica gel plates using hexane: diethyl ether: acetic acid (79:20:1, v/v/v) mixture as the developing solvent. Lipogenesis from palmitate was determined based on the radioactivity of the free palmitic acid band compared to other lipids (phospholipids, triglycerides, diacylglycerol, etc.) on the TLC plate. Complete oxidation of $^{14}$C-palmitate was measured in cultured cells but not in mice.

Fatty Acid Oxidation in Explants and Cultured Cells.

Oxidation of radiolabeled palmitate in the homogenates of adipose tissue explants as described previously (45). For oxidation studies of cultured cells, HepG2 (hepatocytes) and 3T3-L1 preadipocytes were obtained from ATCC and cultured following supplier's protocol. Confluent 3T3-L1 cultures were differentiated into adipocytes by treating with a cocktail of dexamethasone (100 nM), IBMX (1 µM) and insulin (100 nM) for 10 days. Media were then switched to serum-free DMEM with 1% BSA. Hepatocytes were assayed for lipogenesis and fat oxidation in response to CST treatment. Serum-free cultures were treated with CST (100 nM) for 24 hr followed by a 2 hr incubation with $U^{14}C$-palmitate (0.5 µCi/ml). Fatty acid oxidation in cells was determined by modifying a published method (46). Specifically, the culture media in 24-well plates were acidified with 10% HClO4 after incubation with the labeled fatty acid and immediately covered with a thick filter paper sheet (cut to size) soaked in 2 N NaOH and placed underneath the plastic lid. The whole plate was sealed with parafilm. After further incubation for 2 hr, the filter paper sheet was marked as circles around the rim of the wells and then the circles were excised. The filter discs were counted to determine the amount of $^{14}CO_2$ absorbed in the papers. Cells in the culture wells were lysed in 1 N NaOH and protein content was assayed using Folin's reagent (BioRad, Hercules, Calif.).

Real-Time PCR—

RNA was extracted using a kit (RNeasy Plus, Qiagen, Valencia, Calif.) according to the manufacturer's specifications. After DNase digestion, 100 ng of RNA was transcribed into cDNA in a 20-µl reaction using a High Capacity cDNA kit (Invitrogen, Carlsbad, Calif.), analyzed, and amplified. PCR was performed in a 25-µl reaction containing 5 µl of cDNA (one-fifth diluted), 2×SYBR Green PCR Master Mix, and the primers described in Table 1 (400 nM each). Differences in cycle threshold values (ΔCt) between target and the housekeeping gene GAPDH were used to calculate the levels of expression.

TABLE 1

Primers for RTqPCR

| | |
|---|---|
| Srebp-1c Forward GGA GCC ATG GAT TGC ACA TT | SEQ ID NO: 28 |
| Reverse GCT TCC AGA GAG GAG GCC AG | SEQ ID NO: 29 |
| Gapdh Forward TAT GTC GTG GAG TCT ACT GGT GT | SEQ ID NO: 30 |
| Reverse GTC ATC ATA CTT GGC AGO TTT CT | SEQ ID NO: 31 |
| Gpat4 Forward TGT CTG GTT TGA GCG TTC TG | SEQ ID NO: 32 |
| Reverse TTC TGG GAA GAT GAG GAT GG | SEQ ID NO: 33 |
| Pparγ1 Forward GAG TGT GAC GAC AAG ATT TG | SEQ ID NO: 34 |
| Reverse GGT GGG CCA GAA TGG CAT CT | SEQ ID NO: 35 |
| Cd36 Forward TCC AGC CAA TGC CTT TGC | SEQ ID NO: 36 |

TABLE 1-continued

Primers for RTqPCR

| | |
|---|---|
| Reverse TGG AGA ATT ACT TIT TCA GTG CAG AA | SEQ ID NO: 37 |
| Ucp2 Forward CAG CCA GCG CCC AGT ACC | SEQ ID NO: 38 |
| Reverse CAA TGC GGA CGG AGG CAA AGC | SEQ ID NO: 39 |
| Cpt1 Forward CAG GAT TTT GCT GTC AAC CTC | SEQ ID NO: 40 |
| Reverse GAG CAT CTC CAT GGC GTA G | SEQ ID NO: 41 |
| Acox Forward GTC GAC CTT GTT CGC CA | SEQ ID NO: 42 |
| Reverse GGT TCC TCA GCA CGG CTT | SEQ ID NO: 43 |
| Ppara Forward GGG CTC TCC CAC ATC CTT | SEQ ID NO: 44 |
| Reverse CCC ATT TCG GTA GCA GGT AGT C | SEQ ID NO: 45 |

Statistics—

Data are expressed as the mean±S.E.M. Curve fitting was accomplished using the program Kaleidagraph (Synergy Software, Reading, Pa.). Statistical analyses 30 were done by Student's t-test or one-way ANOVA followed by Bonferroni's post hoc test. Statistical significance was defined as $p<0.05$.

Results

Effects of CST on Adiposity, Plasma Lipid and Leptin Levels in Overweight Chga-KO Mice—

Plasma CST concentration was ~4 ng/ml in WT mice fed with a normal chow diet (NCD: FIG. 1A). Administration of CST (5 µg/g BW, i.p./day for 12 days) to these mice raised CST concentration to 7 ng/ml (FIG. 1A) and maintained at this level for at least 4 hr. High fat diet (HFD, 60% fat, for 16 weeks) decreased CST levels to 2.8 ng/ml. CST administration to CST-deficient Chga-KO mice achieved a lower CST level (2.3 ng/ml) than WT mice. Chronic CST administration (5 µg/g BW, i.p./day for 12 days) to Chga-KO mice reduced epididymal fat pad size to WT level without affecting body weight (FIGS. 1B&C and FIG. 2) or liver weight (Saline: 1.20±0.08 g versus CST: 1.27±0.07 g). Interestingly, CST decreased plasma TG levels in Chga-KO mice (FIG. 1D). This decrease in overall lipid content may be caused in part by increased lipolysis as shown by increased glycerol and NEFA levels in plasma (FIGS. 1E&F). We found that Chga-KO mice have higher leptin levels than WT (FIG. 1G), consistent with the established consequence of PST deficiency in the Chga-KO mice (38). Interestingly, CST treatment of Chga-KO mice lowered plasma leptin to a level below WT (FIG. 1G), suggesting that leptin at subphysiological levels is sufficient to maintain the Chga-KO mice in a lean state. CST also inhibited leptin production in cultured 3T3-L1 adipocytes (FIG. 1H), suggesting a direct effect on leptin secretion independent of other circulating factors. Although leptin is known to facilitate fat oxidation and decrease food intake (47,48), sustained hyperleptinemia may desensitize its receptor and lead to obesity as seen in DIO models (49,50). We therefore reasoned that CST restored leptin action in Chga-KO mice by reversing the desensitization effect of chronic leptin excess. CST did not increase food intake of Chga-KO mice, suggesting that CST despite lowering leptin levels preserved leptin signaling in the brain. Leptin-deficient Ob/Ob mice with sensitive leptin receptors responded to short-term CST treatment by reducing food intake, whereas DIO mice, with peripheral leptin resistance and with a barrier against circulating leptin for hypothalamic action, failed to respond (as discussed later in FIGS. 7A&B).

Effects of CST on Lipogenesis, Fatty Acid Oxidation and Gene Expression in Chga-KO Mice—

In Chga-KO mice treated with CST, we found tissue-specific effects on $^{14}$C-palmitate incorporation into lipids. The incorporation was decreased by CST in adipose tissue but enhanced in liver (FIGS. 3A&B). In contrast, CST stimulated palmitate oxidation into ASMs in both adipose tissue and liver (FIGS. 3C&D). The effect of CST on $^{14}$C-palmitate oxidation in cultured hepatocytes (HepG2) and adipocytes (3T3-L1) was measured based on $^{14}$CO$_2$ formation (FIG. 3E). Given that adipose tissue in CST-treated mice showed increased palmitate oxidation but decreased incorporation into lipids, we conclude that CST inhibits the expansion of adipose tissue and also promotes fatty acid uptake in liver for oxidation. Liver mRNA analyses revealed that CST augmented the expression of Acox, Cpt1α, Ucp2, and Pparα genes involved in fatty acid oxidation (FIG. 4A-D). In contrast, CST had no effect on the expression of lipogenic genes such as Srebp-1 and Pparγ. Interestingly, CST stimulated the expression of Cd36, a transporter mediating cellular uptake of long-chain fatty acids, as well as the lipogenic gene Gpat4 (glycerol-3-phosphate acyltransferase-4) (FIG. 4E). This indicates that CST stimulates fatty acid incorporation into triglycerides but not de novo lipogenesis. Overall, CST appears to promote lipid flux from adipose tissue toward liver for catabolism.

Modulation of Adrenergic Receptor (ADR)-Mediated Lipolysis by CST in Adipocytes—

Figure 5:
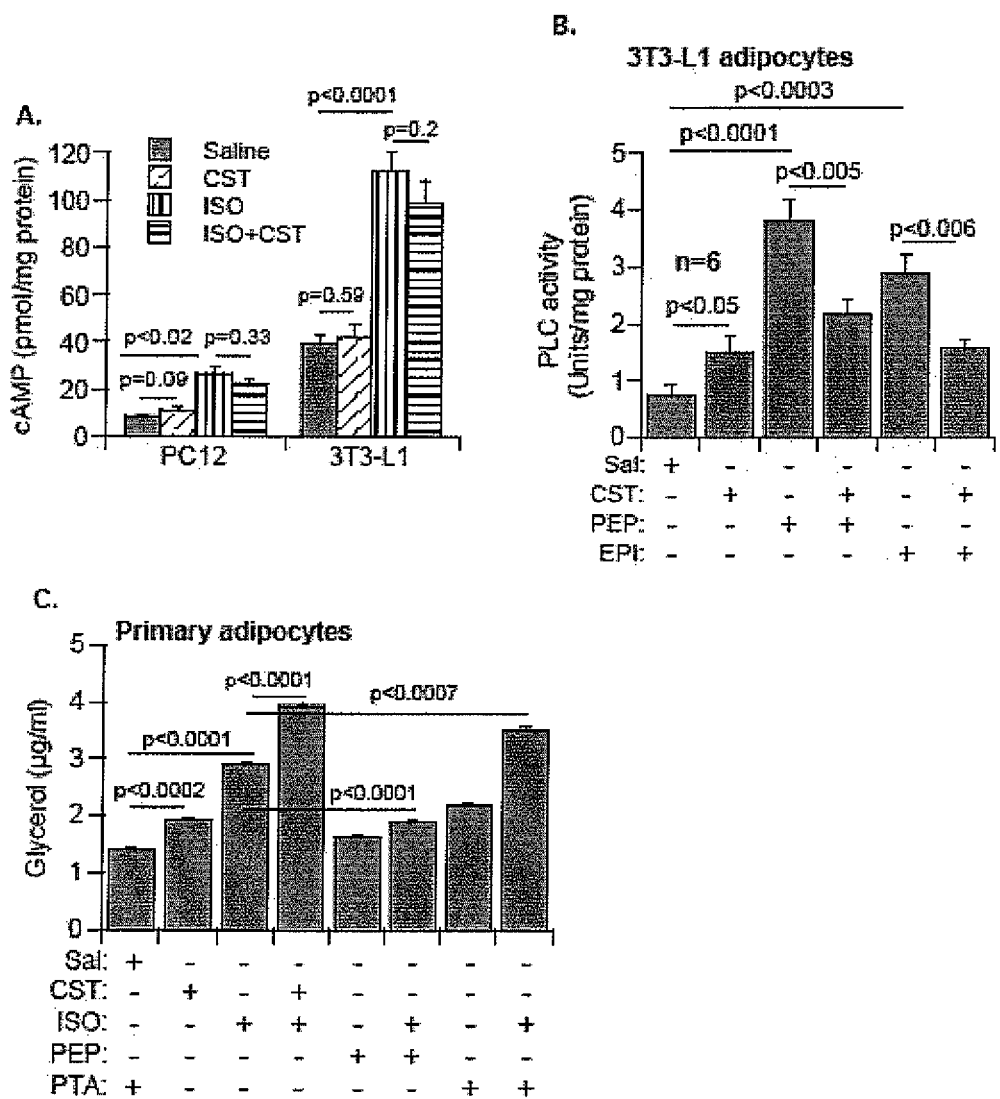
FIG. 5. Regulation of adrenergic signaling by CST as measured by cAMP production, phospholipase C activity, and lipolytic glycerol release. (A) Effects of CST (100 nM, 10 min) on cAMP production in PC-12 and 3T3-L1 cells pretreated with saline or isoproterenol (ISO) (10 μM) for 10 min. (B) Effects of CST on phospholipase C activity in 3T3-L1 adipocytes pretreated with phenylephrine or epinephrine (10 μM for 10 min). (C) Effects of CST on glycerol release from adipocytes pretreated with ISO, phenylephrine (PEP), and phentolamine (PTA) (10 μM for 10 min).

We examined the direct effects of CST in cultured cells. In both 3T3-L1 adipocytes and PC-12 neuroendocrine cells, cAMP production was stimulated by isoproterenol but not by CST (FIG. 5A), indicating that CST did not stimulate β-ADR signaling. In contrast, CST attenuated phospholipase C (PLC) activation by both phenylephrine (an α-ADR agonist) and epinephrine in 3T3-L1 adipocytes (FIG. 5B). Since epinephrine activates both α- and β-ADR, the inhibition of its effect on PLC by CST might represent selective inhibition of α-ADR. Of note, CST itself mildly stimulates PLC but inhibits the stimulatory effect of α-ADR agonists (FIG. 5B), suggesting that PLC activation by CST itself is α-ADR-independent.

As in Chga-KO mice, CST also inhibited leptin release from 3T3-L1 adipocytes (FIG. 1H) and stimulated glycerol release from primary adipocytes (FIG. 5C). Consistent with the literature (30), we found that in adipocytes, the α-ADR antagonist phentolamine stimulated lipolysis and potentiated the lipolytic effects of the β-ADR agonist isoproterenol (FIG. 5C). In contrast, the α-ADR agonist phenylephrine dampened the lipolytic effect of isoproterenol (FIG. 5C). Both the α-antagonist phentolamine and CST potentiated the effects of isoproterenol (FIG. 5C). These findings suggest that CST recapitulates the lipolytic effect of the α-ADR antagonist phentolamine. This commonality of CST with phentolamine, coupled with its ability to inhibit phenylephrine action (FIG. 5B), suggests that CST acts by suppressing α-ADR signaling.

CST Re-Sensitizes Chga-KO Mice to Leptin—

Leptin signals through AMPK and MAPK pathways and activates the transcription factor Stat3 (51-53). Chronic elevation of plasma leptin level causes desensitization of its receptor, leading to attenuation of Stat3 phosphorylation (49,50). Acute CST treatment of adipose tissue explants from Chga-KO mice stimulated AMPK phosphorylation (FIG. 6A), an effect likely independent of leptin action because similar stimulation was also seen in cultured hepatocytes. Leptin signaling appeared to be subdued in Chga-KO mice as evidenced by the decreased phosphorylation of AMPK and STAT3 compared to WT following acute leptin treatment (FIGS. 6B&D). CST treatment restored leptin's ability to stimulate the phosphorylation of AMPK (FIG. 6C) as well as Stat3 (FIG. 6D), suggesting that CST-induced lowering of plasma leptin in Chga-KO mice might have re-sensitized leptin receptor.

Modulation of Peripheral Leptin Action by CST in Leptin-Resistant DIO Mice and Leptin—Deficient Ob/Ob Mice with Sensitive Leptin Receptors—

Figure 7:
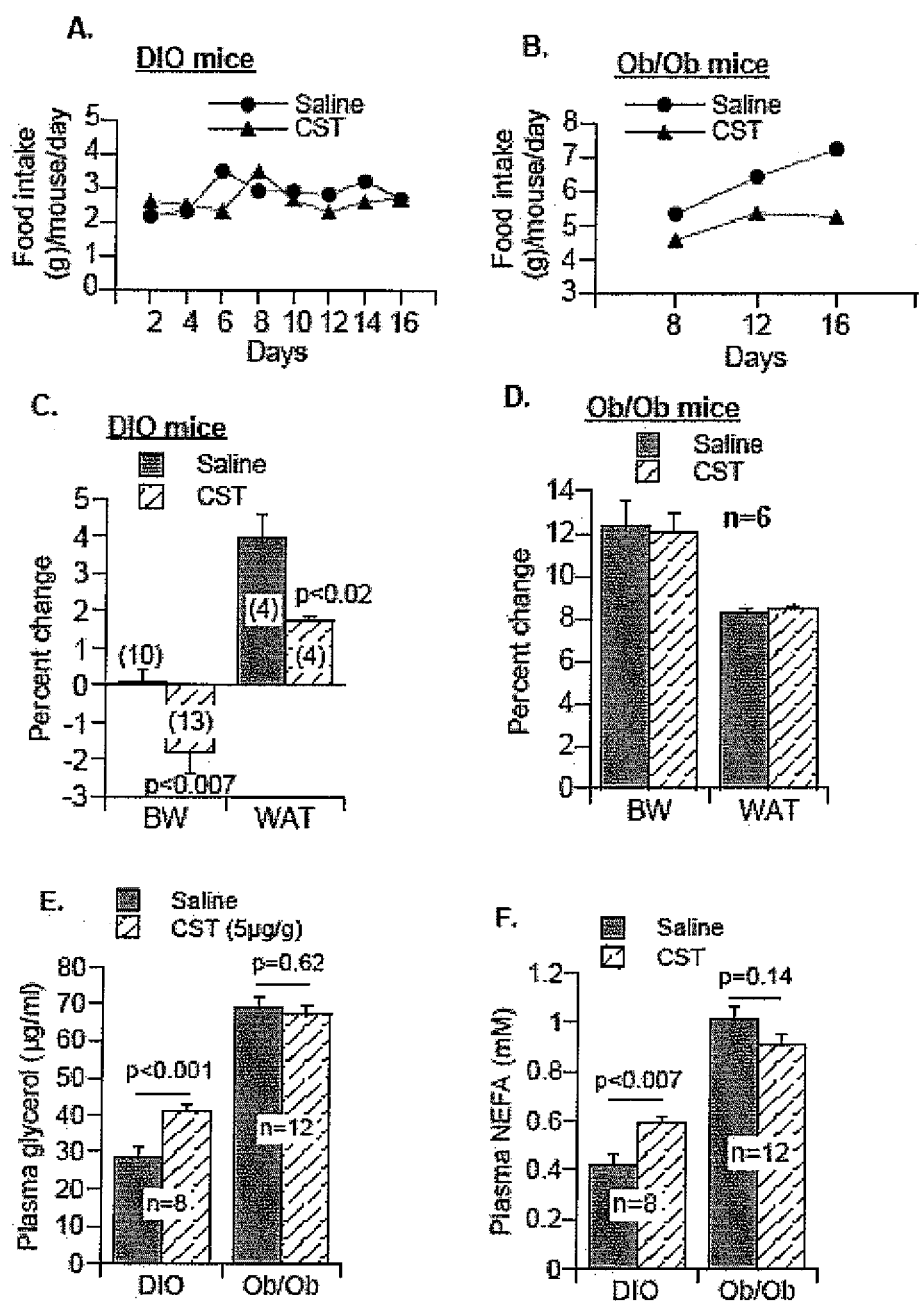
FIG. 7. Effects of CST administration to DIO and Ob/Ob mice on food intake, body weight, adipose tissue weight, and lipolysis. CST (5 μg/g BW, i.p./day) or saline was administered to DIO and Ob/Ob mice for 16 days. Food intake for DIO mice (A) and Ob/Ob mice (B) was measured every other day. Percent changes in final body weight and WAT mass (as % of body weight) were determined for DIO (C) and Ob/Ob (D) mice. Plasma glycerol (E) and NEFA (F) were quantified for DIO and Ob/Ob mice at the end of CST treatment.

In contrast to insulin sensitive Chga-KO mice, DIO and Ob/Ob mice are insulin resistant and obese. However, DIO mice exhibit peripheral leptin resistance (54-56) whereas Ob/Ob mice maintain functional leptin receptors and full responsiveness to exogenous leptin (57-60). Since our focus in this work has been to study the regulation of lipid metabolism and leptin action by CST in adipose tissue, not in hypothalamus, we examined their effects ex vivo in adipose tissue explants. Adipose tissues from these two models of obesity, DIO and Ob/Ob mice, offer the opportunity to further clarify our observations in Chga-KO mice. When CST was administered to DIO and Ob/Ob mice for 16 days, food intake in DIO mice did not change but there was a distinct indication that food intake in Ob/Ob mice started to level off (FIGS. 7A&B). Interestingly, decreased food intake by Ob/Ob mice was not reflected in any decrease in body weight or adipose tissue mass whereas CST treatment for 16 days decreased body weight and adipose mass in DIO mice without a change in food intake (FIGS. 7C&D). Similarly, lipolysis as measured by the plasma concentrations of glycerol and NEFA was not affected in Ob/Ob mice but was increased by CST treatment in DIO mice (FIGS. 7E&F). From this experiment it appears that in terms of food intake during the treatment period, CST might have produced a central effect in leptin sensitive Ob/Ob mice but not in leptin resistant DIO mice. It is likely that a longer treatment with CST will be necessary to manifest CST effect in Ob/Ob mice and to translate the observed decrease in food intake into changes in body weight, tissue size and overall metabolism. However, increased lipolysis and decreased body weight and adipose tissue mass indicated a significant peripheral effect in DIO mice. It should be noted that an average of 1.1 g (2%) decrease in body weight was accompanied with about 2 g decrease in adipose tissue mass.

CST and Leptin Effects on Adipose Explants of DIO and Ob/Ob Mice with or without Prior CST Treatment In Vivo—

Figure 8:
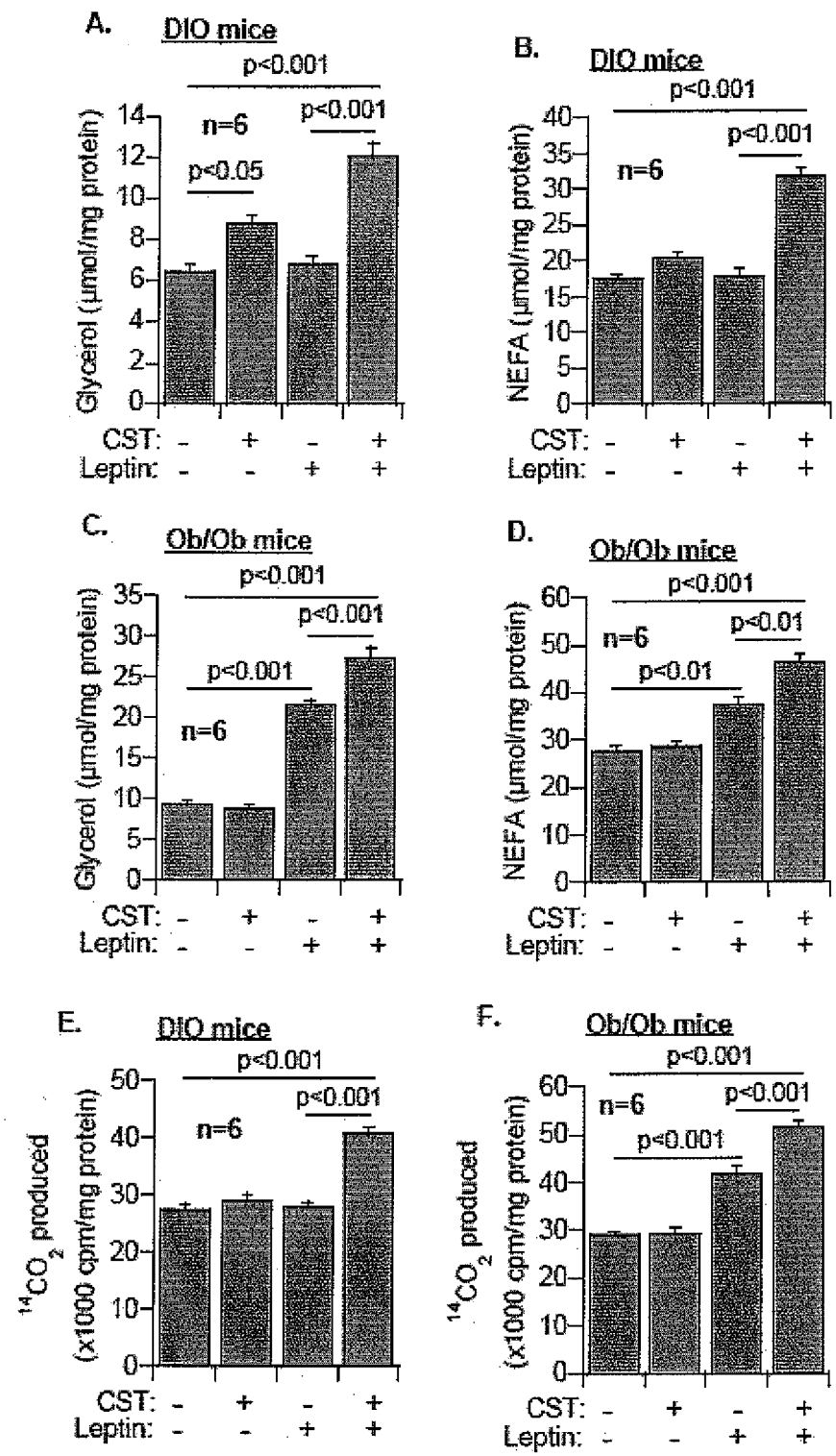
FIG. 8. Lipolysis and fatty acid oxidation in the adipose tissue explants of DIO and Ob/Ob mice after treatment with saline or CST for 16 days. Explants were incubated with saline or leptin (1 μM) for 3 hr and the concentrations of glycerol (A&C) and NEFA (B&D) released into the media from DIO (A&B) and Ob/Ob (C&D) explants were determined as a measure of lipolysis. Homogenates of the explants from DIO (E) and Ob/Ob (D) were used to determine their capacity for oxidation of U-$^{14}C$-palmitate in response to the treatment with saline, CST, leptin and CST+leptin. The $^{14}CO_2$ released was captured and counted as the measure of fatty acid oxidation.

While leptin-deficient Ob/Ob mice possess functional leptin receptors and maintain leptin sensitivity (57-60), DIO mice develop peripheral leptin resistance but maintain partial sensitivity to centrally administered leptin (54-56). To examine the direct effects of leptin on adipose tissue lipolysis and fatty acid oxidation, and the influence of CST on leptin action, we treated DIO and Ob/Ob mice with CST or saline in vivo, and exposed adipose explants to leptin for 30 min (for AMPK and Stat3 signaling) and 3 hr (for lipolysis and fatty acid oxidation analysis). After incubation with leptin, an analysis of glycerol and NEFA release in the media demonstrated that while the explants from CST-treated DIO mice (exposed to both CST and leptin in vivo) can release some glycerol in the media, the best lipolytic response was produced when leptin was added to the cultures of CST treated explants (FIG. 8A). CST effects on NEFA release by the explants from CST-treated DIO mice was not significant. It is possible that the released NEFA might have undergone further metabolism during the 3 hr incubation. Nevertheless, addition of leptin to the cultures of CST treated explants resulted in augmented release of NEFA (FIG. 8B). It should be noted that leptin treatment did not stimulate lipolysis of explants from saline-treated mice (FIGS. 8A&B). These findings suggest that leptin resistance exists in adipose tissues of DIO mice and prior CST treatment in vivo might have improved leptin receptor functions. In contrast to DIO mice, 16 days of CST administration alone to Ob/Ob mice did not influence lipolysis in the explants, whereas the addition of leptin to the cultures of explant from saline treated Ob/Ob mice (no exposure to CST) stimulated lipolysis (FIGS. 8C&D), suggesting that (i) functional leptin receptors were present in the adipose tissue explants from Ob/Ob mice, and (ii) CST did not directly influence leptin receptor functions. However, adding leptin to the incubation with CST-treated explants from Ob/Ob mice produced highest lipolytic response (FIGS. 8C&D). The regulation of palmitate oxidation by the explants in response to CST and leptin more or less followed a pattern similar to lipolysis. Specifically, neither CST nor leptin alone stimulated oxidation in explants from DIO mice but the combination had a stimulatory effect (FIG. 8E), and the treatment with leptin alone (not CST alone) was stimulatory for oxidation in Ob/Ob explants but the combination showed highest oxidation (FIG. 8F).

Figure 6:
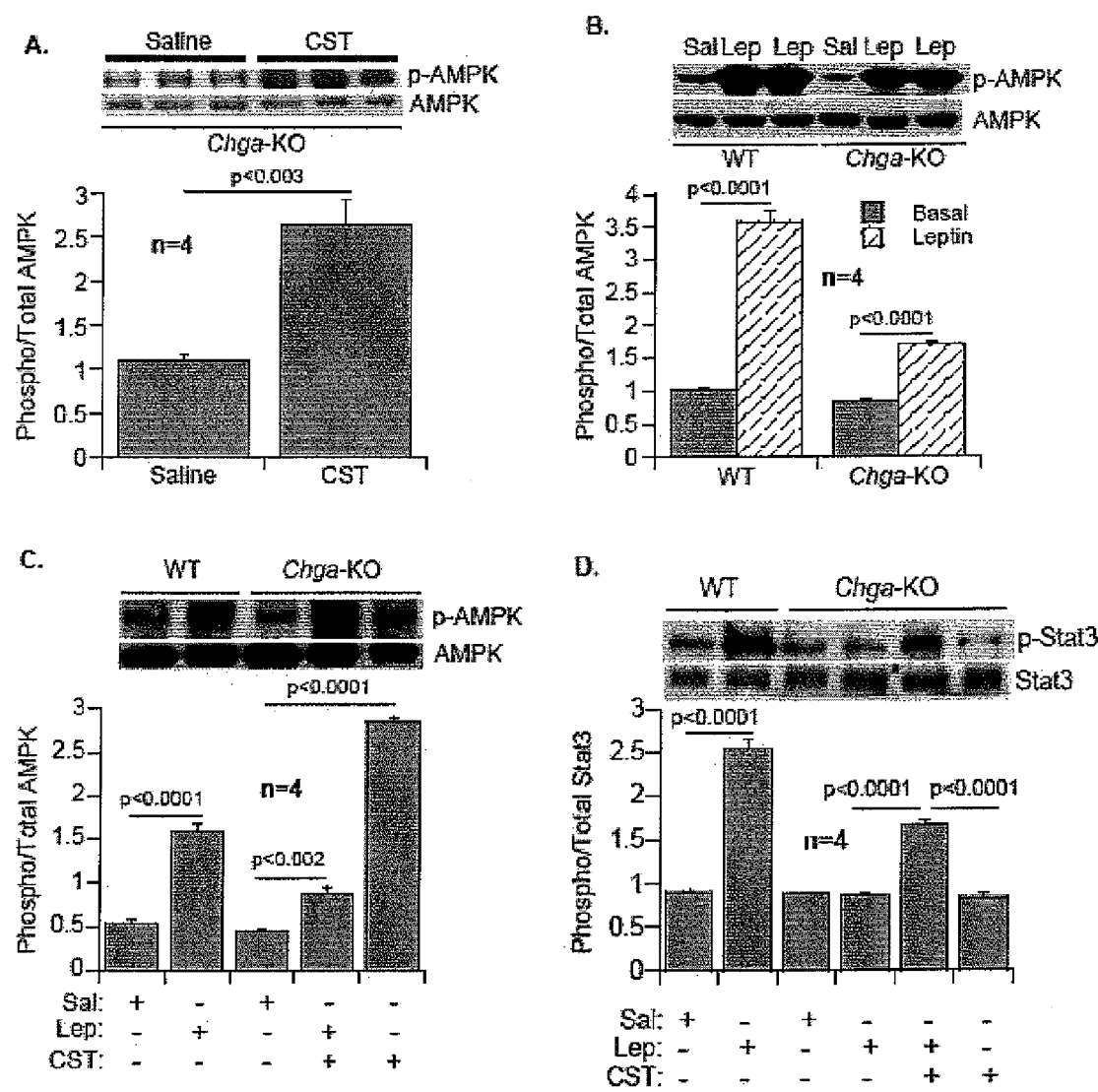
FIG. 6. Regulation of AMPK and Stat3 signaling by CST in adipose tissue explants. Explants from Chga-KO mice were treated with saline or CST (100 nM for 30 min) and immunoblotted for pAMPK and AMPK (A). Adipose explants from WT and Chga-KO mice were immunoblotted for pAMPK and AMPK after treatment with saline or leptin (1 μM) for 30 min (B). pAMPK and AMPK (C) and pStat3 and Stat3 (D) signaling in adipose explants from WT and Chga-KO mice after treatment for 30 min with saline, CST (100 nM), leptin (1 μM) or leptin plus CST.
Figure 9:
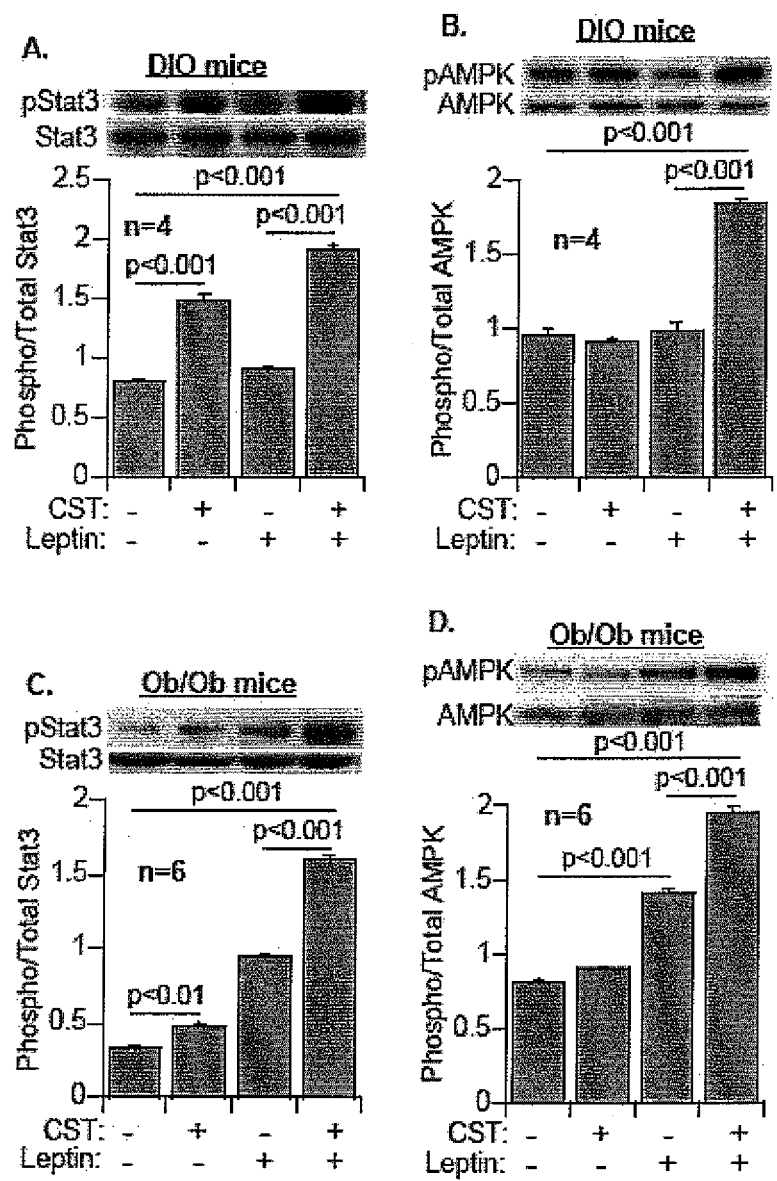
FIG. 9. Stat3 and AMPK signaling in the adipose tissue explants from DIO and Ob/Ob mice treated with saline, CST (in vivo) and leptin (ex vivo). Explants from DIO mice (A&B) and Ob/Ob mice (C&D) were incubated with saline or leptin (1 μM) for 30 min, homogenized and immunoblotted for phospho- and total Stat3 (A&C) as well as phospho- and total AMPK signals (B&D). Results are presented as the ratio of signal strength of phospho-over total.

Leptin treatment alone did not stimulate STAT3 and AMPK phosphorylation in DIO explants treated with saline (FIGS. 9A&B). The treatment of DIO explants with CST in vivo stimulated only STAT3 phosphorylation, not AMPK phosphorylation. It appears that CST may have a direct, leptin-independent effect on Stat3 phosphorylation. Sequential treatment with CST (in vivo) and leptin (ex vivo) resulted in the highest phosphorylation of both STAT3 and AMPK (FIGS. 9A&B). In Ob/Ob explants, the treatments with leptin alone stimulated phosphorylation of both STAT3 and AMPK (FIGS. 9C &D). Again, the treatment with a combination of leptin and CST showed the highest response. The CST stimulation of STAT3 phosphorylation in insulin resistant models (DIO and Ob/Ob mice, in FIG. 9) should be contrasted with the CST effects in insulin sensitive Chga-KO mice (FIG. 6). The lack of CST stimulation of Stat3 phosphorylation in the explants from Chga-KO mice (FIG. 6D) may represent the effects of other missing Chga peptides in the KO mice which gave rise to the increased insulin sensitivity in those mice. Conversely, CST alone significantly stimulated pAMPK signaling in Chga-KO mice (FIG. 6A). It suggests that other Chga-derived peptides could have a suppressive effect on pAMPK signaling stimulated by CST.

Discussion

Figure 2:
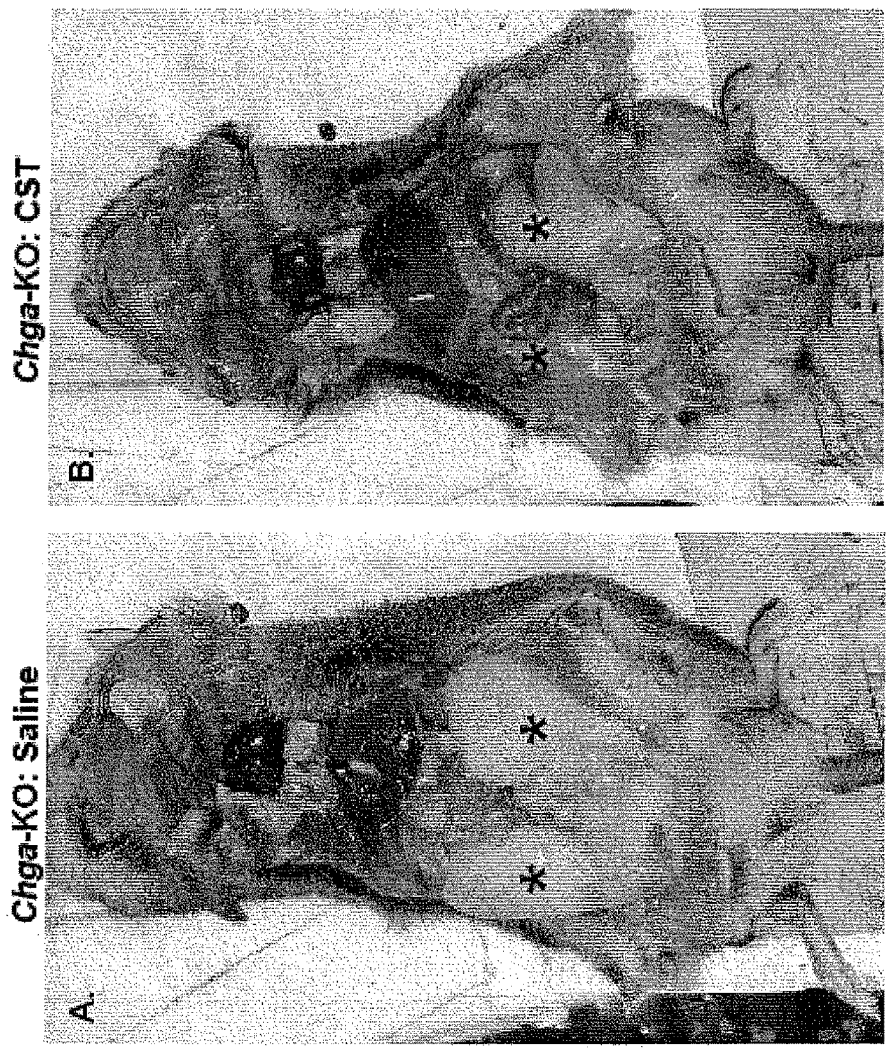
FIG. 2. Comparison of epididyaml fat pads between saline or CST-treated Chga-KO mice. Adipose tissue was compared after 12 days of treatment with saline (A) or CST (5 μg/g BW, i.p./day) (B). *indicates epididymal fat pad.

In this study, we found a novel CST function that reduces adiposity and mobilizes lipids from fat depot. These CST effects were examined in Chga-KO mice, where the lack of endogenous CST provided an ideal background for demonstrating the effects of exogenous CST. Another advantage of these mice over WT is their expanded adiposity on a regular chow diet, obviating the need for diet-induced obesity. Moreover, their circulating catecholamine levels are higher than WT (38) and desensitize adipose tissue to catecholamine-induced lipolysis. Likewise, Chga-KO mice also possess higher plasma leptin, adiponectin and ketone body levels than WT (38), yet their adiposity was not reduced despite increased lipid oxidation. These observations suggested that Chga-KO mice might be resistant to hormones such as catecholamines and adipokines, and that alleviation of the resistance could potentially explain the metabolic effect of exogenous CST. In fact, CST treatment in Chga-KO mice not only lowered high levels of circulating catecholamines and leptin (38) but also reduced overall adiposity (FIG. 2).

Figure 3:
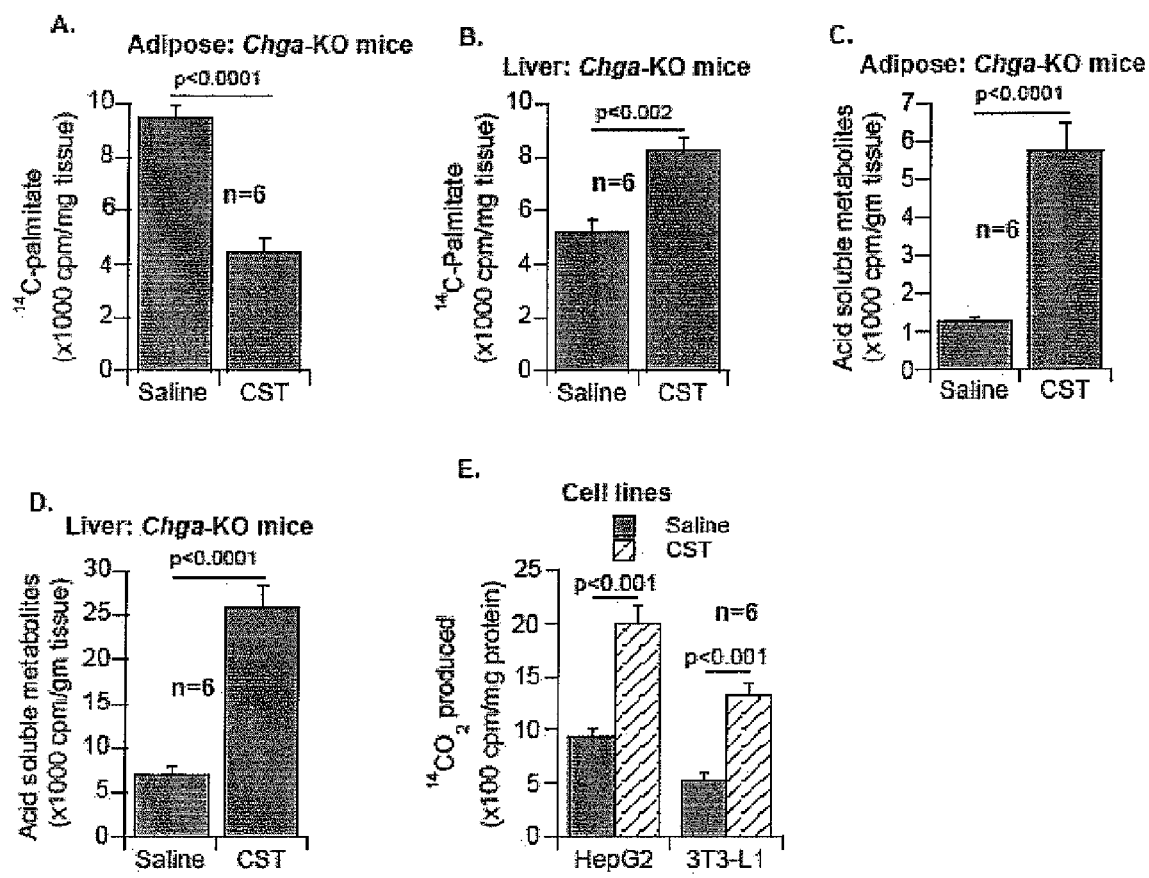
FIG. 3. Effects of CST on lipogenesis from fatty acid and fatty acid oxidation in hepatic and adipose tissues. Incorporation of $^{14}C$-palmitate into lipids in adipose (A) and liver (B) in Chga-KO mice after saline or CST treatment (5 μg/g BW, i.p./day) for 12 days. Partial oxidation to acid soluble metabolites (ASM) in adipose tissue (C) and liver (D). Complete oxidation to $^{14}CO_2$ in hepatocytes (HepG2) and adipocytes (3T3-L1) after saline or CST treatment (E).
Figure 4:
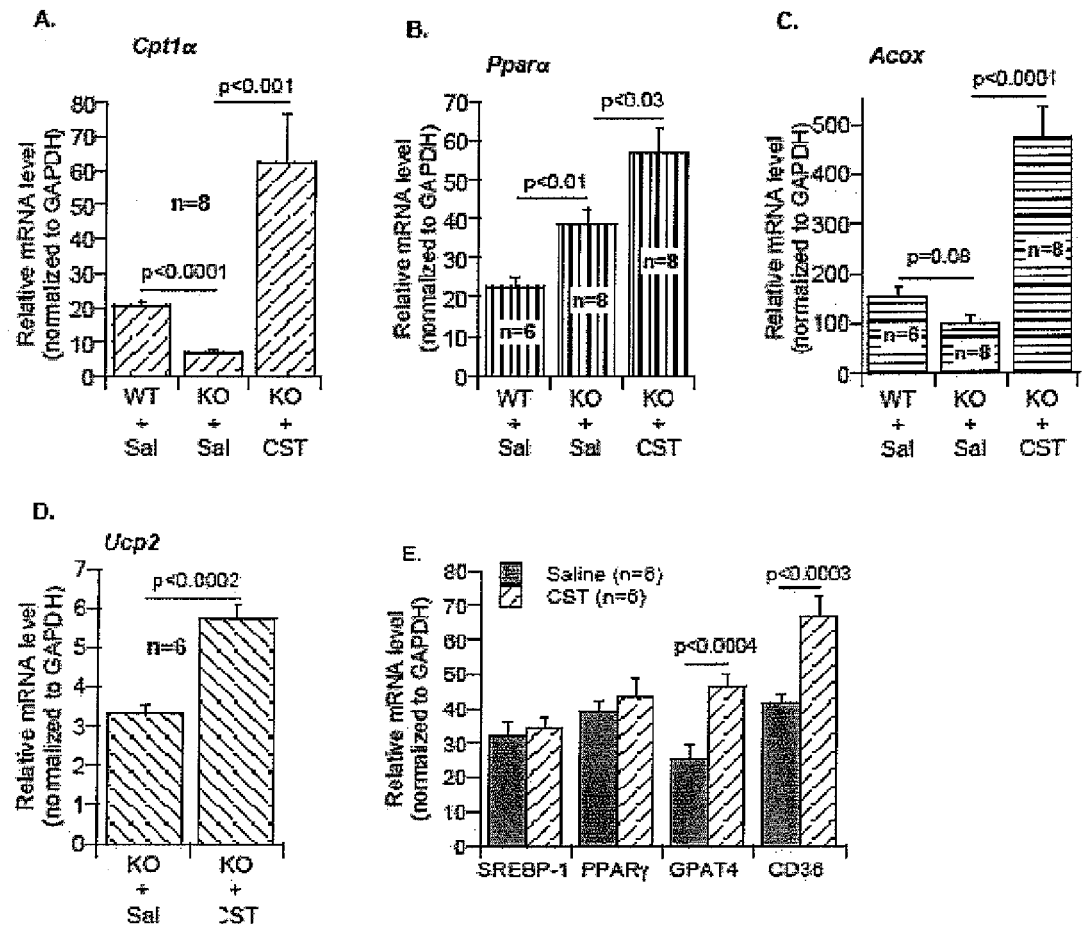
FIG. 4. Effects of CST on hepatic expression of genes involved in lipogenesis and fatty acid oxidation. Relative mRNA expression of genes involved in fatty acid oxidation in liver of WT and Chga-KO mice after treatment with saline or CST (5 μg/g BW, i.p./day) for 12 days: carnitine palmitoyltransferase 1a (Cpt1α) (A), peroxisome proliferator-activated receptor-alpha (Pparα) (B), acyl-CoA oxidase 1 (Acox1) (C) and uncoupling protein 2 (Ucp2) (D). (E) Relative expression of genes involved in lipogenesis in liver of Chga-KO mice after treatment with saline or CST (5 μg/g BW, i.p./day) for 12 days: sterol regulatory element-binding protein 1 (Srebp-1), peroxisome proliferator-activated receptor-gamma (Pparγ), glycerol-3-phosphate acyltransferase (Gpat4) and Cluster of Differentiation 36 (Cd36).

It appears that CST promotes lipolysis in adipose tissue (FIG. 1E) as well as fatty acid uptake and oxidation in liver (FIG. 3). In other words, CST treatment created an environment where lipolytic products (glycerol and fatty acids) were not re-esterified for storage. Therefore, its net metabolic effect is to favor lipid disposal. Of note, the lipid disposal promoted by CST was not mediated by increased catecholamine or leptin release. On the contrary, CST inhibits catecholamine release (7,61,62) and leptin production (FIG. 1G).

Since CST did not modulate basal or isoproterenol-induced cAMP levels in PC-12 cells (FIG. 5A), its lipolytic effect is probably not mediated by β-ADR signaling. Instead, inhibition of α-ADR signaling may underlie the lipolytic effect of CST given its ability to prevent phenylephrine from activating PLC. Existing literature indicates that α-ADR signaling inhibits lipolysis and that α-ADR blockade potentiates the lipolytic effect of β-ADR signaling (29,30,63,64). Acting like an α-ADR antagonist, CST enhanced the lipolytic effect of β-ADR agonists (FIG. 5C). Under physiological conditions, α-ADR dominates over β-ADR, leading to overall lipogenesis (28). Therefore, α-ADR inhibition by CST might have shifted the balance towards lipolysis.

In obese states, increased circulating leptin concentration causes desensitization of its receptors, resulting in failure of leptin to reduce food intake and promote lipid oxidation (49,50). In this context, the ability of CST to decrease leptin production and minimize chronic overexposure might have restored leptin sensitivity in brain and peripheral tissues. Therefore, the net result was increased oxidation of lipolytic product (NEFA). Leptin signaling through AMPK and STAT3 in Chga-KO mice following acute leptin treatment was subdued compared to WT. CST treatment restored leptin action in Chga-KO mice, suggesting re-sensitization of leptin receptor.

To further clarify the interactions between CST and leptin pathways and to establish CST as an anti-obesity factor, we examined the effects of CST in leptin resistant DIO mice and leptin deficient Ob/Ob mice. DIO mice are known to exhibit peripheral leptin resistance (54-56). We observed leptin resistance in adipose tissue explants from DIO mice where acute leptin treatment did not stimulate lipolysis, β-oxidation, or phosphorylation of Stat3 and AMPK. However, prior CST treatment of DIO mice for 16 days led to the sensitization of all acute leptin effects in the adipose tissue explants, suggesting sensitization of leptin receptor-like functions in adipose tissue. CST administration to DIO mice did not reduce food intake but caused modest reduction in body weight proportional to the loss of adipose mass. As a result, the products of lipolysis, glycerol and NEFA, were increased in serum.

Unlike DIO mice, leptin-deficient Ob/Ob mice maintain leptin sensitivity (57-60). As a result, acute treatment of adipose explants with leptin stimulated lipolysis, fatty acid oxidation, and phosphorylation of Stat3 and AMPK. The leptin effects were enhanced in the explants from CST treated Ob/Ob mice whereas CST treatment alone did not show significant peripheral effects. It should be noted that the treatment of Ob/Ob mice with CST for 16 days started to reduce food intake resembling a leptin-like effect. This is in contrast to DIO mice where CST treatment did not reduce food intake. One of the reasons for the failure of leptin to reduce food intake by activating hypothalamic leptin receptors in DIO mice is limited access to the circulating leptin through the blood brain barrier. When administered through the intracerebroventricular (i.c.v.) route, leptin could activate hypothalamic receptor signaling in DIO mice (54-56). It is therefore highly possible that like leptin, i.c.v. administration of CST might reduce food intake in DIO mice and enhance hypothalamic leptin response. Administration of CST to DIO mice by the i.p. route, on the other hand, could generate only peripheral response and improve peripheral leptin sensitivity. It is also possible that CST acted centrally in Ob/Ob mice to reduce food intake but it needed longer treatment period (6-8 weeks instead of 16 days) to initiate reduction of body weight and adipose tissue mass. We will address these possibilities in a future work. Restoration of leptin-mediated AMPK signaling and fatty acid oxidation in DIO mice by CST with concomitant reduction in body weight and fat mass suggests a crucial physiological role of CST in fine-tuning lipid metabolism to prevent obesity. We have also seen that CST stimulates lipolysis by antagonizing α-ADR functions.

References for Background and Example 1

1. Winkler, H., and Fischer-Colbrie, R. (1992) *Neuroscience* 49, 497-528
2. Taupenot, L., Harper, K. L., and O'Connor, D. T. (2003) *New Engl J Med* 348, 1134-1149
3. Montero-Hadjadje, M., Vaingankar, S., Elias, S., Tostivint, H., Mahata, S. K., and Anouar, Y. (2008) *Acta Physiol* (OxJ) 192, 309-324
4. Tatemoto, K., Efendic, S., Mutt, V., Makk, G., Feistner, G. J., and Barchas, J. D. (1986) *Nature* 324, 476-478
5. Sanchez-Margalet, V., Gonzalez-Yanes, C., Najib, S., and Santos-Alvarez, J. (2010) *Regul Pept* 161, 8-14
6. Aardal, S., Helle, K. B., Elsayed, S., Reed, R. K., and Serck-Hanssen, G. (1993) *J Neuroendocrinol* 5, 405-412
7. Mahata, S. K., O'Connor, D. T., Mahata, M., Yoo, S. H., Taupenot, L., Wu, H., Gill, B. M., and Parmer, R. J. (1997) *J Clin Invest* 100, 1623-1633
8. Mahapatra, N. R., O'Connor, D. T., Vaingankar, S. M., Sinha Hikim, A. P., Mahata, M., Ray, S., Staite, E., Wu, H., Gu, Y., Dalton, N., Kennedy, B. P., Ziegler, M. G., Ross, J., Jr., and Mahata, S. K. (2005) *J Clin Invest* 115, 1942-1952
9. Mahata, S. K., Mahata, M., Fung, M. M., and O'Connor, D. T. (2010) *Regul Pept* 162, 33-43
10. Theurl, M., Schgoer, W., Albrecht, K., Jeschke, J., Egger, M., Beer, A. G., Vasiljevic, D., Rong, S., Wolf, A. M., Bahlmann, F. H., Patsch, J. R., Wolf, D., Schratzberger, P., Mahata, S. K., and Kirchmair, R. (2010) *Circ Res* 107, 1326-1335
11. Fung, M. M., Salem, R. M., Mehtani, P., Thomas, B., Lu, C. F., Perez, B., Rao, F., Stridsberg, M., Ziegler, M. G., Mahata, S. K., and O'Connor, D. T. (2010) *Clin Exp Hypertens* 32, 278-287
12. Gaede, A. H., and Pilowsky, P. M. (2012) *Am J Physiol Regul Integr Comp Physiol* 302, R365-72
13. Angelone, T., Quintieri, A. M., Brar, B. K., Limchaiyawat, P. T., Tota, B., Mahata, S. K., and Cerra, M. C. (2008) *Endocrinology* 149, 4780-4793
14. Mazza, R., Gattuso, A., Mannarino, C., Brar, B. K., Barbieri, S. F., Tota, B., and Mahata, S. K. (2008) *Am J Physiol Heart Circ Physiol* 295, H113-122
15. Imbrogno, S., Garofalo, F., Cerra, M. C., Mahata, S. K., and Tota, B. (2010) *J Exp Biol* 213, 3636-3643
16. Gayen, J. R., Gu, Y., O'Connor, D. T., and Mahata, S. K. (2009) *Endocrinology* 150, 5027-5035
17. Gaede, A. H., and Pilowsky, P. M. (2010) *Am J Physiol Regul Integr Comp Physiol* 299, R1538-1545
18. Dev, N. B., Gayen, J. R., O'Connor, D. T., and Mahata, S. K. (2010) *Endocrinology* 151, 2760-2768
19. Briolat, J., Wu, S. D., Mahata, S. K., Gonthier, B., Bagnard, D., Chasserot-Golaz, S., Helle, K. B., Aunis, D., and Metz-Boutigue, M. H. (2005) *Cell Mol Life Sci* 62, 377-385
20. Radek, K. A., Lopez-Garcia, B., Hupe, M., Niesman, I. R., Elias, P. M., Taupenot, L., Mahata, S. K., O'Connor, D. T., and Gallo, R. L. (2008) *J Invest Dermatol* 128, 1525-1534
21. Aung, G., Niyonsaba, F., Ushio, H., Kajiwara, N., Saito, H., Ikeda, S., Ogawa, H., and Okumura, K. (2011) *Immunology* 132, 527-539
22. Guo, X., Zhou, C., and Sun, N. (2011) *Biochem Biophys Res Commun* 407, 807-812
23. Egger, M., Beer, A. G., Theurl, M., Schgoer, W., Hotter, B., Tatarczyk, T., Vasiljevic, D., Frauscher, S., Marksteiner, J., Patsch, J. R., Schratzberger, P., Djanani, A. M., Mahata, S. K., and Kirchmair, R. (2008) *Eur J Pharmacol* 598, 104-111
24. Sugawara, M., Resende, J. M., Moraes, C. M., Marquette, A., Chich, J. F., Metz-Boutigue, M. H., and Bechinger, B. (2010) *FASEB J* 24, 1737-1746
25. Helle, K. B. (2010) *Cardiovasc Res* 85, 9-16
26. Arner, P. (1999) *Int J Obes Relat Metab Disord* 23 Suppl 1, 10-13
27. Arner, P. (2005) *Best Pract Res Clin Endocrinol Metab* 19, 471-482
28. Lafontan, M., Barbe, P., Galitzky, J., Tavernier, G., Langin, D., Carpene, C., Bousquet-Melou, A., and Berlan, M. (1997) *Hum Reprod* 12 Suppl 1, 6-20
29. Stich, V., de Glisezinski, I., Crampes, F., Suljkovicova, H., Galitzky, J., Riviere, D., Hejnova, J., Lafontan, M., and Berlan, M. (1999) *Am J Physiol* 277, R1076-1083
30. Stich, V., Pelikanova, T., Wohl, P., Sengenes, C., Zakaroff-Girard, A., Lafontan, M., and Berlan, M. (2003) *Am J Physiol Endocrinol Metab* 285, E599-607
31. Lafontan, M., and Langin, D. (2009) *Prog Lipid Res* 48, 275-297
32. Mori, S., Nojiri, H., Yoshizuka, N., and Takema, Y. (2007) *Lipids* 42, 307-314
33. Jensen, M. D. (1997) *Annu Rev Nutr* 17, 127-139
34. Bougneres, P., Stunff, C. L., Pecqueur, C., Pinglier, E., Adnot, P., and Ricquier, D. (1997) *J Clin Invest* 99, 2568-2573
35. Lafontan, M., and Berlan, M. (1993) *J Lipid Res* 34, 1057-1091
36. Townsend, R. R., Klein, S., and Wolfe, R. R. (1994) *Am J Physiol* 266, E155-160
37. Stallknecht, B., Bulow, J., Frandsen, E., and Galbo, H. (1997) *J Physiol* 500 (Pt 1), 271-282
38. Gayen, J. R., Saberi, M., Schenk, S., Biswas, N., Vaingankar, S. M., Cheung, W. W., Najjar, S. M., O'Connor, D. T., Bandyopadhyay, G., and Mahata, S. K. (2009) *J Biol Chem* 284, 28498-28509
39. Fritsche, A., Wahl, H. G., Metzinger, E., Renn, W., Kellerer, M., Haring, H., and Stumvoll, M. (1998) *Exp Clin Endocrinol Diabetes* 106, 415-418
40. Scriba, D., Aprath-Husmann, I., Blum, W. F., and Hauner, H. (2000) *Eur J Endocrinol* 143, 439-445
41. Couillard, C., Mauriege, P., Prud'homme, D., Nadeau, A., Tremblay, A., Bouchard, C., and Despres, J. P. (2002) *Obesity Res* 10, 6-13
42. Thalmann, S., Juge-Aubry, C. E., and Meier, C. A. (2008) *Methods Mol Biol* 456, 195-199
43. Karnieli, E., Zarnowski, M. J., Hissin, P. J., Simpson, I. A., Salans, L. B., and Cushman, S. W. (1981) *J Biol Chem* 256, 4772-4777
44. Bandyopadhyay, G. K., Yu, J. G., Ofrecio, J., and Olefsky, J. M. (2005) *Diabetes* 54, 2351-2359
45. Bandyopadhyay, G. K., Yu, J. G., Ofrecio, J., and Olefsky, J. M. (2006) *Diabetes* 55, 2277-2285
46. Mao, X., Kikani, C. K., Riojas, R. A., Langlais, P., Wang, L., Ramos, F. J., Fang, Q., Christ-Roberts, C. Y., Hong, J. Y., Kim, R. Y., Liu, F., and Dong, L. Q. (2006) *Nat Cell Biol* 8, 516-523
47. Seeley, R. J., van Dijk, G., Campfield, L. A., Smith, F. J., Burn, P., Nelligan, J. A., Bell, S. M., Baskin, D. G., Woods, S. C., and Schwartz, M. W. (1996) *Horm Metab Res* 28, 664-668
48. Minokoshi, Y., Kim, Y. B., Peroni, O. D., Fryer, L. G., Muller, C., Carling, D., and Kahn, B. B. (2002) *Nature* 415, 339-343
49. Wang, M. Y., Orci, L., Ravazzola, M., and Unger, R. H. (2005) *Proc Natl Acad Sci USA* 102, 18011-18016
50. Knight, Z. A., Hannan, K. S., Greenberg, M. L., and Friedman, J. M. (2010) *PloS one* 5, e1376
51. Kim, Y. B., Uotani, S., Pierroz, D. D., Flier, J. S., and Kahn, B. B. (2000) *Endocrinology* 141, 2328-2339
52. Morris, D. L., and Rui, L. (2009) *Am J Physiol Endo Metab* 297, E1247-1259
53. Vaisse, C., Halaas, J. L., Horvath, C. M., Darnell, J. E., Jr., Stoffel, M., and Friedman, J. M. (1996) *Nat Genet* 14, 95-97
54. El-Haschimi, K., Pierroz, D. D., Hileman, S. M., Bjorbaek, C., and Flier, J. S. (2000) *J Clin Invest* 105, 1827-1832
55. Lin, S., Thomas, T. C., Storlien, L. H., and Huang, X. F. (2000) *Int J Obes Relat Metab Disord* 24, 639-646
56. Van Heek, M., Compton, D. S., France, C. F., Tedesco, R. P., Fawzi, A. B., Graziano, M. P., Sybertz, E. J., Strader, C. D., and Davis, H. R., Jr. (1997) *J Clin Invest* 99, 385-390
57. Pelleymounter, M. A., Cullen, M. J., Baker, M. B., Hecht, R., Winters, D., Boone, T., and Collins, F. (1995) *Science* 269, 540-543
58. Koch, C., Augustine, R. A., Steger, J., Ganjam, G. K., Benzler, J., Pracht, C., Lowe, C., Schwartz, M. W., Shepherd, P. R., Anderson, G. M., Grattan, D. R., and Tups, A. (2010) *J Neurosci* 30, 16180-16187
59. Fruhbeck, G., Aguado, M., and Martinez, J. A. (1997) *Biochem Biophys Res Commun* 240, 590-594
60. Fruhbeck, G., Aguado, M., Gomez-Ambrosi, J., and Martinez, J. A. (1998) *Biochem Biophys Res Commun* 250, 99-102
61. Mahata, S. K., Mahata, M., Wakade, A. R., and O'Connor, D. T. (2000) *Mol Endocrinol* 14, 1525-1535
62. Mahata, S. K., Mahata, M., Wen, G., Wong, W. B., Mahapatra, N. R., Hamilton, B. A., and O'Connor, D. T. (2004) *Mol Pharmacol* 66, 1180-1191
63. Gomez-Ambrosi, J., Fruhbeck, G., Aguado, M., Milagro, F. I., Margareto, J., and Martinez, A. J. (2001) *Int J Mol Med* 8, 103-109
64. Polak, J., Moro, C., Bessiere, D., Hejnova, J., Marques, M. A., Bajzova, M., Lafontan, M., Crampes, F., Berlan, M., and Stich, V. (2007) *J Lipid Res* 48, 2236-2246

Example 2

In this example, we continue to study the physiological and molecular consequence of supplementing catestatin (CST) in our mouse knockout model of chromogranin A in which all chromogranin A-derived peptides are absent including pancreastatin, vasostatin and catestatin in the Chga-KO mouse. In addition, we created a knockout mouse in which only CST peptide is lacking from the knockout animal, CST-KO mouse, while the other CHGA-derived peptides, such as PST and vasostatin are present.

CST Acts as an Insulin-Sensitizing Peptide.

In studying insulin sensitivity, we found chromogranin A (human CHGA/mouse Chga) knockout (Chga-KO) mice to be sensitive to insulin (1) and such sensitivity was protected even after high fat diet (HFD: 60%) induced resistance to insulin (unpublished data). Supplementation of anti-insulin pancreastatin (PST: $CHGA_{250-301}$) to HFD-fed Chga-KO mice reversed the phenotype implying that deficiency of pancreastatin (PST: $CHGA_{250-301}$) and not the deficiency of anti-hypertensive and anti-obese catestatin (CST: $CHGA_{352-372}$) was responsible for the hypersensitivity to insulin. As opposed to PST, CST supplementation made HFD-fed Chga-KO mice sensitive to insulin as shown by glucose tolerance test (GTT) implicating CST as an insulin-sensitizing peptide. The phenotype of adult CST domain-specific knockout (CST-KO) mice (where PST is expressed) is opposite to Chga-KO mice in being insulin resistant (as shown by insulin tolerance test (ITT)) and supplementation of CST to CST-KO mice improved insulin sensitivity (see in FIGS. 11G & 12D).

Figure 11:
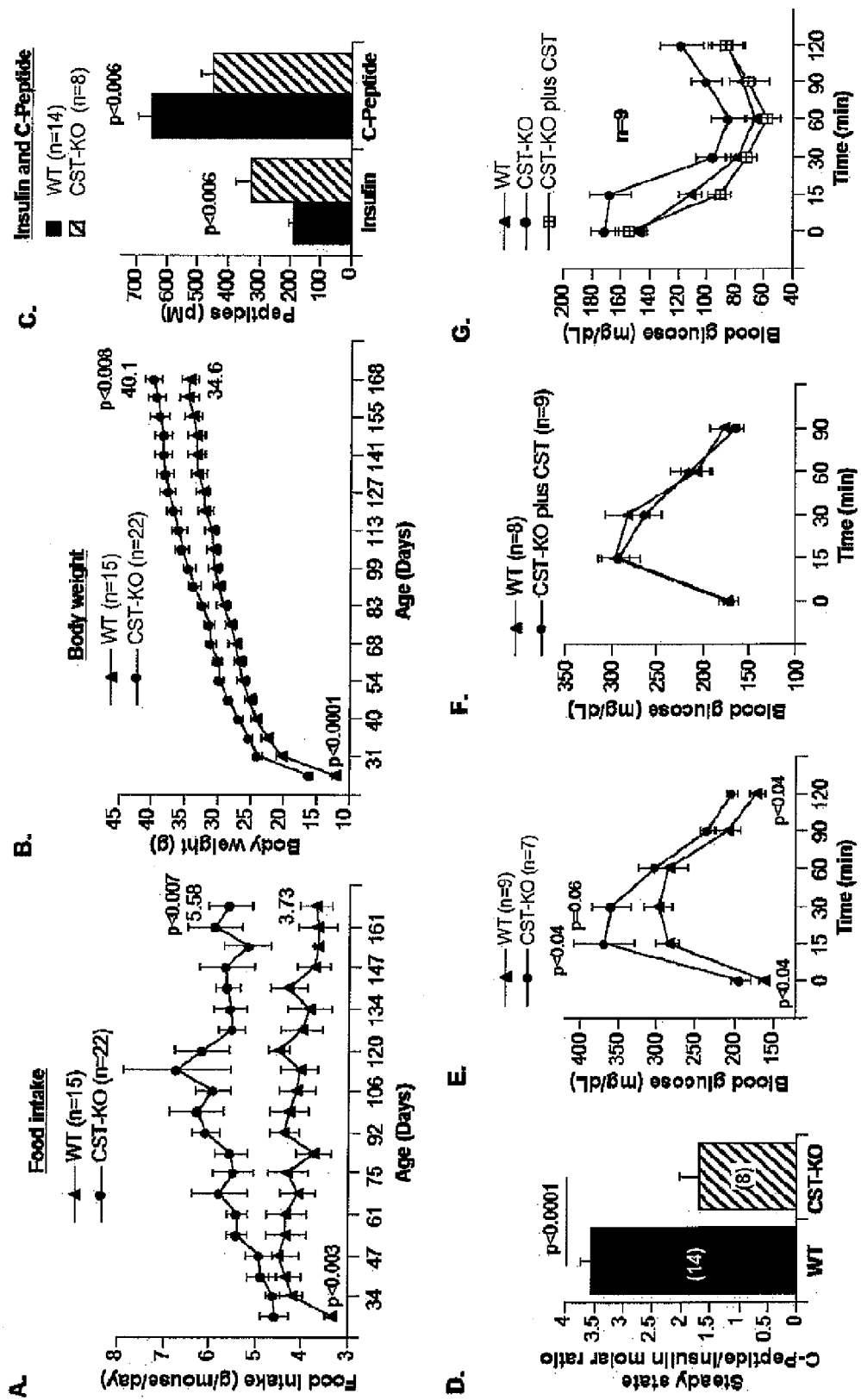
FIG. 11. Metabolic phenotypes in NCD-fed CST-KO mice. (A) CST-KO mice eat more food than WT. (B) CST-KO mice are heavier than WT. (C) While lower level plasma C-Peptide in CST-KO mice indicates decreased insulin secretion but higher plasma insulin is indicative of dampened insulin clearance by liver as supported by diminished C-Peptide/insulin molar ratio (D). IP-GTT showed insulin resistance in CST-KO mice (E). CST supplementation improved insulin resistance in CST-KO mice as shown by IP-GTT (F) and IP-ITT (G).

1. CST-KO Mice are Insulin Resistant:

Like Chga-KO mice, CST-KO mice are obese with increased body weight (52.45 g vs 47.88 g, p<0.02) and food intake (3.37 g vs 2.26 g, p<0.03) compared to WT mice (FIGS. 11A & 11B). Basal insulin level of CST-KO mice was higher than WT mice but most interestingly increased insulin level in CST-KO mice was not accompanied with increased C-peptide level (FIG. 11C). In fact, both plasma C-peptide concentration and C-peptide/Insulin molar ratio in CST-KO mice were lower than WT mice (FIGS. 11C&11D) implicating (i) decreased insulin secretion as well as (ii) defective hepatic clearance in CST-KO mice resulting in an overall higher concentration of plasma insulin. CST-KO mice became glucose intolerant at ~6 months of age as shown by intraperitoneal glucose tolerance test (IP-GTT: FIG. 11E) and intraperitoneal insulin tolerance test (IP-ITT: 1G). Supplementation of CST to CST-KO mice restored glucose tolerance as shown by IP-GTT (FIG. 11F) & IP-ITT (FIG. 11G).

Figure 12:
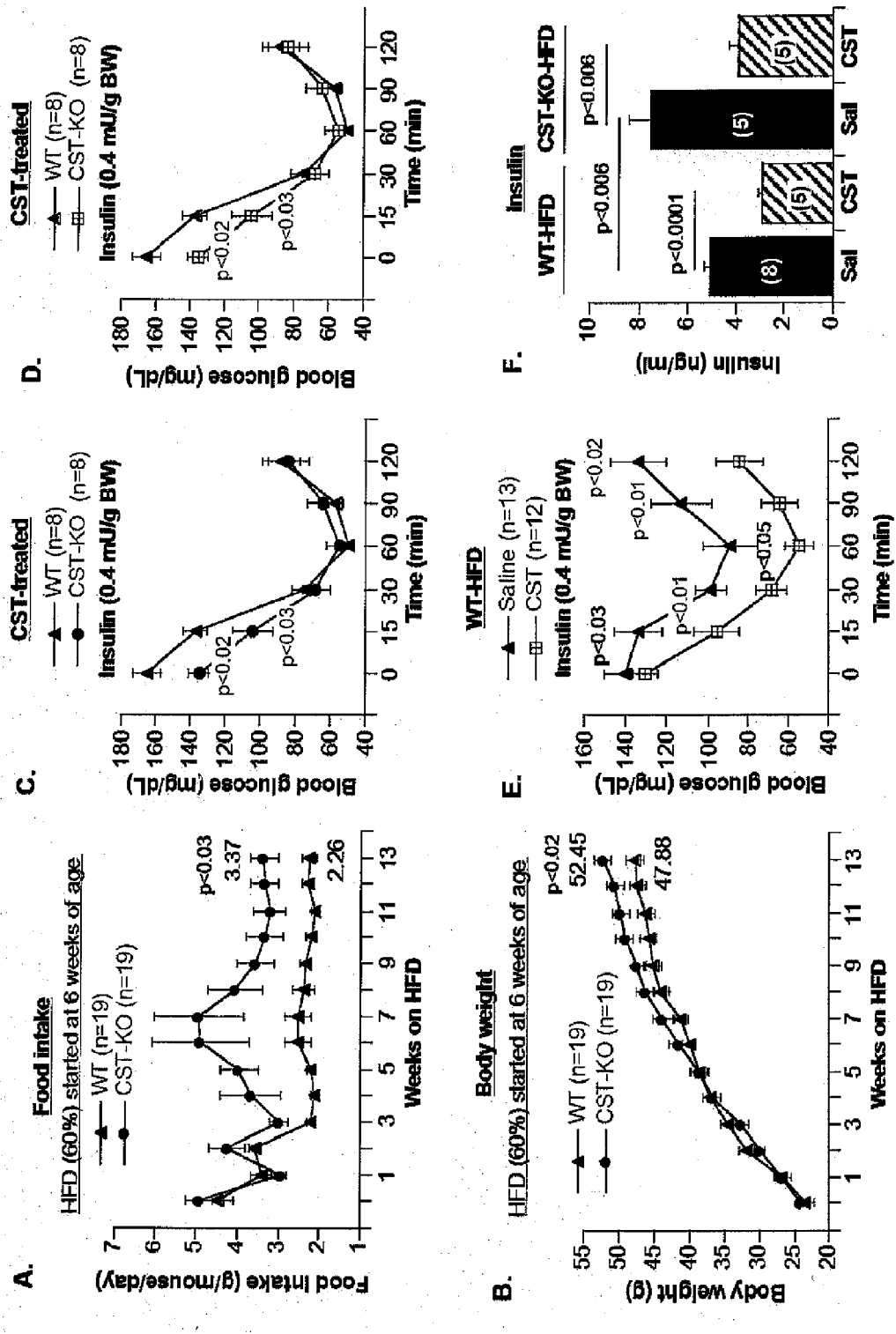
FIG. 12. Metabolic phenotypes in HFD-fed CST-KO mice. (A) CST-KO mice eat more 60% HFD than WT. (B) CST-KO mice gained more weight than WT. (C) Heightened glucose resistance at baseline in CST-KO mice compared to WT mice. (D) CST (5 μg/g BW) supplementation in CST-KO mice reversed glucose resistance to glucose tolerance. (E) CST caused HFD-fed WT mice sensitive to insulin. (F) CST reduced hyperinsulinemia in both WT and CST-KO mice implicating CST as an insulin sensitizing peptide. Figures in parentheses indicate number of animals.
Figure 13:
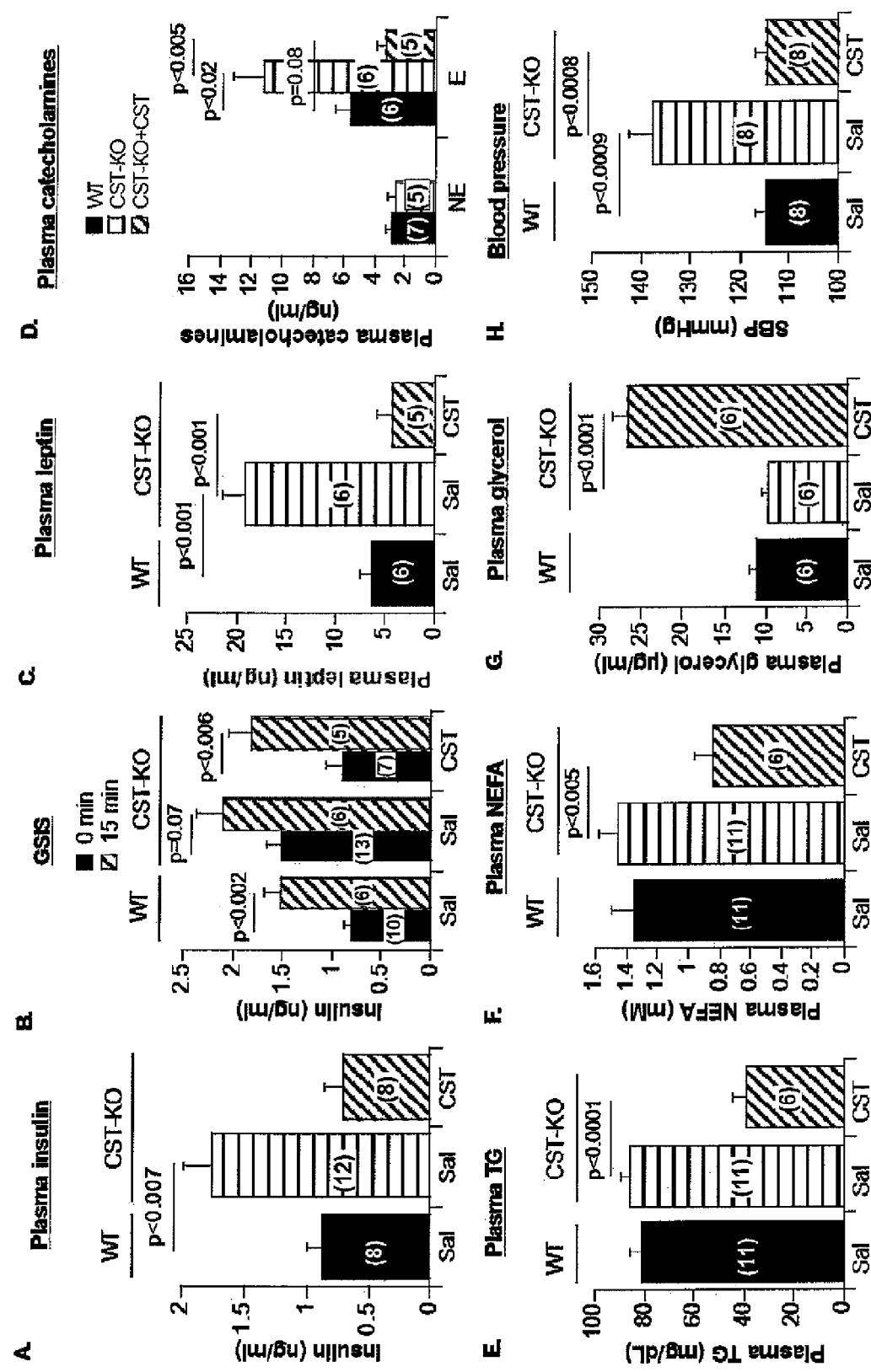
FIG. 13. Changes in biochemical and physiological parameters in NCD-fed CST-KO mice after CST (5 μg/g BW) supplementation. (A) CST normalized hyperinsulinemia in CST-KO mice. (B) Despite hyperinsulinemia GSIS showed further increase (statistically insignificant) in insulin level in CST-KO mice. (C) CST supplementation normalized hyperleptinemia in CST-KO mice. (D) CST normalized high plasma catecholamines in CST-KO mice. CST supplementation in CST-KO mice decreased both plasma TG (E) and NEFA (F), increased plasma glycerol (G) and normalized increased plasma catecholamines in CST-KO mice (H). Figures in parentheses indicate number of animals.

2. CST Treatment Improved Insulin Sensitivity in HFD-Fed WT as Well as in CST-KO Mice:

CST-KO mice eat more HFD and gained more weight than WT mice (FIGS. 12A&12B). As expected, HFD-fed CST-KO mice showed increased insulin resistance (FIG. 12C) but supplementation of CST improved insulin sensitivity as shown by IP-ITT (FIG. 12D). CST-induced improvement in insulin sensitivity in HFD-fed WT mice (FIG. 12E) reinforced this insulin sensitizing effect of CST. Consistent with this finding, CST decreased basal plasma insulin levels in both HFD-fed WT mice and HFD-fed CST-KO mice (FIG. 12F). At ~6 months of age, CST-KO mice became glucose intolerant with higher plasma insulin and leptin levels (FIG. 13A-13C). Glucose intolerance in spite of higher fasting basal insulin levels implied development of insulin resistance in CST-KO mice. Interestingly, CST-KO mice did not exhibit higher plasma triglycerides (TG) or non-esterified fatty acids (NEFA) levels indicating that these mice are at least not hyperlipidemic (FIG. 13E-13G). CST (5 µg/g BW) treatment of CST-KO mice for 8 days improved glucose tolerance (FIGS. 11F&11G), reduced plasma insulin, leptin, catecholamine, TG or NEFA levels with concomitant increase in glycerol level (FIG. 13C-13G). These findings indicate that (i) CST-mediated lipolysis was not mediated by leptin or catecholamine (which were already at higher level in CST-KO mice but decreased after CST treatment), and (ii) the released fatty acids were not accumulated in plasma but most likely taken up by liver and adipose tissues where they undergo re-esterification and storage. During ITT, resistance against change in glucose level after first 15 min may indicate that inhibition of glycogen breakdown by insulin might have been resisted by the presence of high catecholamines (FIG. 11G). Like Chga-KO mice, CST-KO mice are hyperadrenergic (FIG. 13D) and hypertensive (FIG. 13H), which was normalized by CST supplementation.

3. CST Enhanced Lipid Oxidation in Liver and Muscle but Suppressed Expression of Genes for Lipogenic and Gluconeogenic Genes in Liver.

Figure 14:
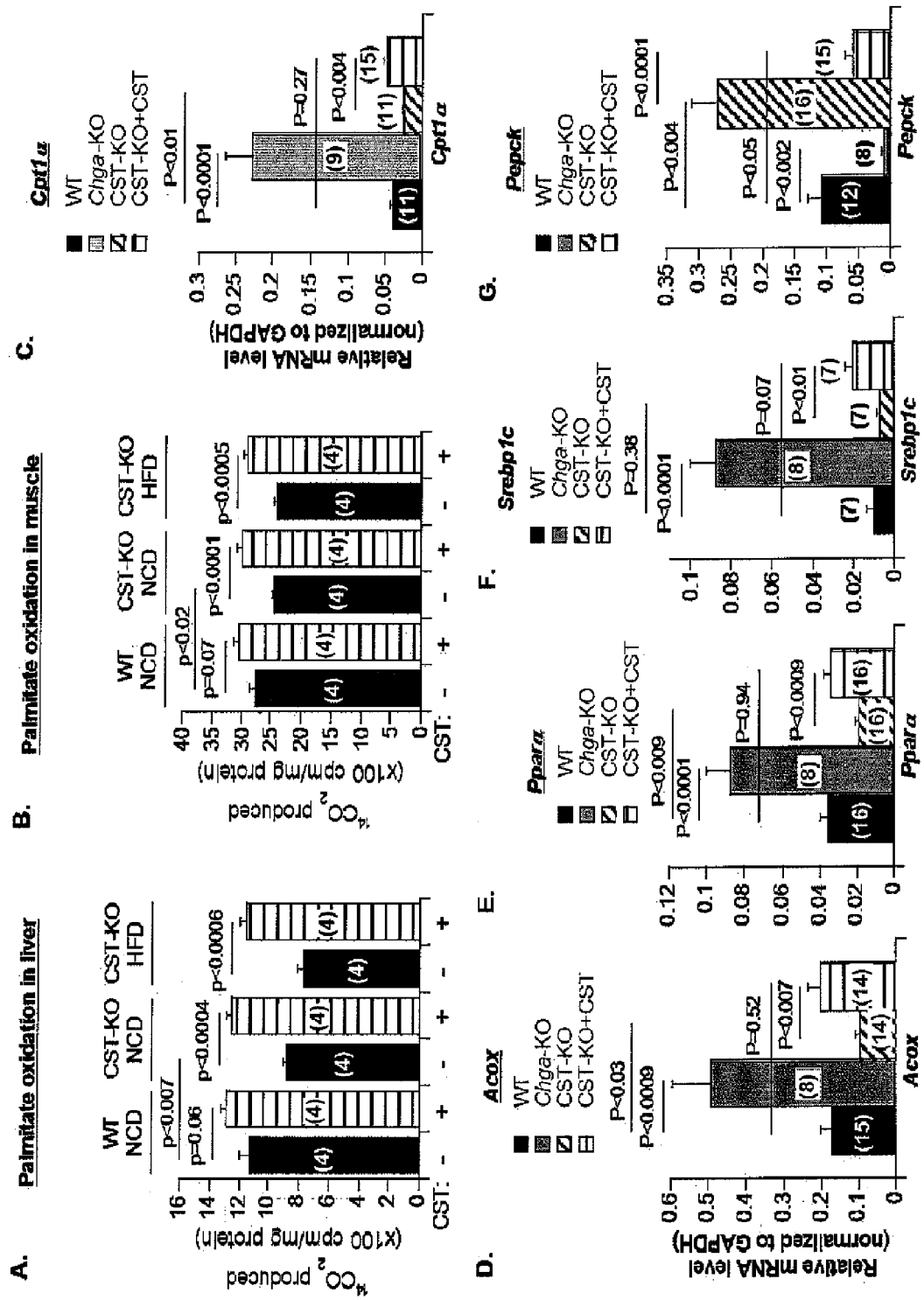
FIG. 14. Palmitate oxidation. CST augmented palmitate oxidation in liver (A) and muscle (B) of both NCD- and 60% HFD-fed mice. Hepatic expression of genes involved in fatty acid oxidation such as Cpt1α(C), Acox (D) and Pparα (E). Augmented expression of these genes in Chga-KO mice indicates increased fatty acid oxidation in liver. In contrast, decreased expression in CST-KO mice indicates decreased fatty acid oxidation in liver, which was restored by supplementation with CST. Expression of lipogenic & gluconeogenic genes (F). Increased expression of Srebp1c in Chga-KO mice indicates increased lipogenesis. (G) Decreased expression of gluconeogenic gene Pepck in Chga-KO mice indicates inhibition of gluconeogenesis eventuating in increased sensitivity to insulin. In contrast, augmented expression of Pepck in CST-KO implicates increased gluconeogenesis eventuating in decreased sensitivity to insulin, which is normalized after CST supplementation. Figures in parentheses indicate number of animals.

CST stimulated palmitate oxidation in liver and muscle (FIGS. 14A&14B) in CST-KO mice. In this conjunction, CST also stimulated expression of genes for carnitine palmitoyl transferase-1alpha (Cpt1α), acyl CoA oxidase (Acox) and peroxisome proliferators-activated receptor alpha (Pparα) and sterol response element binding protein 1c (Srebp1c) but suppressed the expression of phosphoenolpyruvate carboxykinase (Pepck) in liver of CST-KO mice (FIG. 14C-14G). With respect to lipid metabolism in CST-KO mice, gene expression analysis suggests that in contrast to Chga-KO mice, CST-KO mice are not prone to lipid oxidation (FIG. 14C-14E). The oxidation of palmitic acid in liver and muscle homogenates from CST-KO mice was lower than WT tissues but the supplementation with CST corrected these defects (FIGS. 14A&14B). Corroborating with the metabolic data, the analysis of mRNA expressions of genes involved in fatty acid oxidation such as Cpt1α, Acox and Pparα exhibited reduced expressions in CST-KO mice but increased expression after CST treatment (FIG. 14C-14E). In terms of expression of lipogenic gene such as Srebp1c, Chga-KO and CST-KO mice offered interesting and contrasting examples (FIG. 14F). While Chga-KO mice displayed strong activities for both lipid oxidation and lipogenesis (1), CST-KO mice showed opposite characteristics yet both are obese compared to WT mice. However, obesity in Chga-KO mice is much more prominent than CST-KO mice (22-25% more gain in weight in Chga-KO mice versus 10-12% gain in CST-KO mice when compared to WT mice in 4 months). As reported previously by us (1, 2), lipogenesis in Chga-KO leads to huge expansion of adipose tissue (25-30% gain in adipose tissue weight) without additional lipid accumulation in blood or liver. In comparison, increase in adipose mass in CST-KO mice is mild (<10%). It appears that in spite of elevated level of lipogenesis in Chga-KO mice, high lipid oxidation and re-esterification of fatty acids within the tissues prevented lipid accumulation in blood and liver whereas low lipogenesis and efficient re-esterification in CST-KO mice prevented lipid accumulation in blood and liver. An important correlation to be noted here is that increased Srebp1c expression in liver can also cause suppression of Pepck and glucose-6-phosphatase (G6pase) expression leading to inhibition of gluconeogenesis (7). Therefore, it is quite possible that increased Srebp1c in Chga-KO mice elevated lipid accumulation in adipose tissue but attenuated gluconeogenesis thus contributing to insulin sensitivity whereas the opposite may be true for CST-KO mice (FIG. 14F). The finding that CST elevated expression of Srebp1c in CST-KO mice (FIG. 14F) also correlated well with the gain in insulin sensitivity in CST-KO mice after CST treatment. In this context, CST also suppressed Pepck expression in CST-KO liver (FIG. 14G).

4. Role of CST in Insulin Clearance: CST Stimulated Insulin Secretion in Culture in a Glucose-Independent Manner but Suppressed Plasma Insulin Level In Vivo Due to Increased Clearance.

Compared to WT mice, CST-KO mice are hyperinsulinemic but CST supplementation normalized the plasma insulin concentration to the WT level (FIG. 13A). Glucose-stimulated insulin secretion (GSIS) analysis showed that despite higher basal insulin, glucose challenge in CST-KO mice did further increase in insulin level but not to the extent of statistical significance (FIG. 13B). These results implied that in vivo CST might enhance insulin clearance thus bringing down the circulating insulin level. It should be noted here that while the plasma concentration of insulin in CST-KO mice was elevated, plasma C-peptide concentration remained unaltered (FIG. 11C), suggesting that insulin secretion did not contribute to attainment of higher plasma insulin level. Therefore, the rise in plasma insulin concentration in CST-KO mice might be due to the diminished hepatic clearance in the absence of CST and not due to increased secretion.

5. CST Improved Glucose Tolerance and Insulin Clearance in Diabetic Db/Db Mice.

Figure 15:
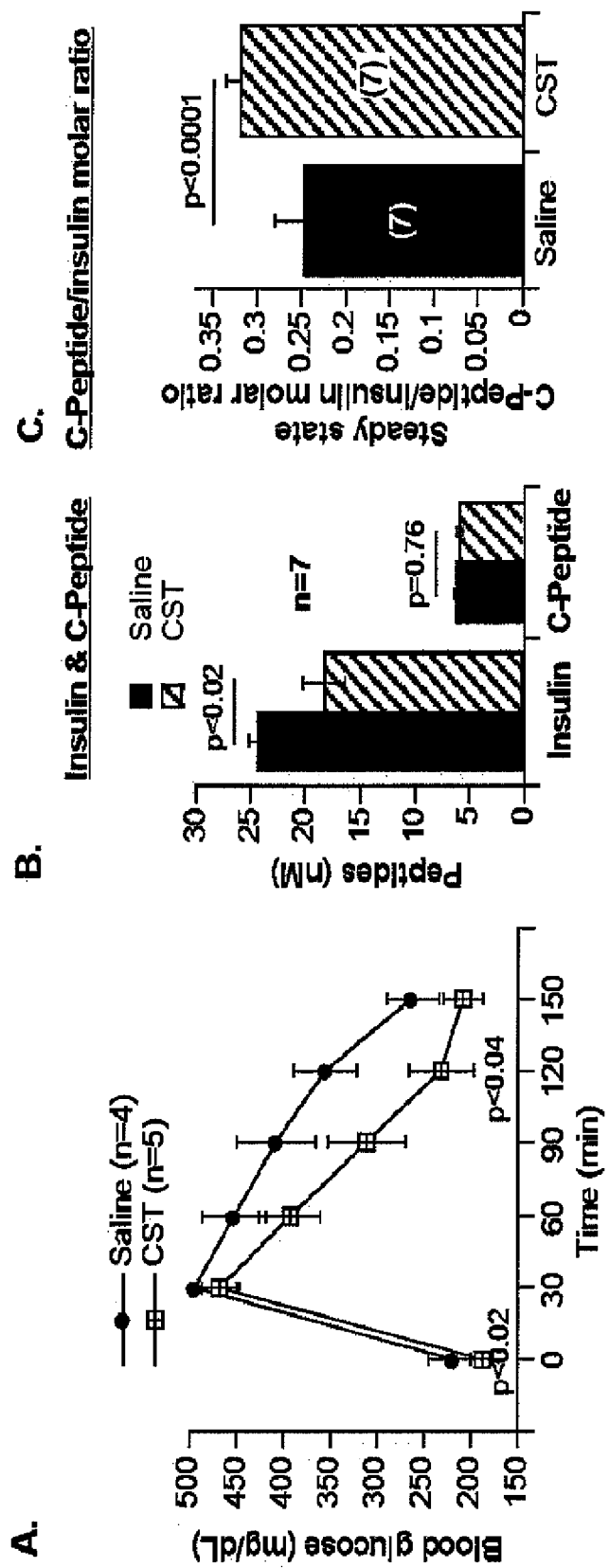
FIG. 15. CST (10 μg/g BW for 14 days) resulted in improved glucose tolerance (A) and decreased plasma insulin level (B) in db/db mice, No change in C-Peptide level (B) and higher C-Peptide/insulin molar ratio (C) in response to CST indicate that CST might have increased insulin clearance by the liver. Figures in parentheses indicate number of animals.

GTT after 14 days of treatment of db/db mice with CST (10 µg/g/day) showed improvement in glucose tolerance (FIG. 15A). Since db/db mice do not have functional long form of Ob-Rb, and our hypothesis requires functional Ob-R for CST action, one intriguing question that needs to be answered is how does CST act in db/db mice? Our hypothesis is that the short form of leptin receptor (Ob-Ra), present in db/db mice and active in presence of abundant amount of leptin available in db/db mice, is responsible for the diabetic and hypertensive phenotypes. CST may prevent Ob-Ra actions and restores blood pressure and glucose homeostasis. Plasma insulin level in db/db mice is very high (20-30 nM) compared to C57BL/6 mice (0.1-1.7 nM). Treatment with CST for 14 days reduced insulin level to 14-18 nM without lowering C-peptide levels (FIG. 15B). As a result, C-peptide/Insulin molar ration increased after CST treatment (FIG. 15C). These results suggest that CST might have increased clearance of insulin in db/db mice.

6. CST-Equivalent: Retro-Inverso CST Peptide (RI-CST) is Functional and Long-Acting.

Figure 16:
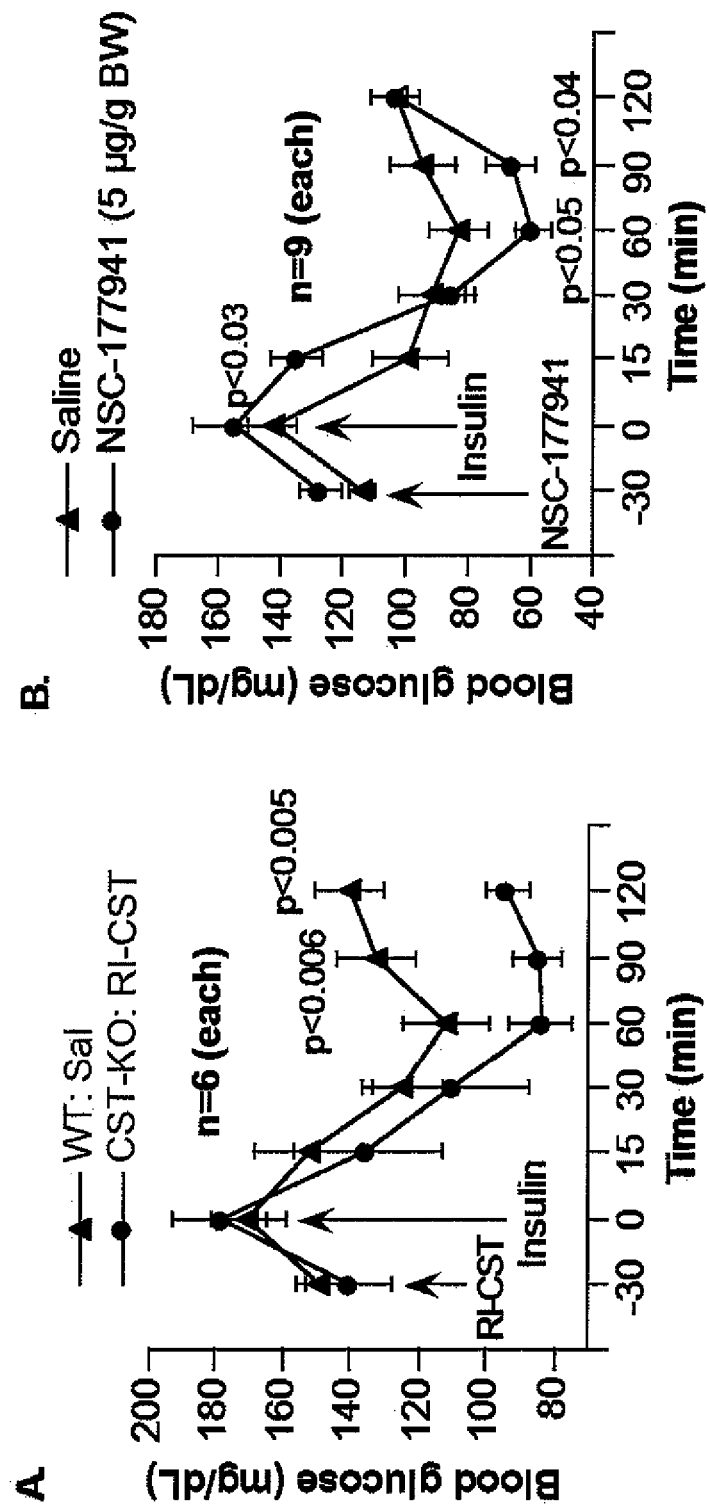
FIG. 16. Improvement in insulin sensitivity in NCD-fed CST-KO mice after treatment with a CST equivalent peptide (RI-CST) (A) or a non-peptide CST-mimetic compound (RSC-177941) during ITT (insulin: 0.4 mU/g BW). Figures in parentheses indicate number of animals.
Figure 17:
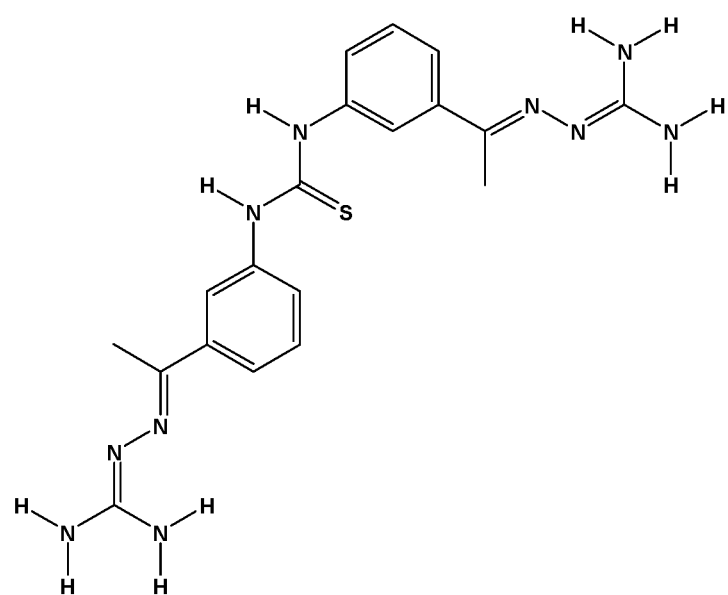 [SMILES: C/C(=N\N=C(N)N)c1cccc(NC(=S)Nc2cccc(/C(C)=N/N=C(N)N)c2)c1]
FIG. 17. Structure of NSC-177941 or CID177941 or CHEMBL177941

The amino acid sequence in RI-CST peptide is retro-inverted, in which the CST sequence is reversed such that the carboxyl terminal amino acid sequence is at the amino terminus and the amino terminal sequence at the carboxy terminus. In addition, the chirality is inverted by replacing L-amino acid with D-amino acid except in the case of glycine which is achiral. The RI-CST peptide, reverse sequence with inverted chirality due to substitution with D-amino acid, shows limited proteolytic degradation and has longer life in vivo. While CST was susceptible to complete protease degradation, RI-CST was found to be fairly resistant (8). What is unique in our finding is that like native CST peptide, RI-CST peptide was also functional in reducing SBP in hypertensive Chga-KO mice (8) and increasing sensitivity to insulin in CST-KO mice (FIG. 16A). Because of its expected longer half-life, RI-CST was able to suppress BP for longer period (>8 hrs) compared to CST (8). In ITT and GTT experiments, CST-KO mice showed insulin resistance for the first 15-30 min post glucose or insulin administration (FIGS. 11D, 11E&11G). The administration of CST and leptin to CST-KO mice improved insulin sensitivity. Thus, RI-CST also acts like CST (FIG. 16A).

7. CST-Mimetic Non-Peptide Compound NSC-177941 or CID177941 or CHEMBL177941 {IUPAC Name: 1,3-Bis[3-[(E)-N-(Diaminomethyllideneamino)-C-Methylcarbonimi-doyl]Phenyl]Thiourea} Also Increased Insulin Sensitivity.

While screening for structural analogs of CST that might reduce blood pressure, we came across a small non-peptide organic molecules in the database of NCI (National Cancer Institute) Development Therapeutics Program, which mimicked CST action like the RI-CST by reducing blood pressure. This compound is called Etalocib (leukotriene LTB4 receptor inhibitor). Jobson et al. found NSC-177941 to be inactive for inhibition of Chk2 protein kinase activity (9). We carried out ITT in insulin resistant CST-KO mice in presence or absence of NSC-177941 (FIG. 16B). Comparing with the results shown in FIG. 11G (with native CST) and in FIG. 15B (with RI-CST), it appeared that NSC-177941 was ineffective for the first 30 min and then showed a transient increase in insulin sensitivity between 30-90 minutes (FIG. 16B). This profile is significantly different from the results obtained with native CST or RI-CST where the increase in sensitivity was seen within 15 min after insulin injection and the effect persisted throughout the experimental period (FIG. 11G & FIG. 16A). Nevertheless, the compound NSC-177941 did affect insulin sensitivity.

Example 3

Scheme 1

Figure 18:
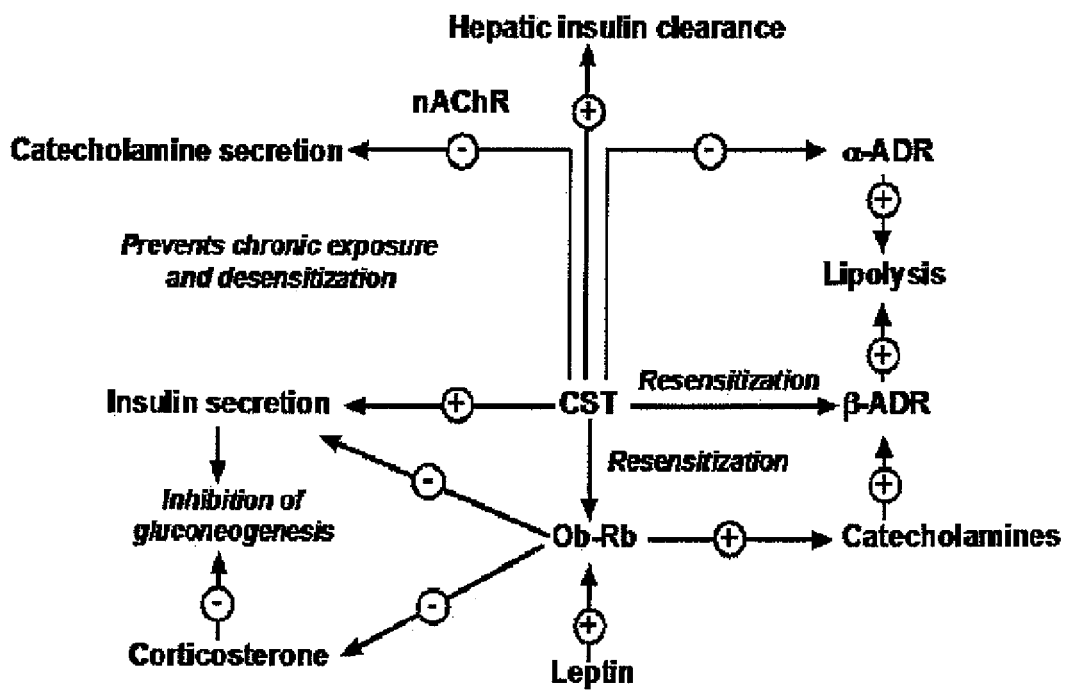
FIG. 18. CST regulation of key endocrine functions.

(FIG. 18) is a working model of CST regulation of key endocrine functions in part through modulation of leptin receptor (Ob-R) and adrenergic receptor (ADR) and is supported by examples 1 and 2. Computer-assisted sequence alignment and molecular dynamics (MD) simulations of Leptin and CST followed by extensive protein-protein docking studies revealed potential interaction of CST with the Ob-R. Analysis of structures of leptin and CST showed that these two molecules are capable of binding to the same domain (Ig-like domain) of Ob-R. This means, CST could compete with leptin and may also exhibit partial leptin-like agonist activity.

References for Examples 2 and 3

1. Gayen, J. R., Saberi, M., Schenk, S., Biswas, N., Vaingankar, S. M., Cheung, W. W., Najjar, S. M., O'Connor, D. T., Bandyopadhyay, G., and Mahata, S. K. 2009. A novel pathway of insulin sensitivity in chromogranin a null mice: A crucial role for pancreastatin in glucose homeostasis. *J Biol Chem* 284:28498-28509.

2. Bandyopadhyay, G. K., Vu, C. U., Gentile, S., Lee, H., Biswas, N., Chi, N. W., O'Connor, D. T., and Mahata, S. K. 2012. Catestatin (chromogranin A(352-372)) and novel effects on mobilization of fat from adipose tissue through regulation of adrenergic and leptin signaling. *The Journal of biological chemistry* 287:23141-23151.

3. Mahata, S. K., O'Connor, D. T., Mahata, M., Yoo, S. H., Taupenot, L., Wu, H., Gill, B. M., and Parmer, R. J. 1997. Novel autocrine feedback control of catecholamine release. A discrete chromogranin A fragment is a non-competitive nicotinic cholinergic antagonist. *J Clin Invest* 100:1623-1633.

4. Mahata, S. K., Mahata, M., Wakade, A. R., and O'Connor, D. T. 2000. Primary structure and function of the catecholamine release inhibitory peptide catestatin (chromogranin A344-364): Identification of amino acid residues crucial for activity. *Mol Endocrinol* 14:1525-1535.

5. Mahata, S. K., Mahata, M., Fung, M. M., and O'Connor, D. T. 2010. Catestatin: a multifunctional peptide from chromogranin A. *Regul Pept* 162:33-43.

6. Angelone, T., Quintieri, A. M., Brar, B. K., Limchaiyawat, P. T., Tota, B., Mahata, S. K., and Cerra, M. C. 2008. The antihypertensive chromogranin a peptide catestatin acts as a novel endocrine/paracrine modulator of cardiac inotropism and lusitropism. *Endocrinology* 149:4780-4793.

7. Yamamoto, T., Shimano, H., Nakagawa, Y., Ide, T., Yahagi, N., Matsuzaka, T., Nakakuki, M., Takahashi, A., Suzuki, H., Sone, H., et al. 2004. SREBP-1 interacts with hepatocyte nuclear factor-4 alpha and interferes with PGC-1 recruitment to suppress hepatic gluconeogenic genes. *J Biol Chem* 279:12027-12035.

8. Biswas, N., Gayen, J. R., Mahata, M., Su, Y., Mahata, S., K., and O'Connor D, T. 2012. Novel peptide isomer strategy for stable inhibition of catecholamine release: Application to hypertension. *Hypertension* in press.

9. Jobson, A. G., Cardellina, J. H., 2nd, Scudiero, D., Kondapaka, S., Zhang, H., Kim, H., Shoemaker, R., and Pommier, Y. 2007. Identification of a Bis-guanylhydrazone [4,4'-Diacetyldiphenylurea-bis(guanylhydrazone); NSC109555] as a novel chemotype for inhibition of Chk2 kinase. *Molecular pharmacology* 72:876-884.

What is claimed is:

1. A method for treating an obese subject comprising administering an amount of a catestatin (CST) or a CST equivalent thereof to the obese subject so as to maintain an effective amount of circulating catestatin in the subject to promote lipolysis and oxidation of released fatty acids in both liver and adipose tissue, thereby reducing adipose tissue mass and hence treating obesity in the obese subject, wherein the CST equivalent is a retro-inverso version of CST, a CST variant having the sequence of SEQ ID NO:2, 3, 4, 55, 56, 57 or a retro-inverso thereof.

2. The method of claim 1, wherein the obesity to be treated is diet induced obesity.

3. The method of claim 1, wherein obesity in the obese subject is associated with a condition or disorder associated with reduced circulating CST, or decreased sensitivity of β-adrenergic receptor or combinations thereof.

4. The method of claim 1, wherein the subject has low plasma levels of naturally occurring CST.

5. The method of claim 1, wherein the CST or an equivalent thereof is administered by an enteral route, buccal route, intraperitoneal route, inhalation route, intravenous route, subcutaneous route or intramuscular route.

6. The method of claim 1, wherein the CST or its equivalent is a ligand for the leptin receptor (Ob-R).

7. The method of claim 6, wherein the CST or its equivalent is a partial agonist with leptin-like activity.

8. The method of claim 7, wherein the CST or its equivalent is able to compete with leptin for binding to leptin receptor (Ob-R).

9. The method of claim 8, wherein the binding to leptin receptor is through the Ig-like domain of Ob-R.

10. The method of claim 1, wherein the CST or CST equivalent is a peptide selected from the group consisting of
 a) amino-$S_{352}$SMKLSFRARAYGFRGPGPQL$_{372}$-carboxyl (SEQ ID NO:1) (human CST sequence (CHGA$_{352-372}$);
 b) amino-$S_{352}$SMKLSFRARAYS$_{364}$FRGPGPQL$_{372}$-carboxyl (SEQ ID NO:2) Human Gly364Ser variant sequence (CHGA$_{352-372}$);
 c) amino-$S_{352}$SMKLSFRARAYGFRGPGL$_{370}$QL$_{372}$-carboxy (SEQ ID NO:4) Human Pro370Leu variant sequence (CHGA$_{352-372}$);
 d) amino-$R_{344}$-SMRLSFRARGYGFRGPGLQL$_{364}$-carboxyl (SEQ ID NO:5) (bovine CST sequence (CHGA$_{344-364}$);
 e) amino-$R_{343}$SMRLSFRAPAYGFRGPGLQL$_{363}$-carboxyl (SEQ ID NO:6) (porcine CST sequence (CHGA$_{343-363}$);
 f) amino-$R_{367}$SMRLSFRARGYGFRDPGLQL$_{387}$-amino (SEQ ID NO:7) (rat CST sequence (CHGA$_{367-387}$)), g) amino-R$_{364}$SMRLSFRTRGYGFRDPGLQL$_{384}$-carboxyl (SEQ ID NO:8) (mouse CST sequence (CHGA$_{364-384}$)), h) amino-R$_{368}$SMKLSFRARAYGFRGPGPQL$_{388}$-carboxyl (SEQ ID NO:9) (Rhesus monkey CST sequence (CHGA$_{368-388}$)), i) amino-S$_{370}$SMKLPFRARAYGFRGPGPQL$_{390}$-carboxyl (SEQ ID NO:10) (Sumatran orangutan CST sequence (CHGA$_{370-390}$)), j) amino-R$_{361}$SMKLSFRARAYGFRGPGLQL$_{381}$-carboxyl (SEQ ID NO:11) (horse CST sequence (CHGA$_{361-381}$)), k) amino-R$_{352}$SMRLSFRARAYGFRGPGPQL$_{372}$-carboxyl (SEQ ID NO:55) (bovine CST sequence variant 1 (CHGA$_{352-372}$)), l) amino-R$_{370}$SMRLSFRARGYGFRGPGPQL$_{390}$-carboxyl (SEQ ID NO:56) (bovine CST sequence variant 2 (CHGA$_{370-390}$)), m) amino-R$_{384}$SMKLSFRTRAYGFRDPGPQL$_{404}$ (SEQ ID NO:57) (mouse CST sequence variant (CHGA$_{384-404}$)), n) amino-H$_{372}$SMKLSFRARAYGFGGPGPQL$_{392}$-carboxyl (SEQ ID NO:12) (squirrel monkey CST sequence (CHGA$_{372-392}$)), o) amino-S$_{462}$SMKLSFRARAYDFRGPGLQL$_{482}$-carboxyl (SEQ ID NO:13) (cat CST sequence (CHGA$_{462-482}$)), p) amino-H$_{370}$SMKLSFQARAYDFRGPGPQL$_{390}$-carboxyl (SEQ ID NO:14) (common marmoset CST sequence (CHGA$_{370-390}$)), q) amino-R$_{330}$SMKLSFRARAYDFRGPGLQL$_{350}$-carboxyl (SEQ ID NO:15) (giant panda bear CST sequence (CHGA$_{330-350}$ or CHGA$_{361-381}$)), r) amino-R$_{353}$SMKLSFRARAYGFRDPRPQL$_{373}$-carboxyl (SEQ ID NO:16) (Chinese hamster CST sequence (CHGA$_{353-373}$)), s) amino-R$_{361}$SMKLSFRAPAYGFRGPGLQL$_{381}$-carboxyl (SEQ ID NO:17) (wild boar CST sequence (CHGA$_{361-381}$)), t) amino-R$_{363}$SMKLSFRARAYDFRGPG$_{383}$ (SEQ ID NO:18) (dog CST sequence (CHGA$_{363-383}$)), u) amino-R$_{415}$SMKLSFRAQAYGFPGPEPQL$_{435}$-carboxyl (SEQ ID NO:19) (guinea pig CST sequence (CHGA$_{415-435}$)), v) amino-R$_{354}$SMKLSFRARGYGFGAPGPQL$_{374}$-carboxyl (SEQ ID NO:20) (David's myotis CST sequence (CHGA$_{354-374}$)), w) amino-R$_{362}$SMKLSLRARSYGFGGPGPQL$_{382}$-carboxyl (SEQ ID NO:21) (African bush elephant CST sequence (CHGA$_{362-382}$)), x) amino-R$_{382}$SMKLSLQTRAYDFRGPGPQL$_{402}$-carboxyl (SEQ ID NO:22) (small-eared galago CST sequence (CHGA$_{382-402}$)), y) amino-R$_{283}$SMKLSFQAPAYDFRGSGPQL$_{303}$-carboxyl (SEQ ID NO:23) (naked mole rat CST sequence (CHGA$_{283-303}$)), z) amino-R$_{318}$SMKLSFQSRAYGFRGPRHQL$_{338}$-carboxyl (SEQ ID NO:24) (Chinese tree shrew CST sequence (CHGA$_{318-338}$)), aa) amino-R$_{358}$AMKLSFRARGYDFSGPGLQL$_{378}$-carboxyl (SEQ ID NO:25) (killer whale CST sequence (CHGA$_{358-378}$)), and bb) Amino-S$_{352}$SMKLSFRARAYGFRV$_{367}$PGPQL$_{372}$-carboxyl (SEQ ID NO:3) Human Gly364Val variant sequence (CHGA$_{352-372}$).

11. The method of claim 1, wherein the equivalent of catestatin is a retro-inverso peptide comprising D-amino acid in place of L-amino acid except for achiral glycine and an inverse order of the amino-to-carboxyl sequence for any of the sequences selected from the group consisting of a) amino-S$_{352}$SMKLSFRARAYGFRGPGPQL$_{372}$-carboxyl (SEQ ID NO:1) (human CST sequence (CHGA$_{352-372}$);

b) amino-S$_{352}$SMKLSFRARAYS$_{364}$FRGPGPQL$_{372}$-carboxyl (SEQ ID NO:2) Human Gly364Ser variant sequence (CHGA$_{352-372}$);

c) amino-S$_{352}$SMKLSFRARAYGFRGPGL$_{370}$QL$_{372}$-carboxy (SEQ ID NO:4) Human Pro370Leu variant sequence (CHGA$_{352-372}$);

d) amino-R$_{344}$-SMRLSFRARGYGFRGPGLQL$_{364}$-carboxyl (SEQ ID NO:5) (bovine CST sequence (CHGA$_{344-364}$), e) amino-R$_{343}$SMRLSFRAPAYGFRGPGLQL$_{363}$-carboxyl (SEQ ID NO:6) (porcine CST sequence (CHGA$_{343-363}$), f) amino-R$_{367}$SMRLSFRARGYGFRDPGLQL$_{387}$-amino (SEQ ID NO:7) (rat CST sequence (CHGA$_{367-387}$)), g) amino-R$_{364}$SMRLSFRTRGYGFRDPGLQL$_{384}$-carboxyl (SEQ ID NO:8) (mouse CST sequence (CHGA$_{364-384}$)), h) amino-R$_{368}$SMKLSFRARAYGFRGPGPQL$_{388}$-carboxyl (SEQ ID NO:9) (Rhesus monkey CST sequence (CHGA$_{368-388}$)), i) amino-S$_{370}$SMKLPFRARAYGFRGPGPQL$_{390}$-carboxyl (SEQ ID NO:10) (Sumatran orangutan CST sequence (CHGA$_{370-390}$)), j) amino-R$_{361}$SMKLSFRARAYGFRGPGLQL$_{381}$-carboxyl (SEQ ID NO:11) (horse CST sequence (CHGA$_{361-381}$)), k) amino-R$_{352}$SMRLSFRARAYGFRGPGPQL$_{372}$-carboxyl (SEQ ID NO:55) (bovine CST sequence variant 1 (CHGA$_{352-372}$)), l) amino-R$_{370}$SMRLSFRARGYGFRGPGPQL$_{390}$-carboxyl (SEQ ID NO:56) (bovine CST sequence variant 2 (CHGA$_{370-390}$)), m) amino-R$_{384}$SMKLSFRTRAYGFRDPGPQL$_{404}$ (SEQ ID NO:57) (mouse CST sequence variant (CHGA$_{384-404}$)), n) amino-H$_{372}$SMKLSFRARAYGFGGPGPQL$_{392}$-carboxyl (SEQ ID NO:12) (squirrel monkey CST sequence (CHGA$_{372-392}$)), o) amino-S$_{462}$SMKLSFRARAYDFRGPGLQL$_{482}$-carboxyl (SEQ ID NO:13) (cat CST sequence (CHGA$_{462-482}$)), p) amino-H$_{370}$SMKLSFQARAYDFRGPGPQL$_{390}$-carboxyl (SEQ ID NO:14) (common marmoset CST sequence (CHGA$_{370-390}$)), q) amino-R$_{330}$SMKLSFRARAYDFRGPGLQL$_{350}$-carboxyl (SEQ ID NO:15) (giant panda bear CST sequence (CHGA$_{330-350}$ or CHGA$_{361-381}$)), r) amino-R$_{353}$SMKLSFRARAYGFRDPRPQL$_{373}$-carboxyl (SEQ ID NO:16) (Chinese hamster CST sequence (CHGA$_{353-373}$)), s) amino-R$_{361}$SMKLSFRAPAYGFRGPGLQL$_{381}$-carboxyl (SEQ ID NO:17) (wild boar CST sequence (CHGA$_{361-381}$)), t) amino-R$_{363}$SMKLSFRARAYDFRGPG$_{383}$ (SEQ ID NO:18) (dog CST sequence (CHGA$_{363-383}$)), u) amino-R$_{415}$SMKLSFRAQAYGFPGPEPQL$_{435}$-carboxyl (SEQ ID NO:19) (guinea pig CST sequence (CHGA$_{415-435}$)), v) amino-R$_{354}$SMKLSFRARGYGFGAPGPQL$_{374}$-carboxyl (SEQ ID NO:20) (David's myotis CST sequence (CHGA$_{354-374}$)), w) amino-$R_{362}$SMKLSLRARSYGFGGPGPQL$_{382}$-carboxyl (SEQ ID NO:21) (African bush elephant CST sequence (CHGA$_{362-382}$)), x) amino-$R_{382}$SMKLSLQTRAYDFRGPGPQL$_{402}$-carboxyl (SEQ ID NO:22) (small-eared galago CST sequence (CHGA$_{382-402}$)), y) amino-$R_{283}$SMKLSFQAPAYDFRGSGPQL$_{303}$-carboxyl (SEQ ID NO:23) (naked mole rat CST sequence (CHGA$_{283-303}$)), z) amino-$R_{318}$SMKLSFQSRAYGFRGPRHQL$_{338}$-carboxyl (SEQ ID NO:24) (Chinese tree shrew CST sequence (CHGA$_{318-338}$)), aa) amino-$R_{358}$AMKLSFRARGYDFSGPGLQL$_{378}$-carboxyl (SEQ ID NO:25) (killer whale CST sequence (CHGA$_{358-378}$)), and bb) Amino-$S_{352}$SMKLSFRARAYGFRV$_{367}$PGPQL$_{372}$-carboxyl (SEQ ID NO:3) Human Gly367Val variant sequence (CHGA$_{352-372}$).

\* \* \* \* \*